United States Patent [19]

Yamashita et al.

[11] Patent Number: 5,354,839

[45] Date of Patent: Oct. 11, 1994

[54] POLYIMIDE AND PREPARATION PROCESS OF SAME

[75] Inventors: Wataru Yamashita; Yoshihiro Sakata; Toshiyuki Kataoka; Yuichi Okawa; Hideaki Oikawa; Tadashi Asanuma; Mitsunori Matsuo; Tsutomu Ishida, all of Kanagawa; Keizaburo Yamaguchi, Chiba; Akihiro Yamaguchi, Kanagawa, all of Japan

[73] Assignee: Mitsui Toatsu Chemicals, Incorporated, Tokyo, Japan

[21] Appl. No.: 40,608

[22] Filed: Mar. 31, 1993

[30] Foreign Application Priority Data

| Apr. 7, 1992 | [JP] | Japan | 4-085466 |
| Apr. 22, 1992 | [JP] | Japan | 4-102815 |
| Sep. 17, 1992 | [JP] | Japan | 4-247872 |
| Sep. 18, 1992 | [JP] | Japan | 4-249631 |
| Nov. 12, 1992 | [JP] | Japan | 4-302271 |
| Nov. 20, 1992 | [JP] | Japan | 4-312039 |
| Nov. 27, 1992 | [JP] | Japan | 4-318818 |

[51] Int. Cl.$^5$ ............... C08G 73/10; C08G 69/26
[52] U.S. Cl. ............... 528/188; 528/125; 528/128; 528/170; 528/172; 528/173; 528/174; 528/176; 528/183; 528/185; 528/220; 528/229; 528/350; 528/351; 528/353
[58] Field of Search .......... 528/353, 125, 128, 170, 528/172, 173, 174, 176, 183, 188, 185, 220, 229, 350, 351

[56] References Cited

U.S. PATENT DOCUMENTS 4,065,345 12/1977 Progar et al. ............... 528/353

FOREIGN PATENT DOCUMENTS

| 192480 | 8/1986 | European Pat. Off. |
| 269319 | 6/1988 | European Pat. Off. |
| 299865 | 1/1989 | European Pat. Off. |
| 350203 | 1/1990 | European Pat. Off. |
| 365311 | 4/1990 | European Pat. Off. |
| 1-182324 | 7/1989 | Japan |
| 1-190652 | 7/1989 | Japan |
| 2-18419 | 1/1990 | Japan |
| 2-60933 | 3/1990 | Japan |
| 2-281037 | 11/1990 | Japan |
| 4-122729 | 4/1992 | Japan |
| 2229180 | 9/1990 | United Kingdom |

OTHER PUBLICATIONS

Chemical Abstracts, vol. 116, No. 6, Feb. 10, 1992, JPA-306529.
Chemical Abstracts, vol. 112, No. 20, May 14, 1990, JPA-1261422.

Primary Examiner—John Kight, III
Assistant Examiner—P. Hampton-Hightower
Attorney, Agent, or Firm—Burns, Doane, Swecker & Mathis

[57] ABSTRACT

A polyimide comprising a requisite structural unit having one or more recurring structural units of the formula:

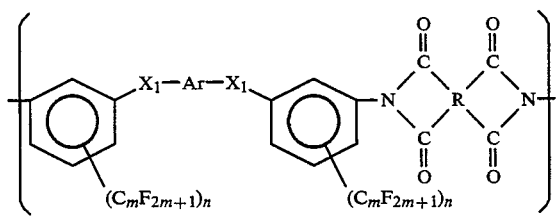

such as the structural units of the formula

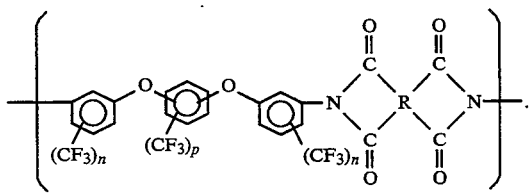

The polyimide can have an extremely low dielectric constant and is colorless, transparent and excellent in processability and heat resistance, and also provides an aromatic diamine which is useful as a raw material monomer of the polyimide or a raw material of other various engineering plastics.

28 Claims, 4 Drawing Sheets

POLYIMIDE AND PREPARATION PROCESS OF SAME

BACKGROUND OF THE INVENTION

1. Field of the Invention

The present invention relates to fluorine containing polyimide, a novel aromatic diamine which has a perfluoro alkyl radical and can be used as a raw material monomer for the polyimide, and a process for preparing the same. More particularly, the invention relates to a novel thermoplastic polyimide which contains fluorine, has an extremely low dielectric constant and hygroscopic property, and is excellent in processability; a preparation process of the thermoplastic polyimide; a novel aromatic diamine compound which has a perfluoroalkyl radical such as trifluoromethyl and is useful as a raw material monomer for the polyimide, for a starting material of polyamide, polyamideimide, bismaleimide and epoxy resin, and as a raw material for organic chemicals; and a process for preparing the aromatic diamine compound.

2. Related Art of the Invention

Polyimide is prepared by reaction of tetracarboxylic dianhydride with diamine. Conventionally known polyimide has an essential characteristic of high heat resistance, is additionally excellent in mechanical strengths, chemical resistance and dimensional stability, and also has flame retardance and electrical insulation property. Consequently, polyimide has been used in electric and electronic fields, particularly in the field where heat resistance is required, and is expected in the future to be used in other application fields and in increased amounts.

Polyimide having excellent characteristics has conventionally been developed. However, conventionally known polyimide has no distinct glass transition temperature though excellent in heat resistance and hence must be processed by such means as sintering in the case of being used as a molded article. In other cases, polyimide is soluble in halogenated hydrocarbon solvents and causes problems on solvent resistance though excellent in processability. Thus, both merits and drawbacks have been found in the properties of polyimide.

Recently, polyimide having improved properties or having a novel performance has been developed in order to extend the utilization fields of polyimide. For example, there has been developed a thermoplastic polyimide of the formula (A):

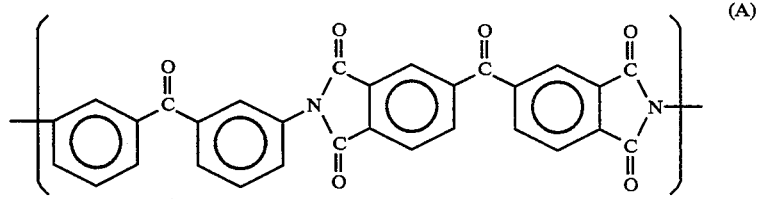

(A)

The polyimide has been disclosed by Proger et al. as a heat resistant adhesive in U.S. Pat. No. 4,065,345. Ohta et al. have provided the polyimide with a new performance of injection ability by controlling the molecular weight of the polymer and capping the reactive end of the polymer chain in Japanese Laid-Open Patent Hei 2-018419.

Development in microelectronics has recently been remarkable in the electric and electronic field. Development research has been extensively conducted in particular on the insulation material for use in a multi-layered circuit substrate. In organic materials applied to the field, polyimide in particular is used as a suitable material for insulation because of excellent heat resistance and dimensional stability and a low dielectric constant as compared with inorganic materials. The dielectric constant of presently marketed polyimide resin is, however, unsatisfactory. For example, the polyimide KAPTON (Trade Mark) prepared from 4,4'-diaminodiphenyl ether and pyromellitic dianhydride has a dielectric constant of 3.6 at 1 KHz, the polyimide UPILEX (Trade Mark) prepared from 4,4'-diaminodiphenyl ether and biphenyltetracarboxylic dianhydride has a dielectric constant of 3.5 at 1 MHz, and the polyimide LARC-TP1 (Trade Mark) prepared from 3,3'-diaminobenzophenone and benzophenonetetracarboxylic dianhydride has a dielectric constant of 3.7 at 1 MHz. Polyimide resin has already been used for an insulation material of a flexible printed-circuit substrate. High integration of an electronic circuit has recently been more extended, and accordingly, improvement in electrical characteristics, for example, lowering of the dielectric constant has been strongly desired. Practically, insulation materials having a low dielectric constant of 3.0 or less, preferably about 2.8 have been desired.

Particularly in large-sized computers, high speed transfer of signals by use of 2 multi-layered circuit substrates is inevitable. However, a high dielectric constant of the circuit material leads to a transfer lag of signals and inhibits high speed transfer. Polyimide is used for an interlayer insulation film in multi-layered wiring. Accordingly, attention has been focused to develop polyimide having a low dielectric constant in particular in addition to the above characteristics of conventional polyimide.

Teflon resin has been known as a resin having a low dielectric constant. Investigations for decreasing the dielectric constant has also been carried out on polyimide having heat resistance and other various excellent properties as an engineering polymer. Reduction of a dielectric constant by introduction of fluorine or a fluoro radical into the structure of polyimide has been reported, for example, in A. K. st. Clair et al. Polymeric Materials Science and Engineering, 59, 28~32 (1988) and EP 0299865.

That is, introduction of a fluorine atom into the molecular unit of polyimide has been known as a means of reducing the dielectric constant of polyimide. In order to achieve such object, an aromatic diamino compound having a hexafluoroisopropylidene radical has been disclosed as a polyimide monomer used for preparing materials of low dielectric constant (Japanese Laid-open Patent Hei 1-190652).

These aromatic diamine compounds, however, require many steps in preparation and also have problems in industry that the resultant polyimide resin has insufficient melt-flowability in processing.

An aromatic diamino compound which has a biphenyl structure and a trifluoromethyl radical in the molecule is, for example, 4,4'-bis(3-trifluoromethyl-4-aminophenoxy) biphenyl of the formula (B):

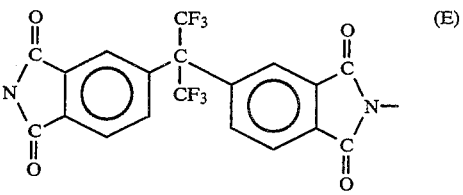

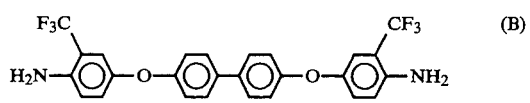

The compound, however, has an electron absorbing trifluoromethyl radical in the ortho position to an amino radical and is hence known that the compound is difficult to react with acid anhydride due to an electric factor and is difficult to increase degree of polymerization.

Since the amino group is located in the para position to the connecting radical, the resulting polyimide has a rigid structure and causes a problem of difficulty in processing.

Other fluorine containing polyimides having low dielectric constant have conventionally been proposed, for example, in Japanese Laid-Open Patent Hei 1-182324, 2-60933, 2-281037 and 4-122729. These polyimides are very expensive or difficult to manufacture in industry and it is hence desired to develop a polyimide which is free from these disadvantages and has a low dielectric constant.

Development of plastics having excellent transparency in addition to a low dielectric constant has also been carried out extensively in order to obtain engineering plastics applied to the electric and electronic fields. A plastic which has excellent transparency and is widely used is polycarbonate of the formula (C):

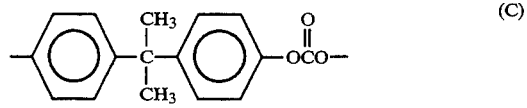

The plastic, however, has low glass transition temperature of about 150° C. and hence heat resistance is unsatisfactory. Another known transparent resin is polyether sulfone of the formula (D):

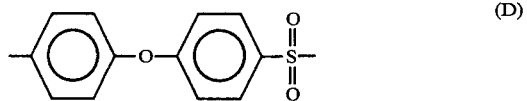

The resin, however, has a sulfonyl radical which has a high hygroscopic property and thus cannot be used for electric and electronic materials which must be free from moisture.

Further, various kinds of transparent polyimide have also been developed. For example, polyimide having an excellent yellowness index has been disclosed in Japanese Laid-Open patent Hei 1-182324 and has the formula (E):

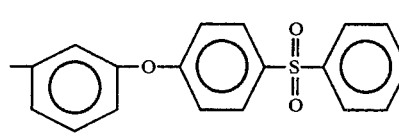

However, the polyimide also has a problem of hygroscopic property due to the presence of a sulfonyl radical as in the case of the above polyether sulfone.

Problems generally found in polyimide resins have been coloration and higher dielectric constant than other resin such as Teflon which has a low dielectric constant.

Coloration is a very important problem in the development of optical communication cables and optical materials such as filters and liquid crystals which are used for construction of a highly heat-resistant and reliable communication system. Practically, the yellowness index (hereinafter referred to as YI) is used as a parameter of yellowness. YI is 129 for the polyimide KAPTON (Trade Mark) prepared from 4,4'-diaminodiphenyl ether and pyromellitic dianhydride, 125 for the polyimide UBILEX (Trade Mark) prepared from 4,4'-diaminodiphenyl ether and biphenyltetracarboxylic dianhydride, and 50 for the polyimide LARC-TPI (Trade Mark) prepared from 3,3'-diamino benzophenone and benzophenonetetracarboxylic dianhydride.

All of these YI values are too high. YI of 10 or less is desired for use in the above optical materials. Polyimide resin is desired to have YI of 4~48 which is equal to that of polycarbonate for present optical applications.

SUMMARY OF THE INVENTION

One object of the invention is to provide a polyimide having a dielectric constant and excellent processability, and a process for preparing the polyimide.

A second object of the invention is to provide a polyimide having good transparency and a process for preparing the polyimide.

A third object of the invention is to provide a novel fluorine containing aromatic diamine which is useful as a raw material monomer of the polyimide and a process for preparing the same.

As a result of an intensive investigation in order to achieve the above objects, the present inventors have found that polyimide having a low dielectric constant and excellent transparency can be obtained by using an aromatic diamine monomer wherein the molecule comprises 3~4 aromatic rings, two amino radicals are individually located on each terminal benzene ring at the meta position to the molecular chain connecting radical, and one or more perfluoro radicals are located on each aromatic ring.

They have also found a novel fluorine containing aromatic diamine which is useful for the monomer of polyimide having the above properties, and have succeeded in the preparation of the novel diamine. Thus, the invention has been completed.

That is, the present invention is:

(1) A polyimide comprising a requisite structural unit having one or more recurring structural units of the formula (1):

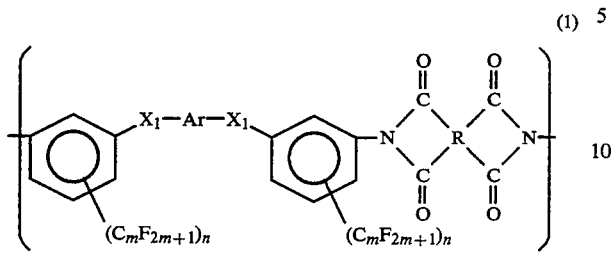

wherein $X_1$ is a divalent radical selected from the group consisting of —O—, —CO— and —C(CH$_3$)$_2$— and two $X_1$ may be the same or different each other, m is an integer of 1~6, n is individually 0 or an integer of 1~4, R is a tetravalent radical having 2~27 carbon atoms and being selected from the group consisting of aliphatic radical, alicyclic radical, monoaromatic radical, comdensed polyaromatic radical and noncondensed aromatic radical connected each other with a direct bond or a bridge member, and Ar is a divalent radical selected from the group consisting of

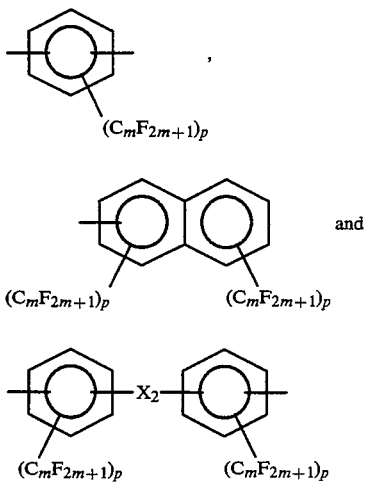

wherein $X_2$ is a divalent radical selected from the group consisting of a direct bond, —O—, —S—, —CO—, and C(CH$_3$)$_2$—, m is an integer of 1~6, and p is individually 0 or an integer of 1~4, or an integer of 1~4 when n is 0 in the formula (1).

The polyimide of the formula (1) practically includes the described polyimides:

(2) An aromatic polyimide comprising a requisite structural units having one or more recurring structural units of the formula (2):

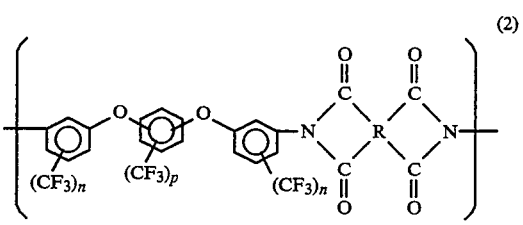

wherein n and p are 0 (simultaneously 0, exclusive) or an integer of 1~4, and R is the same as in the formula (1).

(3) An aromatic polyimide comprising a requisite structural unit having one or more recurring structural units of the formula (3):

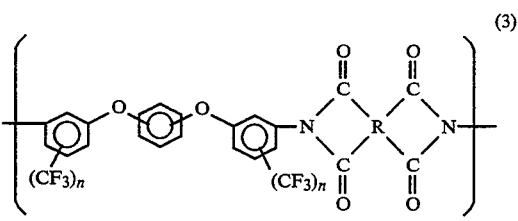

wherein n is an integer of 1–4 and R is the same as in the formula (1).

(4) An aromatic polyimide comprising a requisite structural unit having one or more recurring structural units of the formula (4):

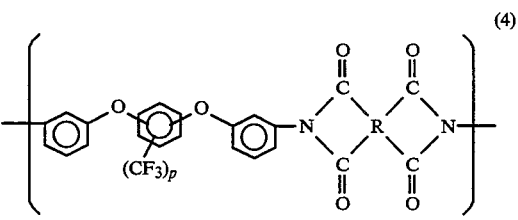

wherein p is an integer of 1~4 and R is the same as in the formula (1).

The polyimides of the formulas (2), (3) and (4) more practically include the below described polyimides:

(5) An aromatic polyimide comprising a requisite structural units having one or more recurring structural units selected from the group consisting of the formulas (5), (6), (7), (8), (9) and (10):

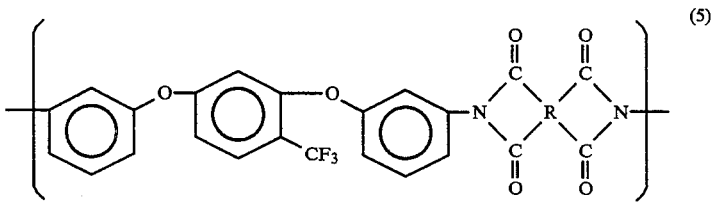

-continued

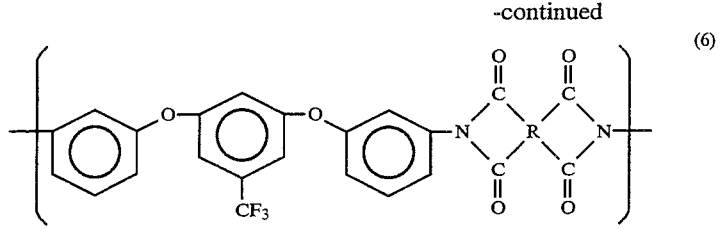
(6)

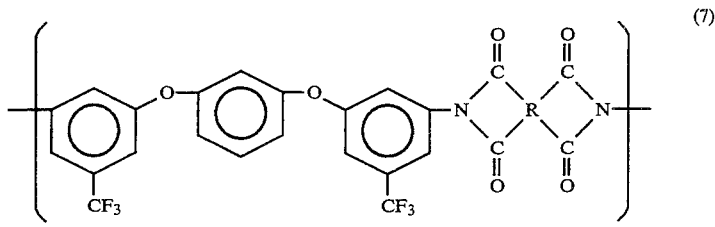
(7)

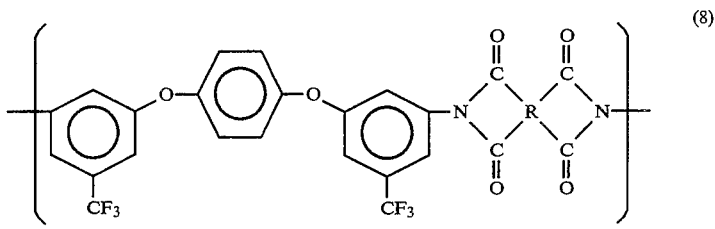
(8)

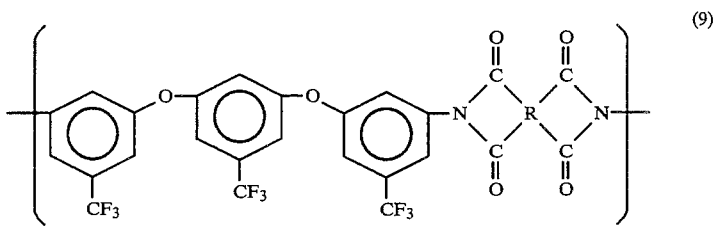
(9)

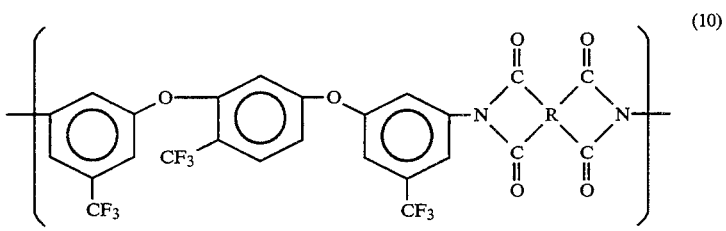
(10)

wherein R is the same as above.

(6) An aromatic polyimide comprising a requisite structural units having one or more recurring structural units of the formula (11):

—CO—, and —C(CH$_3$)$_2$—, n and p are 0 (simultaneously 0, exclusive) or an integer of 1~4, and R is the same as in the formula (1).

(7) An aromatic polyimide comprising a requisite struc-

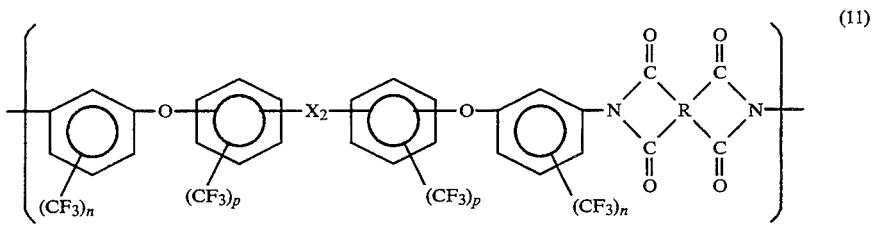
(11)

wherein X$_2$ is a direct bond or a divalent radical selected from the group consisting of —O—, —S—, tural units having one or more recurring structural units of the formula (12):

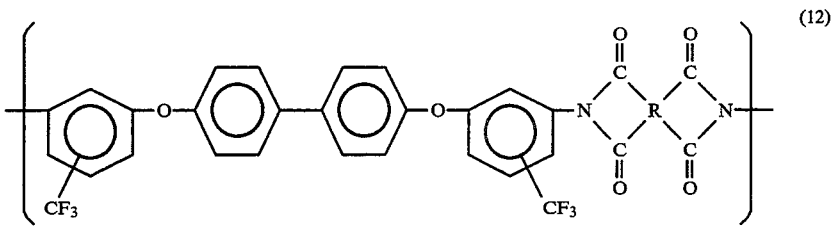

wherein R is the same as in the formula (1).

(8) An aromatic polyimide of the above (1)~(7) having at the polymer chain end an aromatic ring unsubstituted or substituted with a radical having no reactivity for amine and dicarboxylic anhydride.

That is, a capped aromatic polyimide obtained by capping the polymer chain end with aromatic dicarboxylic anhydride of the formula (15):

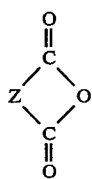

wherein Z is a divalent radical having 6~15 carbon atoms and being selected the group consisting of a monoaromatic radical condensed polyaromatic radical and noncondensed aromatic radical connected to each other with a direct bond or a bridge member and/or aromatic monoamine of the formula (16):

$Z_1-NH_2$     (16)

wherein $Z_1$ is a monovalent radical having 6~15 carbon atoms and being selected from the group consisting of a monoaromatic radical, condensed polyaromatic radical and noncondensed aromatic radical connected to each other with a direct bond or a bridge member, preferably by capping with phthalic anhydride or aniline.

Another aspect of the invention is a process for preparing the polyimide, that ms:

(9) A process for preparing a polyimide comprising requisite structural units having one or more recurring structural units of the formula (1:

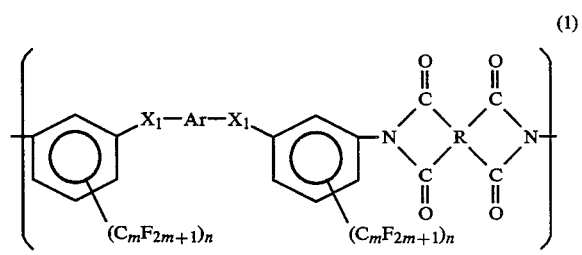

wherein $X_1$, Ar, m, n, and R are the same as above, which comprises reacting an aromatic diamine having one or more principal ingredients of the formula (13):

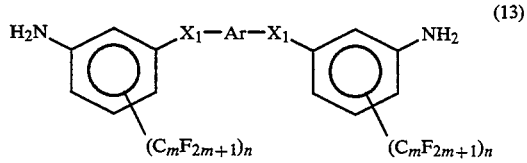

wherein $X_1$ is a direct bond or a divalent radical selected from the group consisting of —O—, —CO—, and —C(CH$_3$)$_2$—, two $X_1$ may be the same or different, m is an integer of 1~6, n is 0 or an integer of 1~4, and Ar is a divalent radical selected from the group consisting of

wherein $X_2$ is a divalent radical selected from the group consisting of a direct bond, —O—, —S—, —CO—, and —C(C$_3$)$_2$—, m is an integer of 1~6, and p is individually 0 or an integer 1~4 and an integer of 1~4 when n is 0 in the formula (13), with one or more tetracarboxylic dianhydride principally represented by the formula (14):

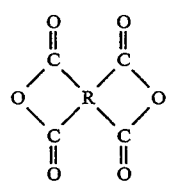

wherein R is a tetravalent radical having 2~27 carbon atoms and being selected from the group consisting of an aliphatic radical, alicyclic radical, monoaromatic radical, condensed polyaromatic radical and noncondensed aromatic radical connected to each other with a direct bond or a bridge member, and thermally or chemically imidizing the resulting polyamic acid.

(10) A process for preparing a capped aromatic polyimide having recurring structural units of the formula (1):

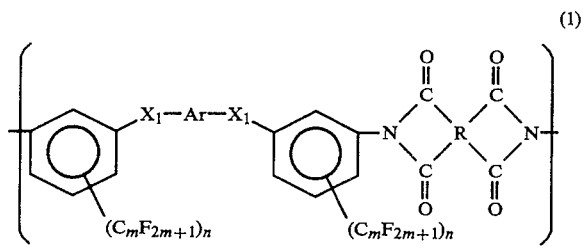

wherein $X_1$, Ar, m, n and R are the same as above, and having at the polymer chain end thereof an aromatic ring which is essentially unsubstituted or substituted with a radical having no reactivity for amine and dicarboxylic anhydride, comprising reacting aromatic diamine having one or more principal ingredients of the formula (13):

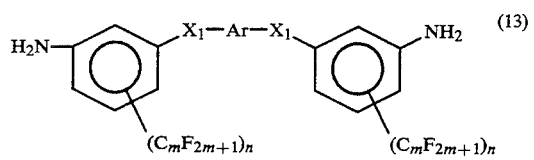

wherein $X_1$, Ar, m and n are the same as in the formula (13), with one or more tetracarboxylic dianhydride principally represented by the formula (14)

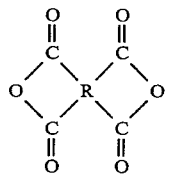

wherein R is the same as above, in the presence of aromatic dicarboxylic anhydride of the formula (15):

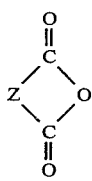

wherein Z is the same as above, and/or aromatic monoamine of the formula (16):

$$Z_1\text{—}NH_2 \quad (16)$$

wherein $Z_1$ is the same as above, and thermally or chemically imidizing the resulting polyamic acid.

(11) The preparation processes above described wherein the aromatic diamine has the formula (18):

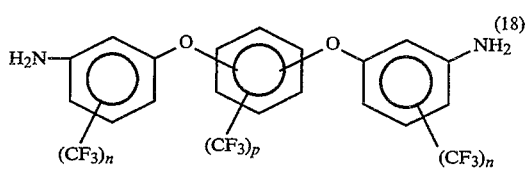

wherein n and p are 0 or an integer of 1, and are not simultaneously 0.

(12) The preparation processes above described wherein the aromatic diamine has the formula (19):

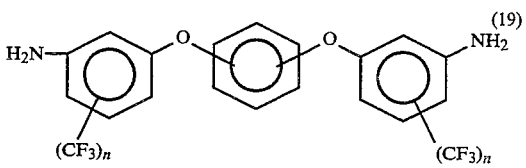

wherein n is an integer of 1~4.

(13) The preparation processes above described wherein the aromatic diamine has the formula (20):

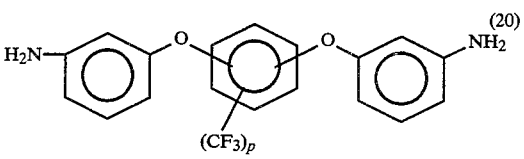

wherein p is an integer of 1~4.

(14) The preparation processes above described wherein the aromatic diamine is one or more compounds selected from the group consisting of
1,3-bis(3-aminophenoxy)-4-trifluoromethylbenzene,
1,3-bis(3-aminophenoxy)-5-trifluoromethylbenzene,
1,3-bis(3-amino-5-trifluoromethylphenoxy)benzene,
1,4-bis(3-amino-5-trifluoromethylphenoxy)benzene,
1,3-bis(3-amino-5-trifluoromethylphenoxy)-5-trifluoromethylbenzene and
1,3-bis(3-amino-5-trifluoromethylphenoxy)-4-trifluoromethylbenzene.

(15) The preparation processes above described wherein the aromatic diamine has the formula (21):

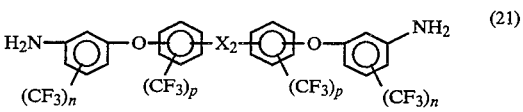

wherein $X_2$ is a direct bond or a divalent radical selected from the group consisting of —O—, —S—, —CO—, and —C(CH$_3$)$_2$—, and n and p are individually 0 or an integer of 1~4 and are not simultaneously 0.

(16) The preparation processes above described wherein the aromatic diamine has the formula (22):

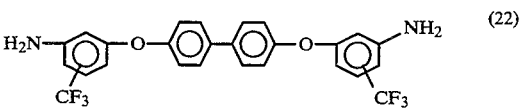

A still further aspect of the invention is a novel aromatic diamine which is useful for preparing the above polyimide having a low dielectric constant, that is:

(17) An aromatic diamine having the formula (17):

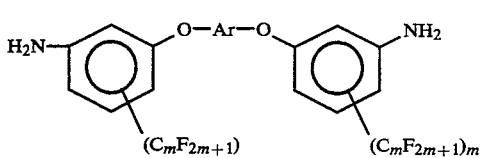

wherein m is an integer of 1~6, n is 0 or an integer of 1~4, and Ar ms a divalent radical selected from the group consisting of

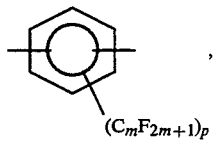

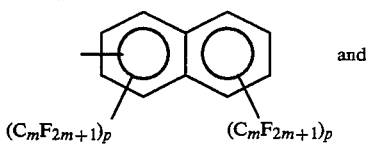

and

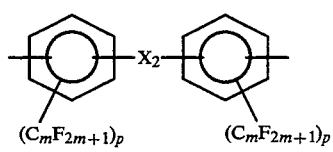

wherein $X_2$ is a direct bond or a divalent radical selected from the group consisting of —O—, —S—, —CO—, and —C(C$_3$)$_2$—, m is an integer of 1~6, and p is 0 or an integer of 1~4 and is an integer of 1~4 when n is 0 in the formula (17).

(18) An aromatic diamine having the formula (18):

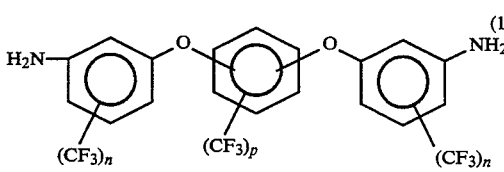

wherein n and p are 0 or an integer of 1~4 and are not simultaneously 0.

(19) An aromatic diamine wherein the aromatic diamine of the formula (2) has the formula (19):

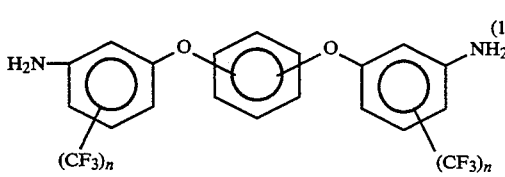

wherein n is integer of 1~4.

(20) An aromatic diamine having the formula (20):

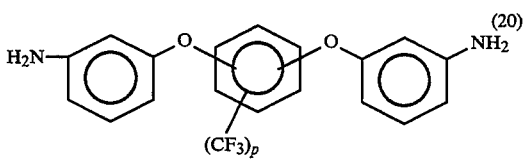

wherein p is integer of 1~4.

(21) An aromatic diamine selected from
1,3-bis(3-aminophenoxy)-4-trifluoromethylbenzene,
1,3-bis(3-aminophenoxy)-5-trifluoromethylbenzene,
1,3-bis(3-amino-5-trifluoromethylphenoxy)benzene,
1,4-bis(3-amino-5-trifluoromethylphenoxy)benzene,
1,3-bis(3-amino-5-trifluoromethylphenoxy)-5-trifluoromethylbenzene or
1,3-bis(3-amino-5-trifluoromethylphenoxy)-4-trifluoromethylbenzene.

(22) An aromatic diamine wherein the aromatic diamine of the formula (17) has the formula (21):

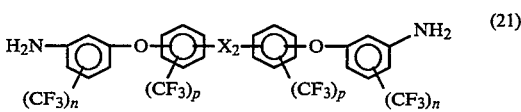

wherein $X_2$ is a direct bond or a divalent radical selected from the group consisting of —O—, —S—, —CO—, and —C(CH$_3$)$_2$— and n and p are 0 or integer of 1~4 and are not simultaneously 0.

(23) An aromatic diamine having the formula (22):

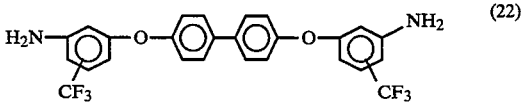

(24) An aromatic diamine 4,4'-bis(3-amino-5-trifluoromethylphenoxy) biphenyl.

A further aspect of the invention is a process for preparing the above aromatic diamine, that is:

(25) A process for preparing an aromatic diamine compound of the formula (17):

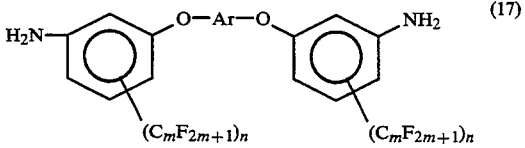

wherein Ar, m and n are the same as above, comprising reacting a dihalogeno or dinitro compound of the formula (23):

Y—Ar—Y (23)

wherein Y is a halogen atom or a nitro radical, and Ar is a divalent radical radical selected from the group consisting of

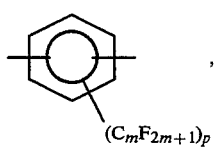

-continued

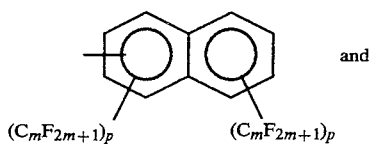 and

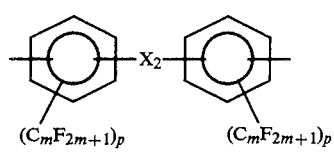

wherein $X_2$ is a divalent radical selected from the group consisting of —O—, —S—, —CO—, and —C(C$_3$)$_2$—, m is an integer of 1~6, and p is 0 or an integer of 1~4, with a m-nitrophenol derivative of the formula (24):

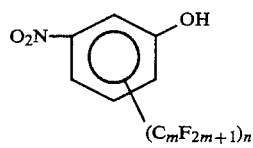 (24)

wherein m is an integer of 1~6, and n is 0 or an integer of 1~4 and is an integer of 1~4 when p is 0 in the formula (23), at 100°~250° C. in an aprotic polar solvent in the presence of a base and successively reducing the resultant aromatic dinitro compound.

(26) A process for preparing an aromatic diamine compound of the formula (17):

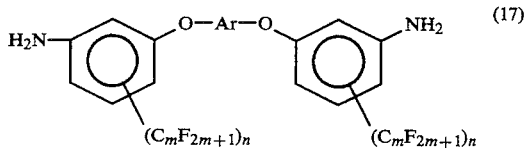 (17)

wherein At, m and n are the same as above, comprising reacting a dihydroxy compound of the formula (25):

HO—Ar—OH (25)

wherein Ar is a divalent radical selected from the group consisting of

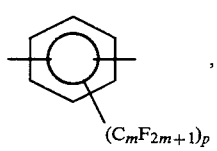 ,

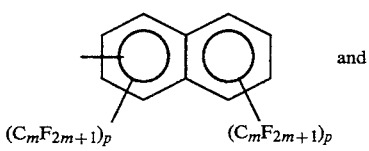 and

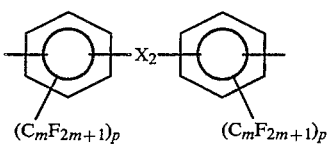

wherein $X_2$ is a divalent radical selected from the group consisting of —O—, —S—, —CO—, and —C(C$_3$)$_2$—, m is an integer of 1~6, and p is 0 or an integer of 1~4, with a m-dinitro or m-nitrohalogeno compound of the formula (26):

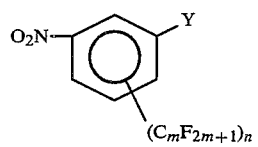 (26)

wherein Y is a halogen atom or a nitro radical, m is an integer of 1~6, and n is 0 or an integer of 1~4 and is an integer of 1~4 when p is 0 in the formula (25), at 100°~250° C. in an aprotic solvent in the presence of a base and successively reducing the resultant aromatic dinitro compound.

(27) A process for preparing an aromatic diamine compound of the formula (17):

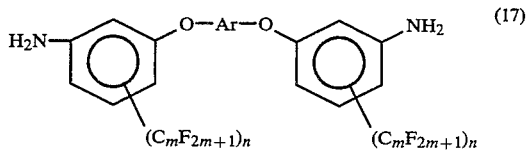 (17)

wherein Ar, m and n are the same as above, comprising reacting a dihalogeno or dinitro compound of the formula (23):

Y—Ar—Y (23)

wherein Y is a halogen atom or a nitro radical, and Ar is a divalent radical selected from the group consisting of

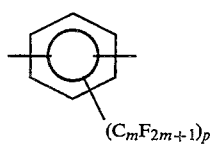 ,

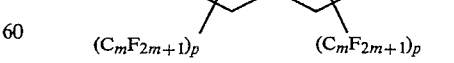 and

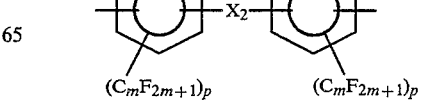

wherein $X_2$ is a direct bond or a divalent radical selected from the group consisting of —O—, —S—, —CO—, and —C(C$_3$)$_2$—, m is an integer of 1~6, is 0 or an integer of 1~4, with a m-aminophenol derivative of the formula (27):

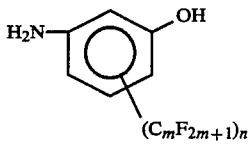

(27)

wherein m is an integer of 1~6, and n is 0 or an integer of 1~4 and an integer of 1~4 when p is 0 in the formula (23), at 100°~250° C. in an aprotic polar solvent in the presence of a base.

A still further aspect of the invention is a polyimide wherein the polyamic acid, the precursor of the polyimide, has an inherent viscosity of 0.01~3.0 dl/g at a concentration of 0.5 g/dl in a dimethylacetamide solution at 35° C., or a polyimide wherein a solution of the polyimide powder at a concentration of 0.5 g/dl in a solvent mixture composed of 9 parts by weight of p-chlorophenol and 1 part by weight of phenol has an inherent viscosity of 0.01~3.0 dl/g at 35° C.

The present invention can provide a polyimide which has an extremely low dielectric constant and is colorless, transparent and excellent in processability and heat resistance.

The invention also provides an aromatic diamine which is useful as a raw material monomer for the polyimide or as a raw material for various other engineering plastics.

The polyimide of the invention has excellent characteristics and thus wide utilization is expected in industry, particularly in the fields of electric and electronic materials and optical materials.

DETAILED DESCRIPTION OF THE INVENTION

Figure 1:
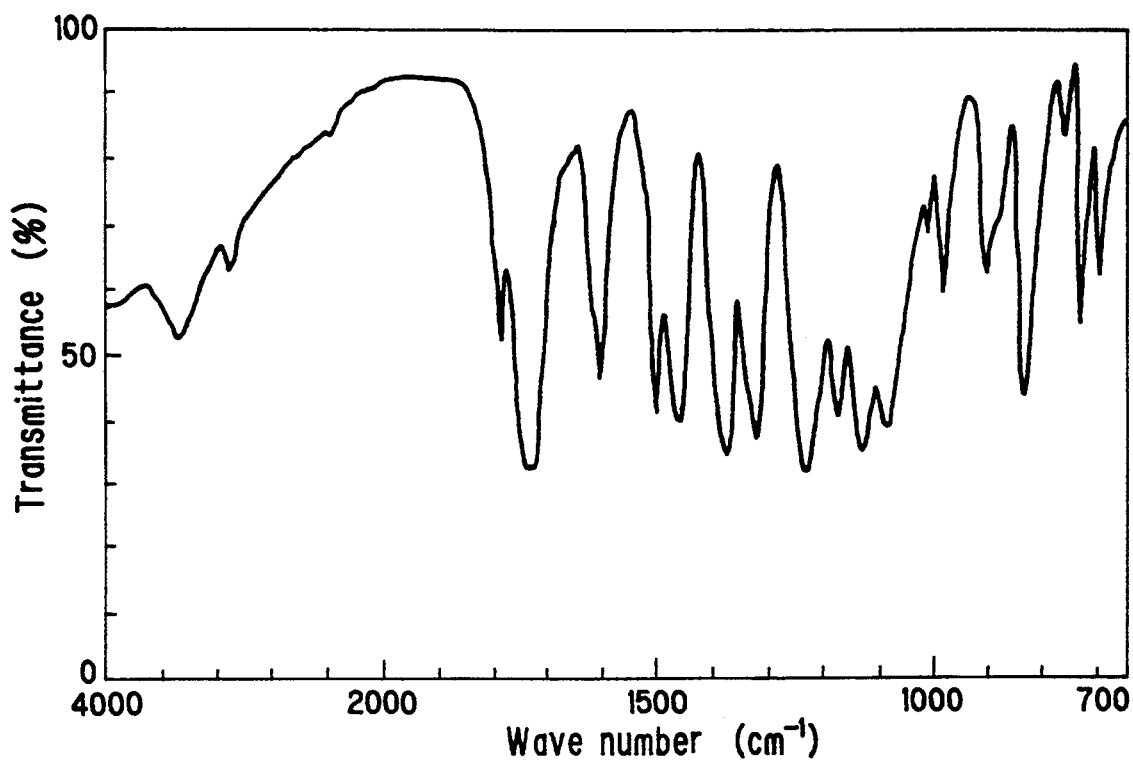
FIG. 1 illustrates an infrared absorption spectrum of the polyimide powder obtained in Example 8.

The polyimide of the invention comprises requisite structural units having one or more recurring structural units of the formula (1):

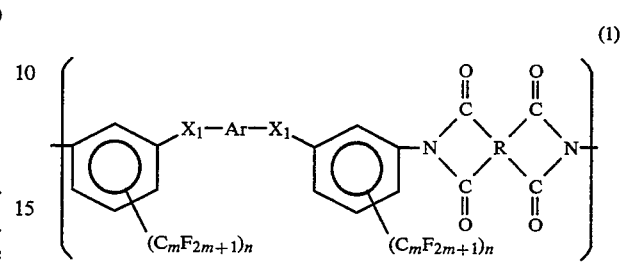

(1)

wherein $X_1$ is a direct bond or a divalent radical selected from the group consisting of —O—, —CO—, and —C(C$_3$)$_2$— and two $X_1$ may be same or different each other, m is an integer of 1~6, n is individually 0 or an integer of 1~4, R is a tetravalent radical having 2~27 carbon atoms and being selected from the group consisting of an aliphatic radical, alicyclic radical, monoaromatic radical, condensed polyaromatic radical and noncondensed aromatic radical connected to each other with a direct bond or a bridge member, and Ar is a divalent radical selected from the group consisting of

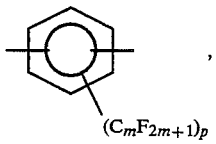

,

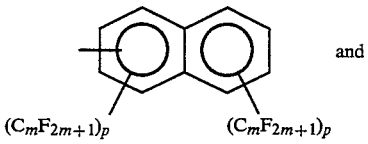

and

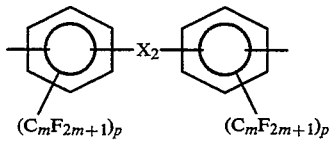

wherein $X_2$ is a direct bond or a divalent radical selected from the group consisting of —O—, —S—, —CO—, and —C(C$_3$)$_2$—, m is an integer of 1~6, and p is individually 0 or an integer of 1~4, or in integer of 1~4 when n is 0 in the formula (1).

That is, one aspect of the invention is a polyimide comprising a requisite structural unit having recurring structural units of the formula (1), and more specifically, can be a homopolymer having one of the recurring structural units of the formula (1) or can be a copolymer having two or more of the recurring structural units. The polyimide of the invention can also be a copolymer of recurring structural units of the formula (1) and other recurring structural units of polyimide in the range giving no adverse effect on the properties of polyimide of the invention. Further, the polyimide of the invention can have at the polymer chain end an aromatic ring which is essentially unsubstitued or substituted with a radical having no reactivity for amine and dicarboxylic anhydride. That is, the polyimide of the invention can be capped at the polymer chain end thereof with an aromatic dicarboxylic anhydride of the formula (15):

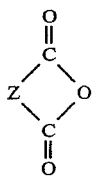

(15)

wherein Z is a divalent radical having 6~15 carbon atoms and being selected from the group consisting of a monoaromatic radical, condensed polyaromatic radical and noncondensed aromatic radical connected to each other with a direct bond or a bridge member, and/or aromatic monoamine of the formula (16):

$$Z_1-NH_2 \quad (16)$$

wherein $Z_1$ is a monovalent radical having 6~15 carbon atoms and being selected from the group consisting of a monoaromatic radical, condensed polyaromatic radical and noncondensed aromatic radical connected to each other with a direct bond or a bridge member, preferably by capping with phthalic anhydride or aniline.

The polyimide of the invention includes a polyimide homopolymer having one of the above recurring structural units, a polyimide copolymer having two or more of the above recurring structural units, a mixture of two or more of said polyimide homopolymer and/or said polyimide copolymers, a polyimide copolymer having the recurring structural units of the formula (1) and other recurring structural units which are comprised in a proportion giving no adverse effect on the essential properties of polyimide, and a mixture of polyimide having one or more recurring structural units of the formula (1) and polyimide having said other recurring structural units.

Consequently, when the polyimide of the invention is a polyimide copolymer having two or more recurring structural units of the formula(I) or a mixture of polyimides, the polyimide has two or more recurring structural units wherein one or more radicals selected from $X_1$, $X_2$, Ar and R in the formula (1) are different from each other.

The polyimide of the invention can be prepared by reacting the raw material monomers, fluorine containing aromatic diamine and aromatic tetracarboxylic dianhydride in the absence or presence of aromatic dicarboxylic anhydride and/or aromatic monoamine and by thermally or chemically imidizing the resulting polyamic acid.

The aromatic diamine which can be used for preparing the polyimide of the invention comprises one or more principal ingredients of the formula (13):

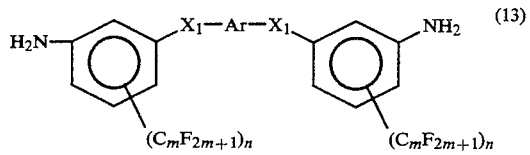

(13)

wherein $X_1$ is a direct bond or a divalent radical selected from the group consisting of —O—, —CO—, and —C(CH_3)_2—, two $X_1$ may be the same or different, m is an integer of 1~6, n is 0 or an integer of 1~4, Ar is a divalent radical selected from the group consisting of

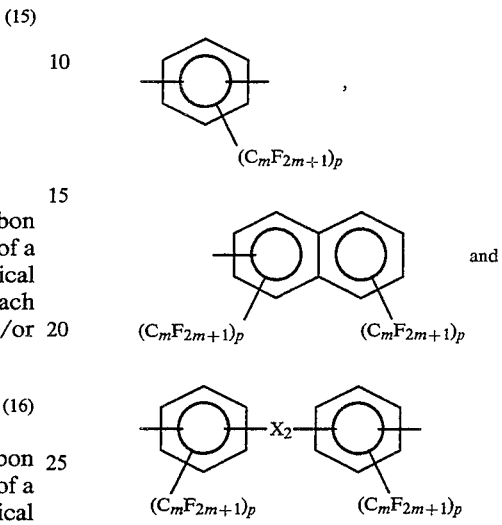

wherein $X_2$ is a direct bond or a divalent radical selected from the group consisting of —O—, —S—, —CO—, and —C(CH_3)_2—, m is an integer of 1~6, and p is individually 0 or an integer of 1~4 and an integer of 1~4 when n is 0 in the formula (13).

Preferred aromatic diamine has the formula (17):

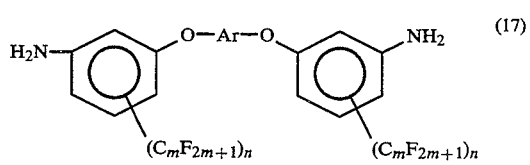

(17)

wherein Ar, m and n are the same as in the formula (13), and the formula (21):

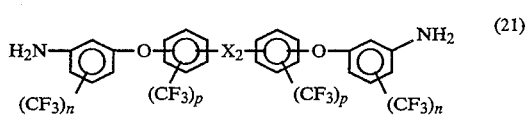

(21)

wherein $X_2$ is a direct bond or a divalent radical selected from the group consisting of —O—, —S—, —CO—, and —C(CH_3)_2—, and n and p are individually 0 or an integer of 1~4 and are not simultaneously 0.

More preferred aromatic diamines have the formulas (18), (19), (20) and (22):

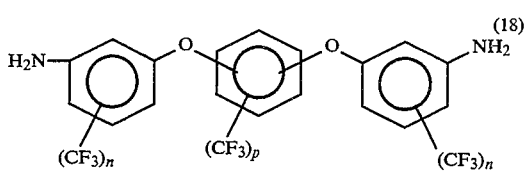

(18)

wherein n and p are 0 or an integer of 1 and are not simultaneously 0.

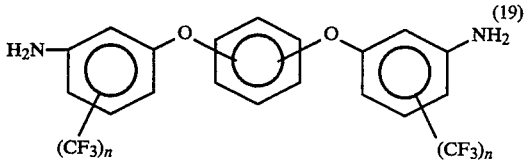

wherein n is an integer of 1~4.

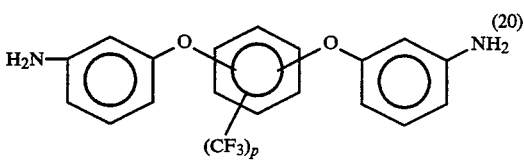

wherein p is an integer of 1-4.

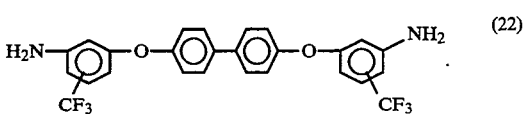

Exemplary aromatic diamines include following groups.

Group A which can be generally used are:
[Aromatic diamines of the formula (13) having 3 benzene rings];
3,3'-diamine-mono~dodeca-perfluoroalkylterphenyls,
mono~tetra-perfluoroalkyl-bis(3-amino-mono-~tetra-perfluoroalkylphenoxy)benzenes,
mono~tetra-perfluoroalkyl-bis(3-amino-mono~tetra-perfluoroalkylthiophenyl)benzenes,
mono~tetra-perfluoroalkyl-bis(3-amino-mono~tetra-perfluoroalkylbenzenes, and
mono~tetra-perfluoroalkyl-bis(3-amino-mono~tetra-perfluoroalkyl-α, a -dimethylbenzyl)benzenes,
[Aromatic diamines of the formula (13) having 4 benzene rings];
3,3''-diamino-di~hexadeca-perfluoroalkylquaterphenyls,
Di~octa-perfluoroalkyl-bis(3-amino-mono~tetra-perfluoroalkylphenoxy)biphenyls,
di~octa-perfluoroalkyl-bis(3-amino-mono~tetra-perfluoroalkylbenzoyl)biphenyls,
di~octa-perfluoroalkyl-bis(3-amino-mono~tetra-perfluoroalkyl-α,α-dimethylbenzyl)biphenyls,
bis(3-amino-di~octa-perfluoroalkylbiphenyl-yl)ethers,
di~octa-perfluoroalkyl-bis(3-amino-mono~tetra-perfluoroalkylphenoxy)diphenyl ethers, di~octa-perfluoroalkyl-bis(3-amino-mono~tetra-perfluoroalkylbenzoyl)diphenyl ethers, di~octa-perfluoroalkyl-bis(3-amino-mono~tetra-perfluoroalkyl-α,α-dimethylbenzyl)diphenyl ethers,
bis(3-amino-di~octa-perfluoroalkylbiphenyl-yl)thioethers,
di~octa-perfluoroalkyl-bis(3-amino-mono~tetra-perfluoroalkyphenoxy)diphenyl thioethers,
di~octa-perfluoroalkyl-bis(3-amino-mono~tetra-perfluoroalkylbenzoyl)diphenyl thioethers,
di~octa-perfluoroalkyl-bis(3-amino-mono~tetra-perfluoroalkyl-α,α-dimethylbenzyl)diphenyl thioethers,
bis(3-amino-di~octa-perfluoroalkylbiphenyl-yl)ketones,
di~octa-perfluoroalkyl-bis(3-amino-mono~tetra-perfluoroalkylphenoxy)benzophenones,
di~octa-perfluoroalkyl-bis(3-amino-mono~tetra-perfluoroalkylbenzoyl)benzophenones,
di~octa-perfluoroalkyl-bis(3-amino-mono~tetra-perfluoroalkyl-α,α-dimethylbenzyl)benzophenones,
2,2-bis[mono~tetra-perfluoroalkyl-bis(3-amino-mono~octa-perfluoroalkylbiphenyl-yl)phenyl]propanes,
2,2-bis[mono~tetra-perfluoroalkyl-bis(3-amino-mono~tetra-perfluoroalkylphenoxy)phenyl]propanes,
2,2-bis[mono~tetra-perfluoroalkyl-bis(3-amino-mono~tetra-perfluoroalkylbenzoyl)phenyl]propanes, and
2,2-bis[mono~tetra-perfluoroalkyl-bis(3-amino-mono~tetra-perfluoroalkyl-α,α-dimethylbenzyl)phenyl]propanes,
[Aromatic diamines of the formula (13) having 4 benzene rings and a naphthalene ring as the Ar radical];
di~hexa-perfluoroalkyl-bis(3'-amino-mono~tetra-perfluoroalkylphenyl)naphthalenes,
di~hexa-perfluoroalkyl-bis(3'-amino-mono~tetra-perfluoroalkylphenoxy)naphthalenes.
di~hexa-perfluoroalkyl-bis(3'-amino-mono~tetra-perfluoroalkylthiophenyl)naphthalenes,
di~hexa-perfluoroalkyl-bis(3'-amino-mono~tetra-perfluoroalkylbenzoyl)naphthalenes, and
di~hexa-perfluoroalkyl-bis(3'-amino-mono~tetra-perfluoroalkyl-α,α-dimethylbenzyl)naphthalenes.
Group B which can be preferably used are:
[Aromatic diamines of the formula (17) having 3 benzene rings];
mono~tetra-perfluoroalkyl-bis(3-amino-mono~tetra-perfluoroalkylphenoxy)benzenes,
[Aromatic diamines of the formula (17) having 4 benzene rings];
di~octa-perfluoroalkyl-bis(3-amino-mono~tetra-perfluoroalkylphenoxy)biphenyls,
di~octa-perfluoroalkyl-bis(3-amino-mono~tetra-perfluoroalkylphenoxy)diphenyl ethers,
di~octa-perfluoroalkylphenoxy diphenyl thioethers,
di~octa-perfluoroalkyl-bis(3-amino-mono~tetra-perfluoroalkylphenoxy)benzophenones, and
2,2-bis[mono~tetra-perfluoroalkyl-bis(3-amino-mono~tetra-perfluoroalkylphenoxy)phenyl]propanes,
[Aromatic diamines of the formula (17) having 4 benzene rings and a naphthalene ring as a divalent radical];
di~hexa-perfluoroalkyl-bis(3-amino-mono~tetra-perfluoroalkylphenoxy)naphthalenes.
Group C which can be more preferably used are:
[Aromatic diamines of the formula (18)];
mono~tetra-trifluoromethyl-bis(3-amino-mono~tetra-trifluoromethylphenoxy)benzenes,
[Aromatic diamines of the formula (19)];
bis(3-amino-mono~tetra-trifluoromethylphenoxy)benzenes, and mono~tetra-trifluoromethyl-bis(3-aminophenoxy)benzenes,
[Aromatic diamines of the formula (21)];
di~octa-trifluoromethyl-bis(3-amino-mono~tetra-trifluoromethylphenoxy)bisphenyls,
di~octa-trifluoromethyl-bis(3-amino-mono~tetra-trifluoromethylphenoxy)diphenyl ethers,
di~octa-trifluoromethyl-bis(3-amino-mono~tetra-trifluoromethylphenoxy)diphenyl thioethers,
di~octa-trifluoromethyl-bis(3-amino-mono~tetra-trifluoromethylphenoxy)diphenyl benzophenones, and
2,2-bis[di~tetra-trifluoromethyl(3-amino-mono~tetra trifluoromethylphenoxy)phenyl]propanes,

[Aromatic diamines of the formula (22)];

4,4'-bis[3-amino~tatra-trifluoromethylphenoxy)biphenyl.

Group D which can be most preferably used are:
1,3-bis(3-aminophenoxy)-4-trifluoromethylbenzene,
1,3-bis(3-aminophenoxy)-5-trifluoromethylbenzene,
1,3-bis(3-amino-5-trifluoromethylphenoxy)benzene,
1,4-bis(3-amino-5-trifluoromethylphenoxy)benzene,
1,3-bis(3-amino-5-trifluoromethylphenoxy)-5-trifluoromethylbenzene,
1,3-bis(3-amino-5-trifluoromethylphenoxy)-4-trifluoromethylbenzene, and
4,4'-bis(3-amino-5-trifluoromethylphenoxy)biphenyl.

These aromatic diamines can be used singly or as a mixture.

These fluorine containing aromatic diamines can be prepared by the following processes.

① A process for reacting a dihalogeno or dinitro compound of the formula (23):

Y—Ar—Y    (23)

wherein Y is a halogen atom or a nitro radical, and Ar is a divalent radical selected from the group consisting of

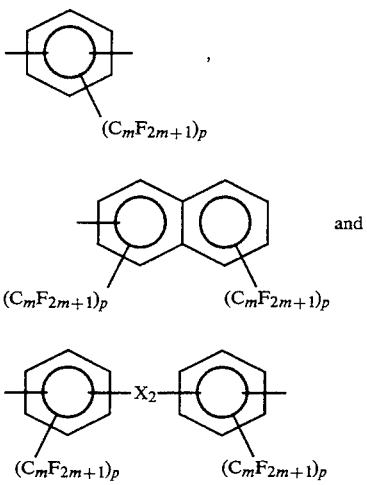

wherein $X_2$ is a direct bond or a divalent radical selected from the group consisting of direct bond, —O—, —S—, —CO— and —C(C$_3$)$_2$—, m is an integer of 1~6, and p is 0 or an integer of 1~4, with a m-nitrophenol derivative of the formula (24)

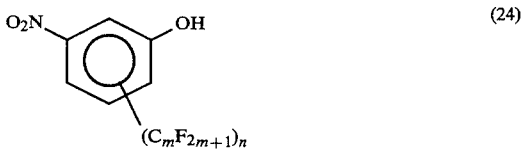

wherein m is an integer of 1~6, and n is 0 or an integer of 1~4 and is an integer of 1~4 when p is 0 in the formula (23), at 100°~250° C. in an aprotic polar solvent in the presence of a base and successively reducing the resultant aromatic dinitro compound.

② A process for reacting a dihydroxy compound of the formula (25):

HO—Ar—OH    (25)

wherein Ar is the same as in the formula (23), with a m-dinitro or m-nitrohalogeno compound of the formula (26):

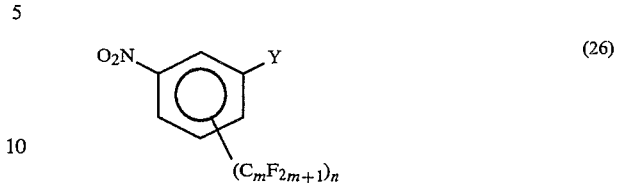

wherein Y is a halogen atom or a nitro radical, m is an integer of 1~6, and n is 0 or an integer of 1~4 and is an integer of 1~4 when p is 0 in the formula (25), at 100°~250° C. in an aprotic solvent in the presence of a base and successively reducing the resultant aromatic dinitro compound.

③ A process for reacting a dihalogeno compound or dinitro compound of the formula (23)

Y—Ar—Y    (23)

wherein Y and Ar are the same as above, with a m-aminophenol derivative of the formula (27):

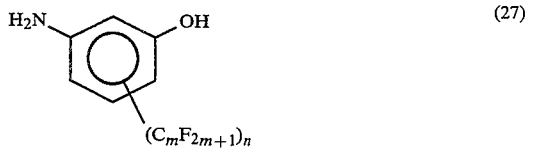

wherein m is an integer of 1~6, and n is 0 or an integer of 1~4 and an integer of 1~4 when p is 0 in the formula (23), at 10020~250° C. in an aprotic polar solvent in the presence of base.

These processes will hereinafter be illustrated in detail.

In the processes ①, 1,3-bis(3-aminophenoxy)-5-trifluoromethylbenzene is prepared in high yield by carrying out condensation of 3,5-dinitrobenzotrifluoride and m-nitrophenol in an aprotic polar solvent in the presence of a base to obtain 1,3-bis(3-nitrophenoxy)-5-trifluoromethylbenzene and successively reducing the same.

One of the raw materials, 3,5-dinitrobenzotrifluoride, can be obtained by reacting benzotrifluoride with mixed acid according to a known method as described in J. Am. Chem. Soc., 74, 3011-14. Two or more mols of m-nitrophenol is used in the reaction per mol of 3,5-dinitrobenzotrifluoride. Preferred amount is 2-2.5 mols in view of complex post-treatment and cost.

Bases which can be used are carbonate, hydrogen carbonate, hydroxide and alkoxide of alkali metals, and include, for example, potassium carbonate, potassium, hydrogen carbonate, potassium hydroxide, sodium carbonate, sodium hydroxide, sodium hydrogen carbonate, lithium carbonate, lithium hydroxide, sodium methoxide and potassium isopropoxide. The amount of these bases is one equivalent or more, preferably 1~2 equivalents to the hydroxyl group of the biphenol raw material.

Exemplary aprotic polar solvents used include N,N-dimethylformamide, N,N-diethylformamide, N,N-dimethylacetamide, N-methylpyrrolidone, 1,3-dimethyl-2-imidazolidinone, dimethyl sulfoxide and sulfolane. No particular limitation is imposed upon the amount of these solvents and the amount of 1–10 times by weight of the raw materials is usually sufficient.

Catalysts which can be used for accelerating the reaction are copper powder, copper compounds and phase transfer catalysts such as crown ether, polyethylene glycol, quaternary ammonium bases and quaternary phosphonium bases.

Reaction temperature is usually in the range of 80°–250° C., preferably in the range of 100°–200° C.

In a common method for carrying out the reaction, prescribed amounts of m-nitrophenol, the base and the aprotic polar solvent are charged to form an alkali metal salt of m-nitrophenol and then 3,5-dinitrobenzotrifluoride is added and reacted. Alternatively, all the materials including 3,5-dinitrobenzotrifluoride are previously charged at one time and the mixture is heated as intact to carry out the reaction. The method is not limited to these procedures and other methods can be suitably carried out.

When water is present in the reaction system, water is removed from the reaction system by ventilating with nitrogen gas during the reaction. However, a method generally carried out is to azeotropically distill off water by addition of a small amount of benzene, toluene, xylene and chlorobenzene.

End point of the reaction can be determined by a decrease of the raw materials according to thin layer chromatography or high performance liquid chromatography. After finishing the reaction, the reaction mixture is poured as intact or after concentration into water to obtain the crude dinitro compound. The crude compound can be purified by recrystallization from or sludging in a solvent.

The dinitro compound thus obtained is reduced to prepare the corresponding diamino compound. No particular restriction is placed upon the reduction method of the dinitro compound.

A method for reducing a nitro radical to an amino radical described, for example, in Shin Jikken Kagaku Koza, vol. 15, Oxidation and Reduction II, Published from Maruzen (1977), can be usually applied. Catalytic reduction is preferred in industry. Exemplary reducing catalysts which can be used include metal catalysts used generally for catalytic reduction, for example, nickel, palladium, platinum, rhodium, ruthenium, cobalt and copper. Palladium catalysts are preferred in industry.

These catalysts are generally used, though can be used in the state of metal, by being supported on the surface of a carrier such as carbon, barium sulfate, silica gel, alumina and cerite, or also used in the form of a Raney catalyst of nickel, cobalt or copper.

No particular limitation is put upon the amount of these catalysts. The amount is in the range of 0.01–10% by weight for the raw material dinitro compound, usually 2–8% by weight in the form of metal and 0.1–5% by weight when supported on the carrier.

No particular restriction is imposed upon the solvents used in the reduction as long as they are inactive for the reaction.

Preferred solvents include, for example, methanol, ethanol, isopropyl alcohol and other alcohols; ethylene glycol, propylene glycol and other glycols; ether, dioxane, tetrahydrofuran, methyl cellosolve and other ethers. Other solvents which can also be used in some cases are hexane, cyclohexane and other aliphatic hydrocarbons; benzene, toluene, xylene and other aromatic hydrocarbons; ethyl acetate, butyl acetate and other esters; dichloromethane, chloroform, carbon tetrachloride, 1,2-dichloroethane, 1,1,2-trichloroethane, tetrachloroethane and other halogenated hydrocarbons: and N,N-dimethylformamide. No particular limitation is placed upon the amount of these solvents. These solvents are used in an amount enough to suspend or completely dissolve the raw materials, that is, usually 0.5–10 times by weight for the weight of raw materials.

No particular limitation is placed on the reaction temperature. The reaction temperature is in the range of usually 20°–200° C., preferably 20°–100° C. Reaction pressure is in the range of atmospheric pressure to 50 atm.

Reducing reaction is usually carried out by suspending or dissolving the dinitro compound in a solvent, adding the catalyst and introducing hydrogen into the reaction system with stirring at a prescribed temperature. End point of the reaction can be determined by the amount of hydrogen, thin layer chromatography or high performance liquid chromatography. After finishing the reaction, the catalyst is removed by filtration and the solvent is distilled out of the filtrate to obtain the desired product.

In the process ②, 4,4'-bis(3-amino-5-trifluoromethylphenoxy) biphenyl, or 1,3- or 1,4-bis(3-amino-5-trifluoromethylphenoxy)benzene can be prepared in high yield by reacting 3,5-dinitrobenzotrifluoride and biphenol, or 3,5-dinitrobenzotrifluoride and resorcinol or hydroquinone in an aprotic solvent in the presence of the base and by reducing the resulting dinitro compound.

3,5-Dinitrobenzotrifluoride used in the reaction can be prepared by the process described in J. Am. Chem, Soc., 74, 3011–14, for example, by reaction of benzotrifluoride with a mixed acid. Biphenol, resorcinol and hydroquinone are available with ease from the market.

The amount of 3,5-dinitrobenzotrifluoride used in the reaction is 2 equivalents or more per equivalent of biphenol, resorcinol or hydroquinone. Preferred amount is 2–2.5 equivalents is view of complex post-treatment and cost.

Bases used are the same is in the case of the process ① and are carbonate, hydrogen carbonate, hydroxide and alkoxide of alkali metals. The amount of these bases is one equivalent or more, preferably 1–2 equivalents per equivalent of hydroxy radicals in the biphenol, resorcinol or hydroquinone as raw material.

Aprotic polar solvents which can be used are also the same as in the case of the process ①. No particular limitation is imposed upon the amount of solvents. The amount of 1–10 times by weight for the raw materials is sufficient to carry out the reaction.

Reaction temperature is usually in the range of 40°–250° C., preferably in the range of 80°–180° C. The same catalysts as used in the process ① can be used without any trouble for accelerating the reaction.

In a common reaction method, prescribed amounts of biphenol, resorcinol or hydroquinone, a base and a solvent are charged to form alkali metal salts of biphenol and resorcinol or hydroquinone, and then 3,5-dinitribenzotrifluoride is added and reacted. Alternatively, all the materials including 3,5-dinitrobenzotrifluoride are previously charged at one time and the mixture is heated as such to carry out the reaction. The method is not limited to these procedures and other methods can be be suitably carried out.

When water is present in the reaction system, water is removed from the reaction system by ventilating with nitrogen gas during the reaction. However, a method generally carried out is to azeotropically distill off water by addition of a small amount of benzene, toluene, xylene and chlorobenzene.

End point of the reaction can be determined by a decrease of the raw materials according to thin layer chromatography or high performance liquid chromatography. After finishing the reaction, the reaction mixture is poured as intact or after concentration into water to obtain the crude dinitro compound. The compound can be purified by recrystallization from or sludging in a solvent.

The dinitro compound thus obtained is reduced to prepare corresponding diamino compound. Reduction of the dinitro compound can be carried out by the same method as in the process ①.

In the reducing reaction, almost the same materials and means as in the process ① can be used on the catalyst, form and amount thereof, the solvent and amount thereof, and the addition of common phase transfer catalysts such as quaternary ammonium bases and quaternary phosphonium base in order to accelerate the reaction.

No particular limitation is placed on the reaction temperature. The reaction temperature is usually in the range of 20°–200° C., preferably in the range of 20°–100° C. Reaction pressure is in the range of atmospheric pressure to 50 atm.

Reducing reaction is usually carried out by suspending or dissolving the dinitro compound in a solvent, adding the catalyst and introducing hydrogen into the the reaction system with stirring at a prescribed temperature. End point of the reaction can be determined by the amount of hydrogen, thin layer chromatography or high performance liquid chromatography. After finishing the reaction, the catalyst is removed by filtration and the solvent is distilled out of the filtrate to obtain the desired product.

In the process ③,
3,5-bis(3-amino-5-trifluoromethylphenoxy)trifluoromethylbenzene and
2,4-bis(3-amino-5-trifluoromethylphenoxy)trifluoromethylbenzene can be prepared in high yield by reacting
3,5-dihalogenobenzotrifluoride,
3,5-dinitrobenzotrifluoride,
2,4-dihalogenobenzotrifluoride or
2,4-dinitrobenzotrifluoride(hereinafter referred to as the benzotrifluoride derivative) with 3-amino-5-trifluoromethylphenol in an aprotic polar solvent in the presence of a base.

One of the raw materials, the trifluoromethylbenzene derivative, can be obtained, for example, by reacting benzotrifluoride with a mixed acid according to a known method as described in J. Am. Chem, Soc., 74, 3011–14. 3-Amino-5-trifluoromethyl phenol can also be prepared by a know method described in J. Am. Chem, Soc., 1949, 3016–20.

Two or more equivalents of 3-amino-5-trifluoromethyl is used in the reaction for one equivalent of the trifluoroethylbenzene derivative.

Preferred amount is 2–2.5 equivalents in view of complex posttreatment and cost.

Bases which can be used include carbonate, hydrogen carbonate, hydroxide and alkoxide of alkali metals as in other processes. The amount of these bases is one equivalent or more, preferably 1–2 equivalents to the hydroxyl group of the biphenol raw material.

Aprotic polar solvents used are the same as in other processes. No particular limitation is imposed upon the amount of these solvents. The amount of 1~10 times by weight for the weight of raw materials is usually sufficient to carry out the reaction.

Reaction temperature is usually in the range of 40°–250° C., preferably in the range of 80°–180° C. Catalysts such as copper and copper derivatives, and phase transfer catalysts such as crown ether, polyethylene glycol, quaternary ammonium bases and quaternary phosphonium bases can be used for accelerating the reaction.

In a common method for carrying out the reaction, prescribed amounts of 3-amino-5-trifluoromethylphenol, the base and the solvent are charged to form an alkali metal salt of 3-amino-5-trifluoromethylphenol, and then the trifluoromethylbenzene derivative is added and reacted.

Alternatively, all the materials including the trifluoromethylbenzene derivative are previously charged at one time and the mixture is heated as intact to carry out the reaction. The method is not limited to these procedures and other methods can be suitably carried out.

When water is present in the reaction system, water is removed from the reaction system by ventilating with nitrogen gas during the reaction.

However a method generally carried out is to azeotropically distill off water by addition of a small amount of benzene, toluene, xylene and chlorobenzene.

End point of the reaction can be determined by decrease of the raw materials according to thin layer chromatography or high performance liquid chromatography. After finishing the reaction. The reaction mixture is poured as intact or after concentration into water to obtain the crude dinitro compound. The crude compound can be purified by recrystallization from or sludging in a solvent.

Reducing reaction is carried out by the same procedures as in the process ②. After finishing the reaction, the catalyst is removed from the reaction mixture by filtration, and the filtrate is concentrated to obtain the desired product.

Further, in the process ③,
1,3-bis(3-aminophenoxy)-4-trifluoromethylbenzene can be prepared by reacting 2,4-dichlorobenzotrifluoride with m-aminophenol in an aprotic polar solvent in the presence of a base. 2,4-Dichlorobenzotrifluoride and m-aminophenol are available with ease from the market.

The amount of m-aminophenol used in the reaction is 2 equivalents or more per equivalent of 2,4-dichlorobenzotrifluoride. Preferred amount is 2–2.5 equivalents in view of complex post-treatment and cost.

Bases and aprotic polar solvents which can be used in the reaction include the same as used in the process ②. The amount of these bases is one equivalent or more, preferably 1–2 equivalents per equivalent of m-aminophenol raw material. No particular limitation is placed on the amount of solvents. The amount of 1–10 times by weight for the weight of the raw materials is sufficient to carry out the reaction.

Catalysts such as copper powder and copper and copper compounds and phase transfer catalysts such as crown ether, polyetherglycol, quaternary ammonium bases and quaternary phosphonium bases can be used without any trouble to accelerate the reaction.

Reaction temperature is usually in the range of 40°–250° C., preferably in the range of 80°–180° C.

In a common reaction method, prescribed amounts of m-aminophenol, the base and the aprotic polar solvent are charged to form an alkali metal salt of m-aminophenol, and then 2,4-dichlorobenzotrifluoride is added and reacted. Alternatively, all the materials including 2,4-dichlorobenzotrifluoride are previously charged at one time and heated as intact to carry out the reaction. The method is not limited to these procedures and other methods can be suitably carried out.

When water is present in the reaction system, water is removed from the reaction system by ventilating with nitrogen gas during the reaction.

However, a method generally carried out is to azeotropically distill off water by addition of a small amount of benzene, toluene, xylene and chlorobenzene.

End point of the reaction can be determined by the same means as in the process ②.

Exemplary polyimides obtained by using these preferred aromatic diamines include those comprising a fundamental skeleton having recurring structural units of the formula (2):

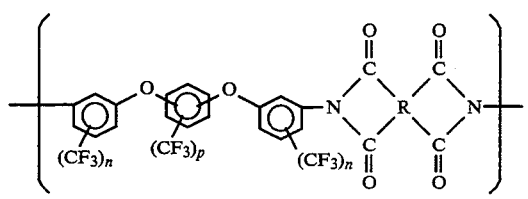

(2)

the formula (3):

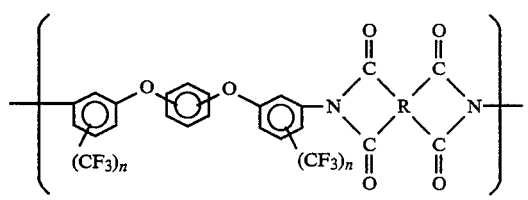

(3)

the formula (4):

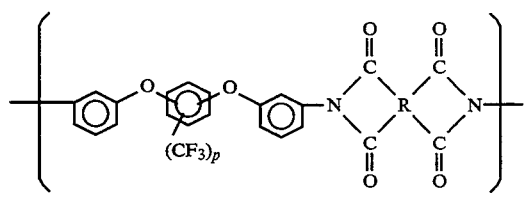

(4)

the formula (5):

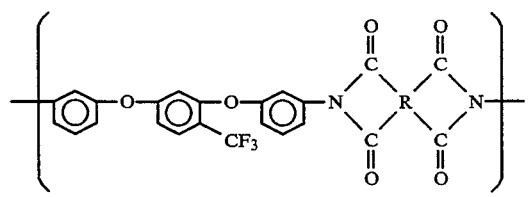

(5)

the formula (6):

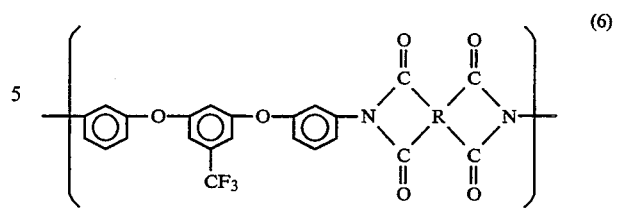

(6)

the formula (7):

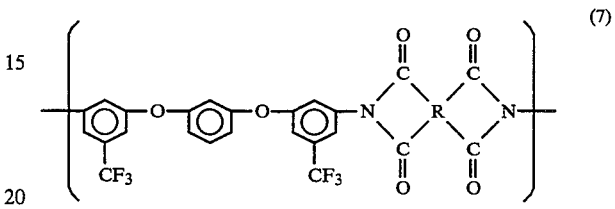

(7)

the formula (8):

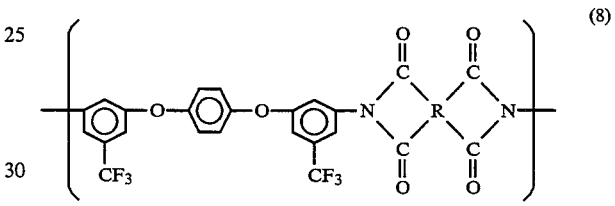

(8)

the formula (9):

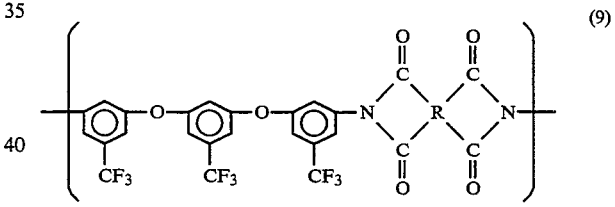

(9)

the formula (10):

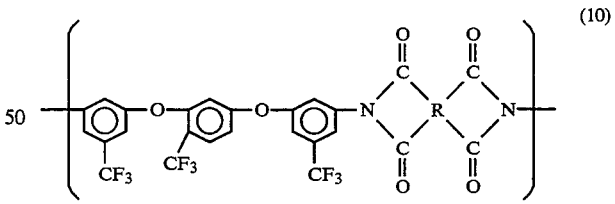

(10)

wherein n, p and R are the same as above.

The polyimide of the invention is prepared by using the above aromatic diamines for the requisite raw material monomer. Other aromatic diamines can be used in combination with these diamines so long as giving no adverse effect on the good properties of the polyimide.

Other aromatic diamines which can be used in combination include, for example, m-phenylenediamine, o-phenylenediamine, p-phenylenediamine, m-aminobenzylamine, p-aminobenzylamine,
4,4′-diaminodiphenyl ether,
3,3′-diaminodiphenyl ether,
3,4′-diaminodiphenyl ether,
bis(3-aminophenyl)sulfide, (3-aminophenyl)(4-aminophenyl)sulfide,
bis(4-aminophenyl)sulfide,
bis(3-aminophenyl)sulfoxide,
(3-aminophenyl)(4-aminophenyl)sulfoxide,
bis(3-aminophenyl)sulfone,
(3-aminophenyl)(4-aminophenyl)sulfone,
bis(4-aminophenyl)sulfone,
3,3'-diaminobenzophenone, 3,4'-diaminobenzophenone,
4,4'-diaminobenzophenone,
3,3'-diaminodiphenylmethane, 3,4'-diaminodiphenylmethane,
4,4'-diaminodiphenylmethane,
bis[4-(3-aminophenoxy)phenyl]methane,
bis[4-(4-aminophenoxy)phenyl]methane,
1,1-bis[4-(3-aminophenoxy)phenyl]ethane,
1,1-bis[4-(4-aminophenoxy)phenyl]ethane,
1,2-bis[4-(3-aminophenoxy)phenyl]ethane,
1,2-bis[4-(4-aminophenoxy)phenyl]ethane,
2,2-bis[4-(3-aminophenoxy)phenyl]propane,
2,2-bis[4-(4-aminophenoxy)phenyl]propane,
2,2-bis[4-(3-aminophenoxy)phenyl]butane,
2,2-bis[4-(3-aminophenoxy)phenyl]-1,1,1,3,3,3-hexafluoropropane, 2,2-bis[4-(4-aminophenoxy)phenyl]-1,1,1,3,3,3-hexafluoropropane,
1,3-bis(3-aminophenoxy)benzene,
1,3-bis(4-aminophenoxy)benzene,
1,4-bis(3-aminophenoxy)benzene,
1,4-bis(4-aminophenoxy)benzene,
1,3-bis(3-aminobenzoyl)benzene,
1,3-bis(4-aminobenzoyl)benzene,
1,4-bis(3-aminobenzoyl)benzene,
1,4-bis(4-aminobenzoyl)benzene,
1,3-bis(3-amino-α,α-dimethybenzyl)benzene,
1,3-bis(4-amino-α,α-dimethybenzyl)benzene,
1,4-bis(3-amino-α,α-dimethybenzyl)benzene,
1,4-bis(4-amino-α,α-dimethybenzyl)benzene,
4,4'-bis(3-aminophenoxy)biphenyl,
4,4'-bis(4-aminophenoxy)biphenyl,
bis[4-(3-aminophenoxy)phenyl]ketone,
bis[4-(4-aminophenoxy)phenyl]ketone,
bis[4-(3-aminophenoxy)phenyl]sulfide
bis[4-(4-aminophenoxy)phenyl]sulfide
bis[4-(3-aminophenoxy)phenyl]sulfoxide,
bis[4-(4-aminophenoxy)phenyl]sulfoxide,
bis[4-(3-aminophenoxy)phenyl]sulfone,
bis[4-(4-aminophenoxy)phenyl]sulfone,
bis[4-(3-aminophenoxy)phenyl]ether,
bis[4-(4-aminophenoxy)phenyl]ether,
1,4-bis[4-(3-aminophenoxy)benzoyl]benzene,
1,3-bis[4-(3-aminophenoxy)benzoyl]benzene,
4,4'-bis[3-(4-aminophenoxy)benzoyl]diphenyl ether,
4,4'-bis[3-(3-aminophenoxy)benzoyl]diphenyl ether,
4,4'-bis[4-(4-amino-α,α-dimethybenzyl)phenoxy]benzophenone,
4,4'-bis[4-(4-amino-α,α-dimethybenzyl)phenoxy]diphenyl sulfone,
bis[4-{4-(4-aminophenoxy) phenoxy}phenyl]sulfone,
1,4-bis[4-(4-aminophenoxy)-α,α-dimethybenzyl]benzene,
1,4-bis[4-(3-aminophenoxy)-α,α-dimethybenzyl]benzene,
1,3-bis[4-(4-aminophenoxy)-α,α-dimethybenzyl]benzene,
1,3-bis[4-(3-aminophenoxy)-α,α-dimethybenzyl]benzene,
3,3'-diamino-4,4'-difluorobenzophenone,
3,3'-diamino-5,5'-bis(trifluoromethyl)diphenyl ether, and
4,4'diamino-5,5'-bis (trifluoromethyl)diphenyl ether.

These aromatic diamines can be used singly or as a mixture.

Aromatic tetracarboxylic dianhydride which can be used in the invention is one or more of compounds of the formula (14)

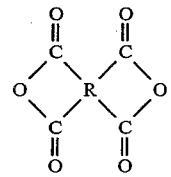 (14)

wherein R is a tetravalent radical having 2–27 carbon atoms and being selected from the group consisting of an aliphatic radical, alicyclic radical, monoaromatic radical, condensed polyaromatic radical and noncondensed aromatic radical connected to each other with a direct bond or a bridge member.

In the aromatic tetracarboxylic dianhydride of the formula (14), R is specifically a tetravalent radical selected from the group consisting of an aliphatic radical having 2–10 carbon atoms, alicyclic radical having 4–10 carbon atoms, monoaromatic radical of the formula (a):

 (a)

condensed polyaromatic radical of the formula (b):

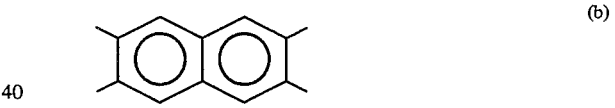 (b)

and noncondensed aromatic radical being connected to each other with a direct bond or a bridge member and having the formula (c):

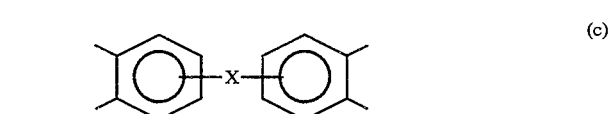 (c)

wherein X is a direct bond, —CO—, —O—, —S—, —SO$_2$—, —CH$_2$—, —C(C$_3$)$_2$—, —C(CF$_3$)$_2$—,

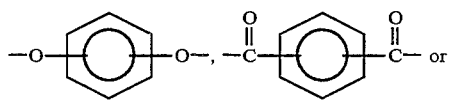 or

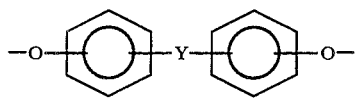

wherein Y is a direct bond, —CO—, —O—, —S—, —SO$_2$—, —CH$_2$—, —C(CH$_3$)$_2$— or —C(CF$_3$)$_2$—.

Exemplary tetracarboxylic dianhydrides of the formula (4) which can be used in the invention include, ethylenetetracarboxylic dianhydride,
cyclopentanetetracarboxylic dianhydride,
pyromellitic dianhydride,
3,3',4,4'-benzophenonetetracarboxylic dianhydride,
2,2',3,3'-benzophenonetetracarboxylic dianhydride,
3,3',4,4'-biphenyltetracarboxylic dianhydride,
2,2',3,3'-biphenyltetracarboxylic dianhydride,
2,2-bis(3,4-dicarboxyphenyl)propane dianhydride,
2,2-bis(2,3-dicarboxyphenyl)propane dianhydride,
bis(3,4-dicarboxyphenyl)ether dianhydride,
bis(3,4-dicarboxyphenyl)sulfone dianhydride,
1,1-bis(2,3-dicarboxyphenyl)ethane dianhydride,
bis(2,3-dicarboxyphenyl)methane dianhydride,
bis(3,4-dicarboxyphenyl)methane dianhydride,
2,2-bis(3,4-dicarboxyphenyl)-1,1,1,3,3,3-hexafluoropropane dianhydride,
2,2-bis(2,3-dicarboxyphenyl)-1,1,1,3,3,3-hexafluoropropane dianhydride,
1,3-bis[(3,4-dicarboxy)benzoyl]benzene dianhydride,
1,3-bis[(3,4-dicarboxy)benzoyl]benzene dianhydride,
2,2-bis[4{4-(1,2-dicarboxy)benzoyl}phenyl]propane dianhydride,
2,2-bis[4{3-(1,2-dicarboxy)phenoxy}phenyl]propane dianhydride,
bis[4-{4-(1,2-dicarboxy)phenoxy}phenyl]ketone dianhydride,
bis[4-{3-(1,2-dicarboxy)phenoxy}phenyl]ketone dianhydride,
4,4'-bis[4-(1,2-dicarboxy)phenoxy]biphenyl dianhydride,
4,4'-bis[3-(1,2-dicarboxy)phenoxy]biphenyl dianhydride,
bis[4-{4-(1,2-dicarboxy)phenoxy}phenyl]ketone dianhydride,
bis[4-{3-(1,2-dicarboxy)phenoxy}phenyl]ketone dianhydride,
bis[4-{4-(1,2-dicarboxy)phenoxy}phenyl]sulfone dianhydride,
bis[4-{3-(1,2-dicarboxy)phenoxy}phenyl]sulfone dianhydride,
bis[4-{4-(1,2-dicarboxy)phenoxy}phenyl]sulfide dianhydride,
bis[4-{3-(1,2-dicarboxy)phenoxy}phenyl]sulfide dianhydride,
2,2-bis[4-{4-(1,2-dicarboxy)phenoxy}phenyl]-1,1,1,3,3,3-hexafluoropropane dianhydride,
2,2-bis[4-(3-(1,2-dicarboxy)phenoxy }phenyl]-1,1,1,3,3,3-hexafluoropropane dianhydride,
2,3,6,7-naphthalenetetracarboxylic dianhydride,
1,4,5,8-naphthalenetetracarboxylic dianhydride,
1,2,5,6-naphthalenetetracarboxylic dianhydride,
1,2,3,4-benzenetetracarboxylic dianhydride,
3,4,9,10-perylenetetracarboxylic dianhydride,
2,3,6,7-anthracenetetracarboxylic dianhydride, and
1,2,7,8-phenanthrenetetracarboxylic dianhydride.

These dianhydrides can be used singly or as a mixture.

The polyimide of the invention prepared by using the above aromatic diamine and aromatic tetracarboxylic dianhydride as monomer components comprises a requisite structural unit primarily having recurring structural units of the formula (1). That is, the invention includes polyimide which is derived from a selected aromatic diamine and a selected aromatic tetracarboxylic dianhydride in the above enumerated raw materials of the invention and has recurring structural units of the formula (1)~(12), a polyimide copolymer which is derived from one or more selected aromatic diamines and one or more selected aromatic tetracarboxylic dianhydrides (both one, exclusive) in the above enumerated raw materials of the invention, and a polyimide copolymer which is derived from one or more selected aromatic diamines and one or more selected aromatic tetracarboxylic dianhydride in the above enumerated raw materials of the invention in combination with other diamines added in the range of giving no adverse effect on the properties of resulting polyimide.

The invention also includes capped polyimides having at the polymer chain end thereof an aromatic ring which is unsubstituted or substituted with a radical having no reactivity for amine and dicarboxylic anhydride.

Further, the invention includes composition of these polyimides. Compositions have better properties than polyimides as such in some cases.

The capped polyimide having at the polymer chain end thereof an aromatic ring unsubstituted or substituted with a radical having no reactivity for amine and dicarboxylic anhydride can be obtained by capping with aromatic dicarboxylic anhydride of the formula (15):

wherein Z is the same as above, and/or aromatic monoamine of the formula (16):

$$Z_1-NH_2 \qquad (16)$$

wherein $Z_1$ is the same as above, preferably phthalic anhydride and/or aniline.

The capped polyimide can be prepared by reacting an aromatic diamine component with an aromatic tetracarboxylic dianhydride component in the presence of the aromatic dicarboxylic anhydride of the formula (15) and/or the aromatic monoamine of the formula (16) and thermally or chemically imidizing the resulting polyamic acid.

Exemplary aromatic dicarboxylic anhydrides of the formula (15) include
2,3-benzophenonedicarboxylic anhydride,
3,4-benzophenonedicarboxylic anhydride,
2,3-dicarboxyphenylphenyl ether anhydride,
3,4-dicarboxyphenyl phenyl ether anhydride,
2,3-biphenyldicarboxylic anhydride,
3,4-biphenyldicarboxylic anhydride,
2,3-dicarboxyphenyl phenyl sulfone anhydride,
3,4-dicarboxyphenyl phenyl sulfone anhydride,
2,3-dicarboxyphenyl phenyl sulfide anhydride,
3,4-dicarboxyphenyl phenyl sulfide anhydride,
1,2-naphthalenedicarboxylic anhydride,
2,3-naphthalenedicarboxylic anhydride,
1,8-naphthalenedicarboxylic anhydride,
1,2-anthracenedicarboxylic anhydride,
2,3-anthracenedicarboxylic anhydride, and
1,9-anthracenedicarboxylic anhydride.

These dicarboxylic anhydrides can be substituted with a radical having no reactivity for amine and dicarboxylic anhydride.

Phthalic anhydride is most preferred in these dicarboxylic anhydrides in view of properties of resulting polyimide and practical use. Polyimide prepared in the presence of phthalic anhydride has excellent heat stability in high temperature processing has dominant chemical resistance and is very useful for a material of space and aeronautic instruments and electric and electronic devices. A portion of phthalic anhydride can be replaced with other dicarboxylic anhydrides in the range giving no adverse effect on the good properties of polyimide.

The amount of dicarboxylic anhydride is 0.001–1.0 mol per mol of the aromatic diamine component. An amount less than 0.001 mol leads to viscosity increase in the high temperature processing and causes reduction of processability. On the other hand, an amount exceeding 1.0 mol lowers mechanical strengths of the product. Thus, the preferred range is 0.001–0.5 mol.

Aromatic monoamines which can be used include, for example, o-toluidine, m-toluidine, p-toluidine, 2,3-xylidine, 2,6-xylidine, 3,4-xylidine, 3,5-xylidine, o-chloroaniline, m-chloroaniline, p-chloroaniline, o-bromoaniline, m-bromoaniline, p-bromoaniline, m-nitroaniline, p-nitroaniline, o-aminophenol, m-aminophenol, p-aminophenol, o-anisidine, m-anisidine, p-anisidine, o-phenetidine, m-phenetidine, p-phenetidine, o-aminobenzaldehyde, m-aminobenzaldehyde, p-aminobenzaldehyde, o-aminobenzonitrile, m-aminobenzonitrile, p-aminobenzonitrile, 2-aminobiphenyl, 3-aminobiphenyl, 4-aminobiphenyl, 2-aminophenyl phenyl ether, 3-aminophenyl phenyl ether, 4-aminophenyl phenyl ether, 2-aminobenzophenone, 3-aminobenzophenone, 4-aminobenzophenone, 2-aminophenyl phenyl sulfide, 3-aminophenyl phenyl sulfide, 4-aminophenyl phenyl sulfide, 2-aminophenyl phenyl sulfone, 3-aminophenyl phenyl sulfone, 4-aminophenyl phenyl sulfone, α-naphthylamine, β-naphthylamine, 1-amino-2-naphthol, 2-amino-1-naphthol, 4-amino-1-naphthol, 5-amino-1-naphthol, 5-amino-2-naphthol, 7-amino-2-naphthol, 8-amino-1-naphthol, 8-amino-2-naphthol, 1-aminoanthracene, 2-aminoanthracene and 9-aminoanthracene. These aromatic monoamines can be substituted with a radical having no reacting for amine and dicarboxylic anhydride.

The amount of aromatic monoamine is 0.001~1.0 mol per mol of the aromatic tetracarboxylic dianhydride component. An amount less than 0.001 mol leads to viscosity increase in the high temperature processing and causes reduction of processability. On the other hand, an amount exceeding 1.0 mole lowers mechanical strengths of the product. Thus, the preferred range is 0.001~0.5 mol.

Consequently, preparation of capped polyimide of the invention which is terminated with an unsubstituted or substituted aromatic ring is carried out by using 0.9–1.0 mol of aromatic diamine and 0.001–1.0 mol of dicarboxylic anhydride or aromatic monoamine per mol of tetracarboxylic dianhydride.

In the preparation of polyimide, the molar ratio of tetracarboxylic dianhydride to aromatic diamine is usually controlled in order to adjust molecular weight of formed polyimide. In order to obtain polyimide having good melt-flowability in the process of the invention, the molar ratio of aromatic diamine to tetracarboxylic dianhydride is suitably in the range of 0.9–1.0.

Any process for preparing polyimide including known processes can be applied to the preparation of polyimide in the invention. Particularly preferred process is to carry out the reaction in an organic solvent.

Exemplary solvents which can be used for the reaction include N,N-dimethylformamide, N,N-dimethylacetamide, N,N-diethylacetamide, N,N-dimethylmethoxyacetamide, N-methyl-2-pyrrolidone, 1,3-dimethyl-2-imidazolidinone, N-methylcaprolactam, 1,2-dimethoxyethane, bis(2-methoxyethyl)ether, 1,2-bis(2-methoxyethoxy)ethane, bis[2-(2-methoxyethoxy)ethyl]ether, tetrahydroxyfluoran, 1,3-dioxane, 1,4-dioxane, pyridine, picoline, dimethyl sulfoxide, dimethyl sulfone, tetramethylurea, hexamethylphosphoramide, phenol, o-cresol, m-cresol, p-cresol, m-cresylic acid, p-chlorophenol and anisol. These organic solvents can be used singly or as a mixture.

In the process of the invention, the reaction is carried out by the addition of aromatic diamine, aromatic tetracarboxylic dianhydride and aromatic dicarboxylic anhydride or aromatic monoamine to the organic solvent according to the following procedures.

(A) After reacting aromatic tetracarboxylic dianhydride with aromatic diamine, aromatic dicarboxylic anhydride or aromatic monoamine is added to continue the reaction.

(B) After reacting aromatic diamine with aromatic dicarboxylic anhydride, aromatic tetracarboxylic dianhydride is added to continue the reaction.

(C) After reacting aromatic tetracarboxylic dianhydride with aromatic monoamine, aromatic diamine is added to continue the reaction.

(D) Aromatic tetracarboxlic dianhydride, aromatic diamine and aromatic dicarboxylic anhydride or aromatic monoamine are added at one time and the reaction is carried out.

Any of the above addition procedures can be conducted.

Reaction temperature is usually 250° C. or less, preferably 50° C. or less. No particular limitation is imposed upon the reaction pressure. Atmospheric pressure is satisfactory for carrying out the reaction. Reaction time differs depending upon the tetracarboxylic dianhydride, solvent and reaction temperature and sufficient time for carrying out the reaction is usually 4–24 hours.

Further, polyamic acid thus obtained is thermally imidized by heating at 100°–400° C. or chemically imidized by using an imidizing agent such as acetic anhydride to give polyimide having recurring structural units corresponding to those of polyamic acid.

Alternatively, formation and imidization of the polyamic acid precursor can be simultaneously carried out to obtain polyimide of the invention by suspending or dissolving in the organic solvent aromatic tetracarboxylic dianhydride, aromatic diamine and optionally aromatic dicarboxylic anhydride or aromatic monoamine in the case of capping the polyimide chain end and successively heating the resulting mixture.

The polyamic acid precursor of the polyimide of the invention has an inherent viscosity of 0.01–3.0 dl/g at 35° C. in a dimethylacetamide solution at a concentration of 0.5 g/dl. The polyimide has an inherent viscosity of 0.01–3.0 dl/g at 35° C. at a concentration of 0.5 g/dl in a solvent mixture consisting of 9 parts by weight of p-chlorophenol and 1 part by weight of phenol.

Polyimide film of the invention can be prepared by casting a solution of the polyamic acid precursor on a glass plate and carrying out thermal imidization or by directly hot-pressing polyimide powder.

That is, films and powder of polyimide can be prepared by known methods.

In the case of melt-processing the polyimide of the invention, other thermoplastic resins can be blended in a suitable amount depending upon the object for use so long as giving no adverse effect on the good properties of polyimides.

Thermoplastic resin which can be blended include, for example, polyethylene, polypropylene, polycarbonate, polyarylate, polyamide, polysulfone, polyether sulfone, polyether ketone, polyphenylene sulfide, polyamideimide, polyetherimide, modified polyphenylene oxide and other kinds of polyimides.

Fillers which are used for common resin compositions can be added in the range not impairing the object of the invention. Exemplary fillers include graphite, carborundum, silica powder, molybdenum disulfide, fluoro resin and other wear resistance improvers; glass fiber, carbon fiber and other reinforcements; antimony trioxide, magnesium carbonate, calcium carbonate and other flame retardance improvers; clay, mica and other electrical property improvers; asbestos, silica, graphite and other tracking resistance improvers; barium sulfide, silica, calcium metasilicate and other acid resistance improvers; iron powder, zinc powder, aluminum powder, copper powder and other thermal conductivity improvers; and other miscellaneous materials such as glass beads, glass balloons, talc, diatomaceous earth, alumina, silicate balloons, hydrated alumina, metal oxides and colorants.

The invention will hereinafter be illustrated in detail by way of examples. However, these examples are not to be construed to limit the scope of the invention.

EXAMPLE 1

To a four necked flask equipped with a thermometer, reflux condenser and stirrer, 250 ml of N,N-dimethylformamide(DMF), 30 ml of toluene, 30 g (0.127 mol) of 3,5-dinitrobenzotrifluoride, 11.83 g (0.0635 mol) of 4,4'-dihydroxybiphenyl and 17.56 g (0.127 mol) of potassium carbonate were charged. The mixture was heated to 110° C. with stirring and aged for 4 hours at 110° C. After finishing the reaction, the reaction mixture was cooled to 80° C. and filtered to remove inorganic salts. The filtrate was mixed with 30 ml of water and cooled to room temperature to precipitate the desired product.

Precipitated crystals were filtered and sludged with methanol to obtain 34.4g (96% yield) of desired 4,4'-bis(3-nitro-5-trifluoromethylphenoxy) biphenyl having a melting point of 148.24~149.3.

| Elemental analysis ($C_{26}H_{14}N_2O_6F_6$) | | | | |
| --- | --- | --- | --- | --- |
| | C | H | N | F |
| Calculated (%) | 55.33 | 2.50 | 4.96 | 20.20 |
| Found (%) | 55.14 | 2.62 | 4.90 | 20.08 |

$^1$H-NMR δ (CDCl$_3$, ppm)
7.19 ((1)-4H, d)
7.63 ((2)-2H, s)
7.68 ((3)-4H, d)
7.99 ((4)-2H, s)
8.19 ((5)-2H, s)
wherein (1)~(5) indicate positions on the following formula.

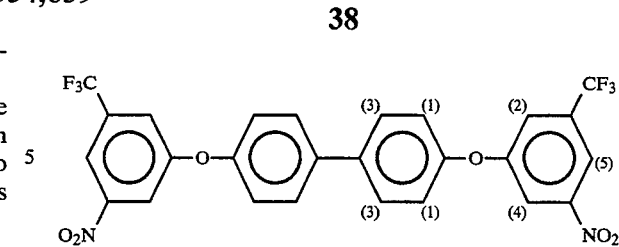

EXAMPLE 2

To a reducing apparatus equipped with a thermometer, reflux condenser and stirrer, 33 g (0.0585 mol) of 4,4'-bis(3-nitro-5-trifluoromethylphenoxy) biphenyl, 100 ml of methyl cellosolve and 1.7 g of 5%-Pd/c having a moisture content of 50% were charged and reacted in a hydrogen atmosphere at 70°~80° C. for 4 hours. After finishing the reaction, the catalyst was filtered off. The filtrate was concentrated under reduced pressure to obtain 4,4'-bis(3-amino-5-trifluoromethylphenoxy) biphenyl as light yellow crystals.

The product was 34.4 g (96% yield) and had a melting point of 130.4°~132.9° C.

| Elemental analysis ($C_{26}H_{18}N_2O_2F_6$) | | | | |
| --- | --- | --- | --- | --- |
| | C | H | N | F |
| Calculated (%) | 61.91 | 3.60 | 5.55 | 22.60 |
| Found (%) | 62.02 | 3.63 | 5.31 | 22.41 |

$^1$H-NMR δ (CDCl$_3$, ppm)
3.86 ((1)-4H, s )
6.45 ((2)-2H, m )
6.63 ((3)-4H, s )
7.08 ((4)-4H, m )
7.59 ((5)-4H, m )
wherein (1)~(5) indicate positions on the following formula.

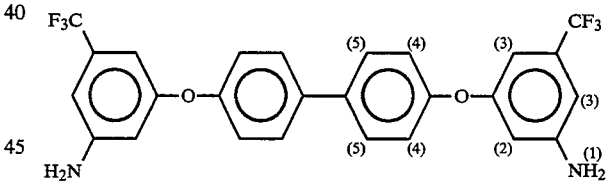

EXAMPLE 3

To a four necked flask equipped with a thermometer, reflux condenser and stirrer, 150 g of N,N-dimethylimidazolidinone (DMI), 30 g of o-xylene, 37 g (0.172 mol) of 2,4-dichlorobenzotrifluoride, 39.4 g (0.361 mol) of m-aminophenol and 25.5 g (0.185 mol) of potassium carbonate were charged. The mixture was heated to 200° C. with stirring and reacted for 30 hours at 200° C. At the end of reaction, 1,3-bis(3-aminophenoxy)-4-trifluoromethylbenzene (APTFB) had purity of 83% by HPLC.

The reaction mixture was cooled after finishing the reaction and filtered to remove inorganic salts. DMI was distilled off from the filtrate under reduced pressure. The residue was dissolved by adding 100 g of isopropanol (IPA) and 200 g of 36% hydrochloric acid was added to the resultant solution to precipitate the desired product in the form of hydrochloride.

APTFB hydrochloride thus obtained was suspended in a mixture of 150 g of water and 200 g of 1,2- dichloroethane (EDC), neutralized with a 28% aqueous ammonia solution and separated. The EDC layer was washed with water. Solvent was distilled off from the EDC solution to obtain desired APTFB as a red brown viscous liquid. The product was 35.6 g (57.4% yield).

¹H-NMR δ (CDCl₃, ppm)
3.53 (4H (1), s)
6.26~6.45 (6H (2), m)
6.61~6.71 (2H (3), m)
6.99~7.24 (2H (4), m)
7.53 (1H (5), d)

wherein (1)~(5) indicate positions on the following formula.

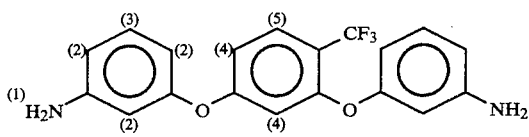

| Elemental analysis (C₁₉H₁₅N₂O₂F₃) | | | |
|---|---|---|---|
| | C | H | N | F |
| Calculated (%) | 63.33 | 4.20 | 7.77 | 15.82 |
| Found (%) | 63.30 | 4.24 | 7.81 | 15.77 |

EXAMPLE 4

To a four necked flask equipped with a thermometer, reflux condenser and stirrer, 250 g of N,N-dimethylformamide(DMF), 25 g of toluene, 40 g (0,169 mol) of 3,5-dinitrobenzotrifluoride, 48.3 g (0.347 mol) of m-nitrophenol and 28 g (0,203 mol) of potassium carbonate were charged.

The mixture was heated to 150° C. and reacted for 25 hours at 150° C. At the end of reaction, 1,3-bis(3-nitrophenoxy)-5-trifluoromethylbenzene had purity of 80% by HPLC. After finishing the reaction, the reaction mixture was cooled to 90° C. and filtered to remove inorganic salt. The filtrate was mixed with 190 ml of water and cooled to room temperature. Precipitated crystals were filtered and recrystallized from methyl cellosolve to obtain 1,3-bis(3-nitrophenoxy)-5-trifluoromethylbenzene as light yellow solid.

The product was 54.9 g (77% yield) and had a melting point of 117.6°~118.5° C.

| Elemental analysis (C₁₉H₁₁N₂O₆F₃) | | | |
|---|---|---|---|
| | C | H | N | F |
| Calculated (%) | 54.30 | 2.64 | 6.67 | 13.56 |
| Found (%) | 54.14 | 2.62 | 6.59 | 13.51 |

To a reducing apparatus equipped with a thermometer, reflux condenser and stirrer, 55 g (0.131 mol) of 1,3-bis(3-nitrophenoxy)-5-trifluoromethylbenzene, 150 g of methyl cellosolve and 5 g of 5% Pd/c having a moisture content of 50% were charged and reacted in a hydrogen atmosphere at 70°~80° C. for 4 hours. After finishing the reaction, the catalyst was filtered off. The filtrate was heated to 90° C., mixed with 140 g of water and cooled to room temperature. The precipitated crystals were filtered and dried under reduced pressure to obtain 1,3-bis(3-aminophenoxy)-5-trifluoromethyl benzene as colorless solid. The product was 41 g (87% yield) and had a melting point of 98.0°~98.6° C.

¹H-NMR δ (CDCl₃, ppm)
3.56 (4H (1), s)
6.31~6.51 (6H (2), m)
6.81~7.24 (5H (3), m)

wherein (1)~(3) indicate positions on the following formula.

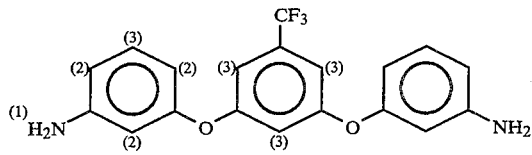

| Elemental analysis (C₁₉H₁₅N₂O₂F₃) | | | |
|---|---|---|---|
| | C | H | N | F |
| Calculated (%) | 63.33 | 4.20 | 7.77 | 15.82 |
| Found (%) | 63.38 | 4.26 | 7.75 | 15.79 |

EXAMPLE 5

To a four necked flask equipped with a thermometer, reflux condenser and stirrer, 500 ml of DMF, 50 ml of toluene, 80 g (0.339 mol) of 3,5-dinitrobenzotrifluoride, 18.7 g (0.169 mol) of resorcinol and 28.1 g (0.203 mol) of potassium carbonate were charged. The mixture was heated to 110° C. with stirring and aged for 5 hours at 110° C. After finishing the reaction, the reaction mixture was cooled to room temperature and filtered to remove inorganic salts. The filtrate was concentrated to obtain the desired 1,3-bis(3-nitro-5-trifluoromethylphenoxy)benzene. The product was 72 g (87% yield).

| Elemental analysis (C₂₀H₁₀N₂O₆F₆) | | | |
|---|---|---|---|
| | C | H | N | F |
| Calculated (%) | 49.20 | 2.06 | 5.74 | 23.34 |
| Found (%) | 49.17 | 2.10 | 5.78 | 23.29 |

¹H-NMR δ (CDCl₃, ppm)
6.82~6.96 (2H (1), m)
7.02~7.04 (2H (2), m)
7.45~7.54 (1H (3), m)
7.61~7.63 (1H (4), m)
7.98~8.03 (2H (5), m)
8.23~8.35 (2H (6), m)

wherein (1)~(6) indicate positions on the following formula.

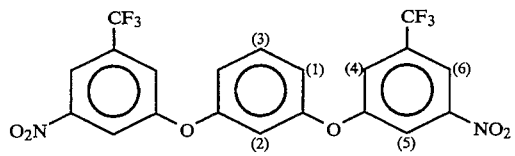

To a reducing apparatus equipped with a thermometer, reflux condenser and stirrer, 72 g (0.147 mol) of 1,3-bis(3-nitro-5-trifluoromethylphenoxy)benzene, 500 ml of isopropyl alcohol and 7.2 g of 5% Pd/c having a moisture content of 50% were charged and reacted in a hydrogen atmosphere at 50° C. for 5 hours. After finishing the reaction, the catalyst was filtered off. The filtrate was concentrated under reduced pressure. The residue was dissolved in 200 g of isopropyl alcohol.

The resulting solution was mixed with 400 g of 36% hydrochloric acid to precipitate the desired product in the form of hydrochloride. The hydrochloride thus obtained was suspended in a mixture of 150 g of water and 200 g of 1,2-dichloroethane(EDC) and neutralized with a 28% aqueous ammonia solution. The EDC layer was separated, washed with water, and the solvent distilled off to obtain 1,3-bis(3-amino-5-trifluoromethylphenoxy) benzene as a brown viscous liquid. The product was 33.8 g (53.7% yield).

| Elemental analysis ($C_{20}H_{14}N_2O_6F_6$) | | | |
| --- | --- | --- | --- |
| C | H | N | F |
| Calculated (%) 56.08 | 3.29 | 6.54 | 26.61 |
| Found (%) 56.12 | 3.26 | 6.57 | 26.57 |

$^1$H-NMR δ (CDCl$_3$, ppm)
3.85 (4H (1), s )
6.41~6.45 (2H (2), m)
6.61~6.70 (4H (3), m)
6.73~6.77 (2H (4), m)
6.82~6.96 (1H (5), m)
7.16~7.40 (1H (6), m)
wherein (1)~(6) indicate positions on the following formula.

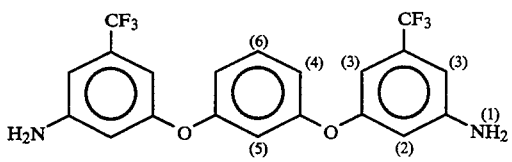

EXAMPLE 6

To a four necked flask equipped with a thermometer, reflux condenser and stirrer, 250 ml of DMF, 50 ml of toluene, 50 g (0.212 mol) of 3,5-dinitrobenzotrifluoride, 11.7 g (0.106 mol) of hydroquinone and 17.6 g (0.127 mol) of potassium carbonate were charged. The mixture was heated to 120° C. with stirring and aged for 8 hours at 120° C. After finishing the reaction, the reaction mixture was cooled to 80° C. and filtered to remove inorganic salts. The filtrate was mixed with 180 ml of water and cooled to the room temperature to crystallize the desired product. Precipitated crystals were filtered and recrystallized from isopropyl alcohol. 1,4-Bis(3-nitro-5-trifluoromethylphenoxy)benzene thus obtained was 36.5 g (70.5% yield) and had a melting point of 162.8°~163.3° C.

| Elemental analysis ($C_{20}H_{10}N_2O_6F_6$) | | | |
| --- | --- | --- | --- |
| C | H | N | F |
| Calculated (%) 49.20 | 2.06 | 5.74 | 23.34 |
| Found (%) 49.15 | 2.10 | 5.72 | 23.30 |

$^1$H-NMR δ (CDCl$_3$, ppm)
7.20 (4H (1), s )
7.60~7.62 (2H (2), m)
7.69~8.01 (1H (3), m)
7.21 (2H (4), s )
wherein (1)4(6) indicate positions on the following formula.

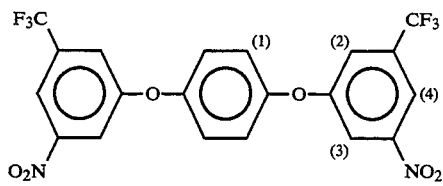

To a reducing apparatus equipped with a thermometer, reflux condenser and stirrer, 36.5 g (0.0747 mol) of 1,4-bis(3-nitro-5-trifluoromethylphenoxy)benzene, 250 ml of N,N-dimethylformamide and 1.8 g Pd-alumina were charged and reacted in a hydrogen atmosphere at 50° C. for 6 hours. After finishing the reaction, the catalyst was filtered and the filtrate was concentrated under reduced pressure to obtain 1,4-bis(3-amino-5-trifluoromethylphenoxy)benzene as colorless crystals. The product was 36.5 g (70.5% yield) and had a melting point of 157.4~158.0° C.

| Elemental analysis ($C_{20}H_{14}N_2O_2F_6$) | | | |
| --- | --- | --- | --- |
| C | H | N | F |
| Calculated (%) 56.08 | 3.29 | 6.54 | 26.61 |
| Found (%) 56.04 | 3.32 | 6.56 | 26.56 |

$^1$H-NMR δ (DMSO, ppm)
5.72 (4H (1), s )
6.39~6.41 (4H (2), m)
6.63 (2H (3), m)
7.12 (4H (4), m)
wherein (1)~(4) indicate positions on the following formula.

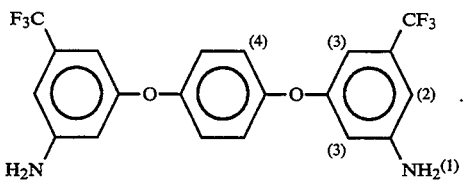

EXAMPLE 7

To a reducing apparatus equipped with a thermometer, reflux condenser and stirrer, 36.9 g (0.156 mol) of 3,5-dinitrobenzotrifluoride, 60 g (0.329 mol) of 3-amino-5-trifluoromethylphenol, 290 g of N,N-dimethylformamide and potassium carbonate were charged. The mixture was heated to 145° C. with stirring and aged for 14 hours at 145OC. At the end of reaction, the desired product had a purity of 63% by HPLC.

The reaction mixture was cooled after finishing the reaction and filtered to remove inorganic salts. 400 g of water was added to separate the organic layer. 400 g of toluene was added to the separated organic layer and the resultant solution was washed with an aqueous solution containing 2% NaOH. The residue obtained by distilling off toluene was purified by column chromatography to obtain 1,4-bis(3-amino-5-trifluoromethylphenoxy)-5-trifluoromethylbenzene as light yellow crystals. The product was 32 g (41.3% yield) and had a melting point of 82°~84° C.

$^1$H-NMR δ (CDCl$_3$, ppm)
3.93 (4H (1), s )
6.42~6.47 (2H (2), t)
6.62~6.68 (4H (3), m)

6.77~7.82 (2H (4), t)
6.99~7.01 (2H (5), d)
wherein (1)~(5) indicate positions on the following formula.

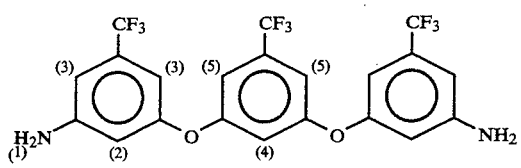

Properties of polyimide in the examples below were measured by the following methods.

Tg, Tc and Tm: Measured by DSC with Shimadzu DT-40 series, Model DSC-41M.

5% Weight loss temperature: Measured by DTG with Shimadzu DT-40 series, Model DTG-40M.

Dielectric constant: Measured in accordance with ASTM D 150-87.

Melt viscosity: Measured with a Shimadzu Koka type flow tester. Model CFT-500A under 100 Kg load.

Saturated moisture content: Measured after allowed to stand for 24 hours at 23° C. in 85% RH.

Melt initiation temperature: Measured with a Shimadzu Koka type flow tester. Model CFT-500A under 100 Kg load at a temperature rise rate of 5° C./min.

Yellowness index: Measured by a transmission method with a direct-reading color difference computer, model CDE-SCH-3 (manufactured by Suga Test Machine Co.) in accordance with JIS K-7103.

Light transmittance: Measured with a Hitachi self-recording spectro-photometer, model 3400.

Inherent viscosity: Measured at 35° C. in a concentration of 0.5 g/dl after individually dissolving polyamic acid in N,N-dimethylacetamide and polyimide in a mixture of p-chlorophenol/phenol at a ratio of 9/1 by weight.

Mechanical properties of film: Measured in accordance with ASTM D-822.

EXAMPLE 8

To a reaction vessel equipped with a stirrer, reflux condenser, water separator and nitrogen inlet tube, 50.45 g (0.1 mol) of 4,4'-bis(3-amino-5-trifluoromethylphenoxy)biphenyl, 21.38 g (0,098 mol) of pyromellitic dianhydride, 0.592 g ($4 \times 10^{-3}$ mol) of phthalic anhydride, 1.4 g of γ-picoline and 287.3 g of m-cresol were charged. The mixture was heated to 145° C. with stirring in a nitrogen atmosphere while distilling out about 3.5 ml water.

The reaction was further continued for 4 hours at 140°~150° C. The reaction mixture was then cooled to the room temperature and poured into about 1.5 l of methyl ethyl ketone.

Precipitated polyimide powder was filtered, washed with methyl ethyl ketone and dried at 180° C. for 24 hours under reduced pressure to obtain 67.45 g (98.0%) polyimide powder.

The polyimide powder thus obtained had an inherent viscosity of 0.47 dl/g, a glass transition temperature of 251° C. by DSC method, and a 5% weight loss temperature of 553° C. in the air. An infrared absorption spectrum of the polyimide powder is illustrated in FIG. 1.

The spectrum atlas clearly indicates characteristic absorption bands of imide at around 1780 $cm^{-1}$ and 1720 $cm^{-1}$, and also indicates characteristic absorption bands of a trifluoromethyl group at around 1130 $cm^{-1}$.

Results of elemental analysis on the polyimide powder thus obtained are as follows.

|  | Elemental analysis | | | |
| --- | --- | --- | --- | --- |
|  | C | H | N | F |
| Calculated (%) | 62.98 | 2.35 | 4.08 | 16.61 |
| Found (%) | 62.87 | 2.40 | 4.04 | 16.51 |

Figure 2:
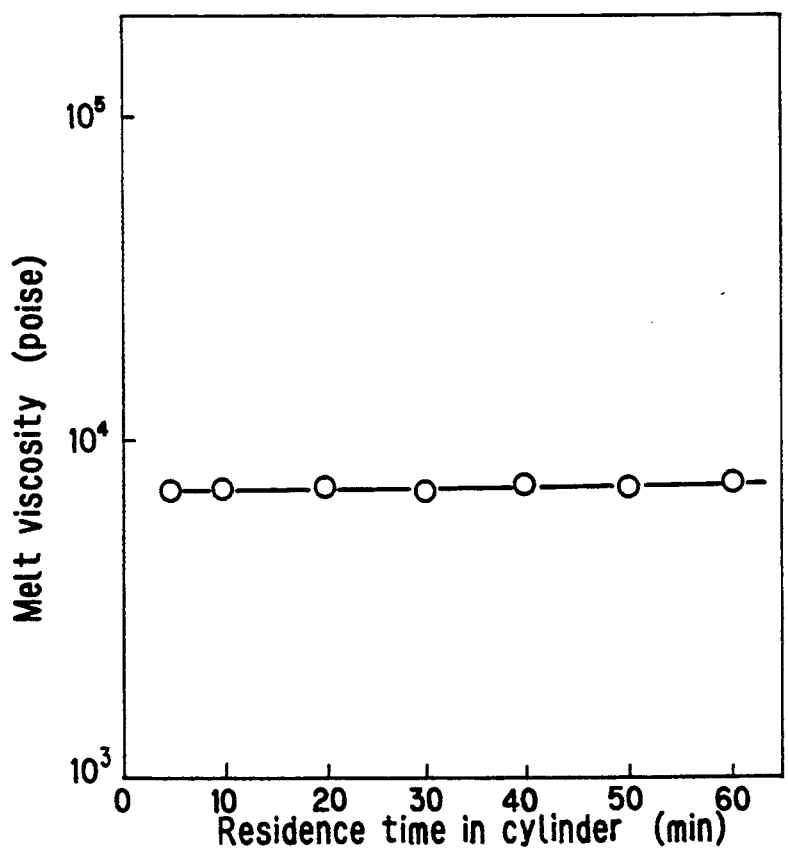
FIG. 2 is a drawing illustrating the relationship between the viscosity and the residence time of the polyimide powder obtained in Example 8 in the cylinder of a flow tester.

Melt viscosity of the polyimide was measured with a Koka type flow tester under 100 Kg load by using an orifice having a diameter of 0.1 cm and a length of 1 cm. Melt flow initiation temperature was 320° C., melt viscosity was 6950 poise at 400° C., and the strand obtained was red brown, transparent and very flexible. Processing stability of the polyimide in the examples was measured by changing the residence time in the cylinder of the flow tester. The measurement was carried out at 400° C. with a load of 100 Kg. Results are illustrated in FIG. 2. Melt viscosity is almost constant even thought residence time in the cylinder was extended, which indicates good heat stability.

The polyimide powder was hot-pressed at 380° C. under a pressure of 300 psi to form a film having a thickness of about 50 μm. The polyimide film obtained had dielectric constant of 3.36 at frequency of 60 Hz, 3.32 at 3 KHz and 3.24 at 1 MHz.

COMPARATIVE EXAMPLE 1

The same procedures as described in Example 8 were carried out except that 36.84 g (0.1 mol) of 4,4-bis(3-aminophenoxy)biphenyl was used in place of 50.45 g (0.1 mol) of 4,4-bis(3-amino-5-trifluoromethylphenoxy)-biphenyl to obtain 54.3 g (98.7% yield) of polyimide powder. The polyimide powder had an inherent viscosity of 0.46 dl/g, glass transition temperature of 248° C. and a 5% weight loss temperature of 561° C. in the air. Melt flow initiation temperature was 395° C. and melt viscosity was 9000 poise at 400° C. Polyimide film having a thickness of 50 μm was prepared by the same procedure as described in Example 1. The film had dielectric constant of 3.42 at frequency of 60 Hz, 3.40 at 3 KHz, and 3.34 at 1 MHz.

EXAMPLE 9

To a reaction vessel equipped with a stirrer, reflux condenser and nitrogen inlet tube, 50.45 g (0.1 mol) of 4,4'-bis(3-amino-5-trifluoromethylphenoxy)biphenyl obtained in Example 2 and 168.6 g of N,N-dimethylacetamide were charged. To the mixture, 21.81 g (0.1 mol) of pyromellitic dianhydride was added by portions with caution to prevent temperature rise of the solution and stirred for 30 hours at room temperature. Polyamic acid thus obtained had an inherent viscosity of 0.97 dl/g. A portion of the polyamic acid solution was cast on a glass plate and heated successively at 100° C., 200° C. and 300° C. for an hour each to obtain a film having a thickness of 50 μm.

Polyimide film thus obtained had a glass transition temperature of 263° C. and 0.5% weight loss temperature of 556° C. in the air. The film also had a tensile strength of 9.6 Kg/mm², tensile elastic modulus of 238 Kg/mm², and elongation of 56% in accordance with ASTM D-822.

The film had dielectric constant of 3.34 at frequency of 60 Hz, 3.32 at 3 KHz, and 3.22 at 1 MHz.

EXAMPLES 10~12

The same procedures as described in Example 8 were carried out by using a tetracarboxylic dianhydride illustrated in Table 1 in an amount shown in Table 1 to prepare polyimide powder, respectively. The yield, inherent viscosity, glass transition temperature (Tg), 5% weight loss temperature (Td 5.0) and values of elemental analysis on the polyimide powder thus obtained are summarized in Table 1.

Further, polyimide films were prepared by the same procedures as described in Example 8 and dielectric constant of these films was measured at frequency of 60 KHz and 1 MHz, respectively. Results are summarized in Table 3.

EXAMPLES 13~15

The same procedures as described in Example 9 were carried out by using a tetracarboxylic dianhydride illustrated in Table 2 in an amount shown in Table 2 to prepare polyamic acid, respectively. Further, polyimide films were prepared from these polyamic acid by using the same procedures from these polyamic acids by using the same procedures as described in Example 9. The inherent viscosity of these polyamic acids and glass transition temperatures (Tg), 5% weight loss temperature (Td 5.0) and mechanical properties of these polyimide films are illustrated in Table 2.

Further, dielectric constant of each polyimide film was measured at frequency of 60 Hz, 3 Khz and 1 MHz, respectively. Results are summarized in Table 3.

TABLE 1

| Example | Diamine compound g (mol) | Tetracarboxylic dianhydride g (mol) | yield (%) | η *5 (dl/g) | Tg *6 (%) | Td(5.0) *7 (°C.) | Elemental analysis (%) | C | H | N | F |
|---|---|---|---|---|---|---|---|---|---|---|---|
| 10 | m-BP-6F *1 50.45 g (0.1 mol) | BTDA *2 31.58 g (0.098 mol) | 98.1 | 0.51 | 234 | 535 | Calculated Found | 65.32 65.03 | 2.55 2.63 | 3.54 3.52 | 14.42 14.55 |
| 11 | ↑ | ODPA *3 30.40 g (0.098 mol) | 97.9 | 0.45 | 209 | 524 | Calculated Found | 64.78 64.61 | 2.59 2.70 | 3.60 3.50 | 14.64 14.39 |
| 12 | ↑ | 6FDA *4 43.54 g (0.098 mol) | 97.3 | 0.44 | 229 | 516 | Calculated Found | 59.22 59.64 | 2.21 2.23 | 3.07 3.01 | 24.98 24.11 |

Note:
*1 4,4'-bis(3-amino-5-trifluoromethylphenoxy) biphenyl
*2 3,3',4,4'-benzophenonetetracarboxylic dianhydride
*3 3,3',4,4'-diphenylethertetracarboxylic dianhydride
*4 2,2-bis(3,4-dicarboxyphenyl)-1,1,1,3,3,3-hexafluoroprppane dianhydride
*5 inherent viscosity of polyamic acid
*6 glass transition temperature
*7 5% weight loss temperature

TABLE 2

| Example | Diamine compound g (mol) | Tetracarboxylic dianhydride g (mol) | η *5) (dl/g) | Tg *6) (°C.) | Td(5.0) *7) (°C.) | Mechanical properties of polyimidee film | | |
|---|---|---|---|---|---|---|---|---|
| | | | | | | Tensile strength (Kg/mm$^2$) | Tensile modulus (Kg/mm$^2$) | Elongation (%) |
| 13 | m-BP-2F *1) 50.45 g (0.1 mol) | BTDA *2) 32.22 g (0.1 mol) | 0.84 | 238 | 538 | 11.8 | 289 | 8.4 |
| 14 | ↑ | ODPA *3) 31.02 g (0.1 mol) | 0.64 | 215 | 526 | 11.6 | 271 | 3.3 |
| 15 | ↑ | 6FDA *4) 44.43 g (0.1 mol) | 0.72 | 235 | 518 | 10.3 | 270 | 5.0 |

Note:
*1) 4,4'-bis(3-amino-5-fluoromethylphenoxy) biphenyl
*2) 3,3',4,4'-benzophenonetetracarboxylic dianhydride
*3) 3,3',4,4'-diphenylethertetracarboxylic dianhydride
*4) 2,2-bis(3,4-dicarboxyphenyl)-1,1,1,3,3,3-hexafluoroprppane dianhydride
*5) inherent viscosity of polyamic acid
*6) glass transition temperature
*7) 5% weight loss temperature

TABLE 3

| Example | Diamine compound | Tetracarboxylic dianhydride | Film preparation method *6) | Dielectric constent | | |
|---|---|---|---|---|---|---|
| | | | | 60 Hz | 3 KHz | 1 MHz |
| 8 | m-BP-6F *1) | PMDA *2) | A | 3.36 | 3.32 | 3.24 |
| 9 | ↑ | ↑ | B | 3.34 | 3.32 | 3.22 |
| 10 | ↑ | BTDA *3) | A | 3.31 | 3.30 | 3.23 |
| 11 | ↑ | OPDA *4) | ↑ | 3.16 | 3.13 | 3.10 |
| 12 | ↑ | 6FDA *5) | ↑ | 2.86 | 2.84 | 2.81 |
| 13 | ↑ | BTDA | B | 3.30 | 3.28 | 3.21 |
| 14 | ↑ | ODPA | ↑ | 3.14 | 3.12 | 3.07 |

TABLE 3-continued

| Example | Diamine compound | Tetracarboxylic dianhydride | Film preparation method *6) | Dielectric constent 60 Hz | 3 KHz | 1 MHz |
|---|---|---|---|---|---|---|
| 15 | ↑ | 6FDA | ↑ | 2.85 | 2.84 | 2.82 |

Note:
*1) 4,4'-bis(3-amino-5-trifluoromethylphenoxy) biphenyl
*2) pyromellitic dianhydride
*3) 3,3',4,4'-benzophenonetetracarboxylic dianhydride
*4) 3,3',4,4'-diphenylethertetracarboxylic dianhydride
*5) 2,2-bis(3,4-dicarboxyphenyl)-1,1,1,3,3,3-hexafluoroprppane dianhydride
*6) A; hot-press of polyimide powder, B; casting of polyimide acid

EXAMPLE 16

To a reaction vessel equipped with a stirrer, reflux condenser and nitrogen inlet tube, 36.04 g (0.1 mol) of 1,3-bis(3-aminophenoxy)-4-trifluoromethylbenzene obtained in Example 3 and 187.8 g of N,N-dimethylacetamide were charged. To the solution obtained, 44.43 g (0.1 mol) of 2,2-bis (3,4-dicarboxyphenyl)-1,1,1,3,3,3-hexafluoropropane dianhydride was added in a nitrogen atmosphere by portions with caution to prevent temperature rise of the solution and stirred for 30 hours at room temperature. Polyamic acid thus obtained had an inherent viscosity of 0.82 dl/g.

EXAMPLES 17~21 AND COMPARATIVE EXAMPLES 2~3

The same procedures as Example 16 were carried out by using diamine components and tetracarboxylic dianhydride components illustrated in Table 4 to obtain various polyimide films.

Table 4 summarizes diamine components, tetracarboxylic dianhydride components, inherent viscosity of polyamic acids, Tg, mechanical properties of films, dielectric constants, yellowness indexes, light transmittance at 500 nm and moisture absorption, together with the results of Example 16.

TABLE 4

| | Diamine component g (mol) | Acid anhydride component g (mol) | η (dl/g) | Tg (°C.) | Mechanical property | | | Dielectric constant | | | YI *7 | T *8 500 nm (%) | Moisture absorption *9 (%) |
|---|---|---|---|---|---|---|---|---|---|---|---|---|---|
| | | | | | Ts (Kg/mm²) | El (%) | TM (Kg/mm) | 60 Hz | 3 KHz | 1 MHz | | | |
| Example 16 | m,m-APB-CF₃ I *1 36.04 (0.1) | 6FDA *2 44.43 (0.1) | 0.82 | 211 | 9.12 | 3.0 | 372 | 2.90 | 2.87 | 2.83 | 8 | 86.5 | 0.55 |
| Example 17 | ↑ | ODPA *3 31.02 (0.1) | 0.90 | 189 | 11.92 | 4.7 | 292 | 3.20 | 3.18 | 3.13 | 10 | 84.8 | 1.13 |
| Example 18 | ↑ | BPDA *4 29.42 (0.1) | 0.86 | 196 | 10.43 | 5.6 | 311 | 3.24 | 3.21 | 3.14 | 9 | 85.3 | 0.88 |
| Example 19 | m,m-APB-CF₃ II *5 36.04 (0.1) | 6FDA 44.43 (0.1) | 1.19 | 201 | 9.97 | 3.8 | 314 | 2.89 | 2.87 | 2.84 | 8 | 87.0 | 0.52 |
| Example 20 | ↑ | ODPA 31.02 (0.1) | 0.87 | 175 | 11.91 | 4.6 | 325 | 3.16 | 3.14 | 3.09 | 10 | 83.3 | 1.20 |
| Example 21 | ↑ | BDPA 29.42 (0.1) | 0.99 | 191 | 10.01 | 6.0 | 332 | 3.20 | 3.17 | 3.11 | 12 | 82.5 | 0.92 |
| Comparat. Example 2 | m,m-APB *6 20.24 (0.1) | 6FDA 44.43 (0.1) | 1.13 | 201 | 11.42 | 5.9 | 381 | 3.14 | 3.11 | 3.00 | 12 | 80.6 | 0.79 |
| Comparat. Example 3 | ↑ | ODPA 31.02 (0.1) | 0.94 | 175 | 10.66 | 6.7 | 303 | 3.35 | 3.83 | 3.26 | 17 | 76.5 | 1.57 |

Note:
*1 1,3-bis(3-aminophenoxy)-4-trifluorobenzene
*2 2,2-bis(3,4-dicarboxyphenyl)-1,1,1,3,3,3,-hexafluoropropane
*3 3,3',4,4'-diphenylethertetracarboxylic dianhydride
*4 3,3',4,4'-biphenyltetracarboxylic dianhydride
*5 1,3-bis(3-aminophenoxy)-5-trifluorobenzene
*6 1,3-bis(3-aminophenoxy)benzene
*7 Yellowness index
*8 Light transmittance at 500 nm
*9 23° C., 85% Relative humidity A portion of the polyamic acid was cast on a glass plate and heated successively at 100° C., 200° C. and 300° C. each for an hour to obtain a film having a thickness of about 50 μm.

The polyimide film thus obtained had a glass transition temperature of 211° C., tensile strength of 9.12 Kg/mm², elongation of 3% and tensile modulus of 372 Kg/mm². Dielectric constant of the film was 2.90 at frequency of 60 Hz, 2.87 at 3 KHz and 2.83 at 1 MHz. The film also had an yellowness index (YI) of 8, light transmittance (T %) of 86.5%, and moisture absorption of 0.55%.

EXAMPLE 22

To a reaction vessel equipped with a stirrer, reflux condenser and nitrogen inlet tube, 36.04 g (0.1 mol) of 1,3-bis(3-aminophenoxy)-4-trifluoromethylbenzene obtained in Example 5, 43.09 g (0.097 mol) of 2,2-bis(3,4-dicarboxyphenyl)-1,1,1,3,3,3,-hexafluoropropane dianhydride, 0.8887 g (0.006 mol) of phthalic anhydride, 1.40 g of γ-picoline and 316.5 g of m-cresol were charged. The mixture was heated to 150° C. with stirring in a nitrogen atmosphere and successively reacted at 150° C. for 4 hours while distilling out about 3.6 ml of water.

After finishing the reaction, the reaction mixture was cooled to the room temperature and poured into about 2 l of isopropanol. The precipitated polyimide powder was filtered, washed with isopropanol and dried in the air at 50° C. for 24 hours and thereafter at 200° C. for 4 hours to obtain 77.34 g (96.7% yield) of polyimide powder.

The polyimide powder thus obtained had an inherent viscosity of 0.48 dl/g, glass transition temperature of 206° C. and 5% weight loss temperature of 512° C.

Figure 3:
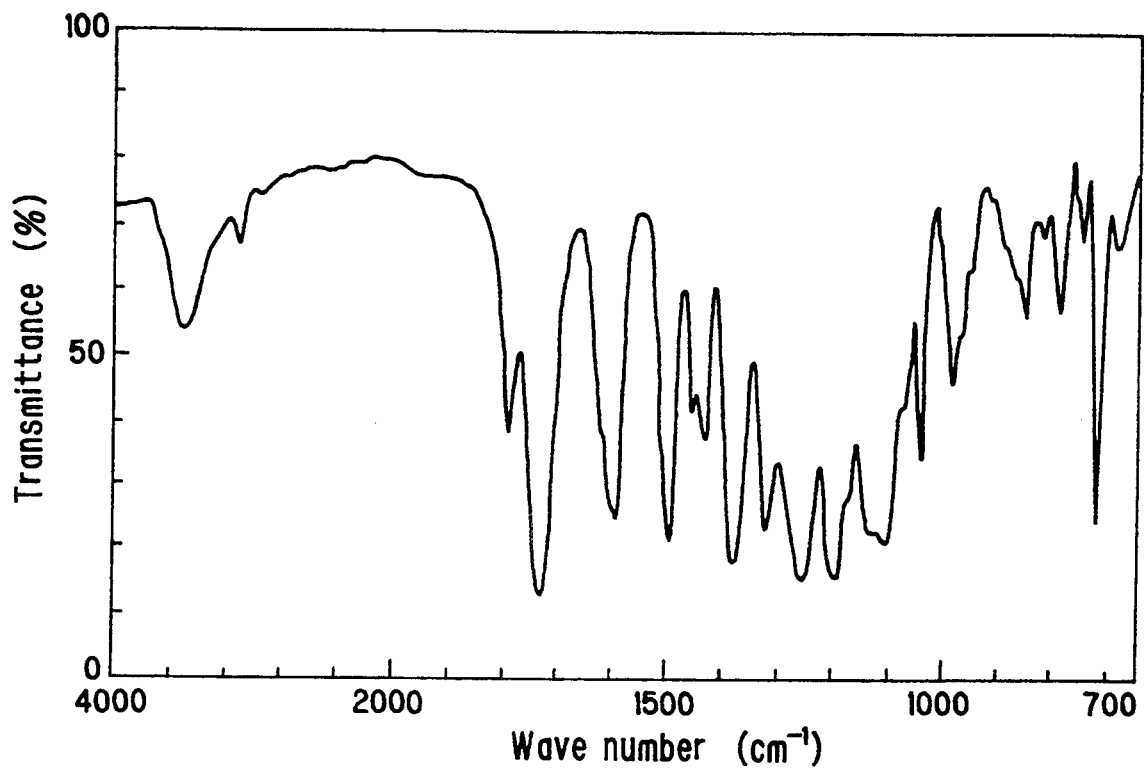
FIG. 3 illustrates an infrared absorption spectrum of the polyimide powder obtained in Example 22.

FIG. 3 illustrates an infrared absorption spectrum of the polyimide powder. The spectrum atlas has a remarkable absorption at around $1780^{-1}$ and $1720$ cm$^{-1}$ which are characteristic absorption bands of imide.

Elemental analysis results of the polyimide powder are as follows.

|  | C | H | N | F |
|---|---|---|---|---|
| Calculated (%) | 59.38 | 2.23 | 3.65 | 22.25 |
| Found (%) | 58.46 | 2.16 | 3.88 | 22.29 |

Figure 4:
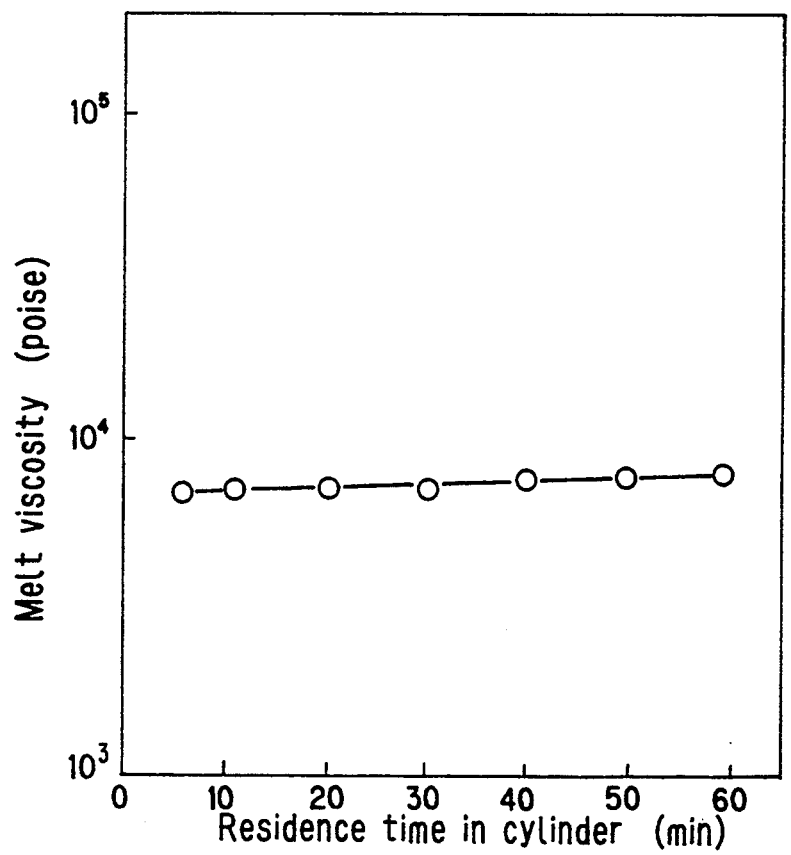
FIG. 4 is a drawing illustrating the relationship between the viscosity and the residence time of the polyimide powder obtained in Example 22 in the cylinder of a flow tester.

The polyimide powder had flow initiation temperature of 280° C. by the Koka type flow tester and melt viscosity of 8600 poise at 350° C. Processing stability of the polyimide was measured by changing residence time in the cylinder of the flow tester. Results at 360° C. under 100 Kg load are illustrated in FIG. 4. Melt viscosity was almost unchanged although residence time was extended in the cylinder. Thus, processing stability was good.

The polyimide powder thus obtained was dissolved in N,N-dimethylacetamide in a concentration of 20% by weight, cast on a glass plate and removed the solvent at 200° C. to obtain a film having a thickness of about 50 μm. The film had dielectric constant of 2.93 at frequency of 60 Hz, 2.88 at 3 KHz, and 2.86 at 1 MHz. The film also had YI of 10, light transmittance of 84% at 50 nm and moisture absorption of 0.60%.

COMPARATIVE EXAMPLE 4

The same procedures as described in Example 22 were carried out except that 29.24 g (0.1 mol) of 1,4-bis(3-aminophenoxy)benzene was used in place of 36.04 g (0.1 mol) of 1,3-bis(3-aminophenoxy)-4-trifluoromethylbenzene to obtain 68.0 g (99.0% yield) of polyimide powder. The polyimide powder had an inherent viscosity of 0.49 dl/g, glass transition temperature of 210° C. and a 5% weight loss temperature of 541° C. in the air. Melt flow initiation temperature was 270° C. and melt viscosity was 9500 poise at 350° C. Polyimide film having a thickness of 50 μm was prepared by the same procedure as described in Example 22. The film had dielectric constant of 3.25 at frequency of 60 Hz, 2.21 at 3 KHz, and 3.20 at 1 MHz.

EXAMPLES 23~27

The same procedures as described in Example 22 were carried out by using diamine components and tetracarboxylic dianhydride components as illustrated in Table 5 to obtain various polyimide powder. Further, polyimide films were prepared by the same procedures as described in Example 22.

Table 5 illustrated diamine components, tetracarboxylic dianhydride components, inherent viscosity of polyamic acids, Tg, melt viscosity at 350° C., dielectric constant, YI, light transmittance at 500 nm and moisture absorption, together with the results of Example 22.

TABLE 5

|  | Diamine component g (mol) | Acid anhydride component g (mol) | Yield (%) | η (dl/g) | Tg (°C.) | Td 5% (°C.) | Inherent viscosity 350° C. (poise) | Dielectric constant | | | YI | T 500 nm (%) | Moisture absorption (%) |
|---|---|---|---|---|---|---|---|---|---|---|---|---|---|
|  |  |  |  |  |  |  |  | 60 Hz | 3 KHz | 1 MHz |  |  |  |
| Example 22 | m,m-APB-CF$_3$ I 36.04 (0.1) | 6FDA 43.09 g (0.087) | 96.7 | 0.48 | 206 | 517 | 8800 | 2.93 | 2.88 | 2.86 | 10 | 84.0 | 0.60 |
| Example 23 | ↑ | ODPA 30.09 g (0.087) | 98.0 | 0.47 | 182 | 504 | 7050 | 3.21 | 3.20 | 3.14 | 15 | 81.3 | 1.23 |
| Example 24 | ↑ | BPDA 25.54 g (0.087) | 97.7 | 0.52 | 193 | 515 | 8130 | 3.22 | 3.20 | 3.14 | 15 | 82.0 | 0.91 |
| Example 25 | m,m-APB-CF$_3$ II (36.04 (0.1)) | 6FDA 43.09 g (0.087) | 96.6 | 0.49 | 197 | 513 | 8060 | 2.85 | 2.91 | 2.88 | 11 | 85.3 | 0.63 |
| Example 26 | ↑ | ODPA 30.09 g (0.087) | 96.3 | 0.46 | 170 | 504 | 6780 | 3.18 | 3.17 | 3.11 | 18 | 80.5 | 1.31 |
| Example 27 | ↑ | BPDA 28.54 g (0.087) | 97.1 | 0.50 | 187 | 511 | 7740 | 3.21 | 3.19 | 3.13 | 13 | 81.1 | 0.97 |

Note:
*1) 5% weight loss temperature
*2) other abbreviations are the same as in Table 4

EXAMPLE 28

To a reaction vessel equipped with a stirrer, reflux condenser and nitrogen inlet tube, 42.84 g (0.1 mol) of 1,3-bis(3-amino-5-trifluoromethylphenoxy)benzene obtained in Example 5 and 203.6 g of N,N-dimethylacetamide were charged. To the solution obtained, 44.43 g (0.1 mol) of 2,2-bis(3,4-dicarboxyphenyl)-1,1,1,3,3,3-hexafluoropropane dianhydride was added by portions in a nitrogen atmosphere with caution to prevent temperature rise of the solution and stirred for 30 hours at room temperature. The polyamic acid thus obtained had an inherent viscosity of 0.72 dl/g. A portion of the polyamic acid was cast on a glass plate and successively heated at 100° C., 200° C. and 300° C. each for an hour to obtain a film having a thickness of about 50 μm.

The polyimide film thus obtained had a glass transition temperature of 194° C., tensile strength of 8.76 Kg/mm$^2$, elongation of 3.6% and tensile modulus of 283 Kg/mm$^2$. The polyimide film had dielectric constant of 2.84 at frequency of 60 Hz, 2.81 at 3 KHz, and 2.79 at 1 MHz. The film also had yellowness index (YI) of 7, light transmittance (T) of 88.8% at 500 nm, and moisture absorption of 0.36%.

EXAMPLES 29~33 AND COMPARATIVE EXAMPLES 5~8

The same procedures as described in Example 28 were carried out by using diamine components and tetracarboxylic dianhydride components as illustrated in Table 6 to obtain various films. Table 6 illustrates diamine components, tetracarboxylic dianhydride components, inherent viscosity of polyamic acids, Tg, mechanical properties of films, dielectric constant, yellowness index, light transmittance at 500 nm and moisture absorption, together with results of Example 28.

50° C. for 24 hours and successively at 200° C. for 4 hours.

The polyimide powder thus obtained was 79.84 g (96.0% yield) and had an inherent viscosity of 0.47 dl/g, glass transition temperature of 191° C. and 5% weight loss temperature of 509° C.

Figure 5:
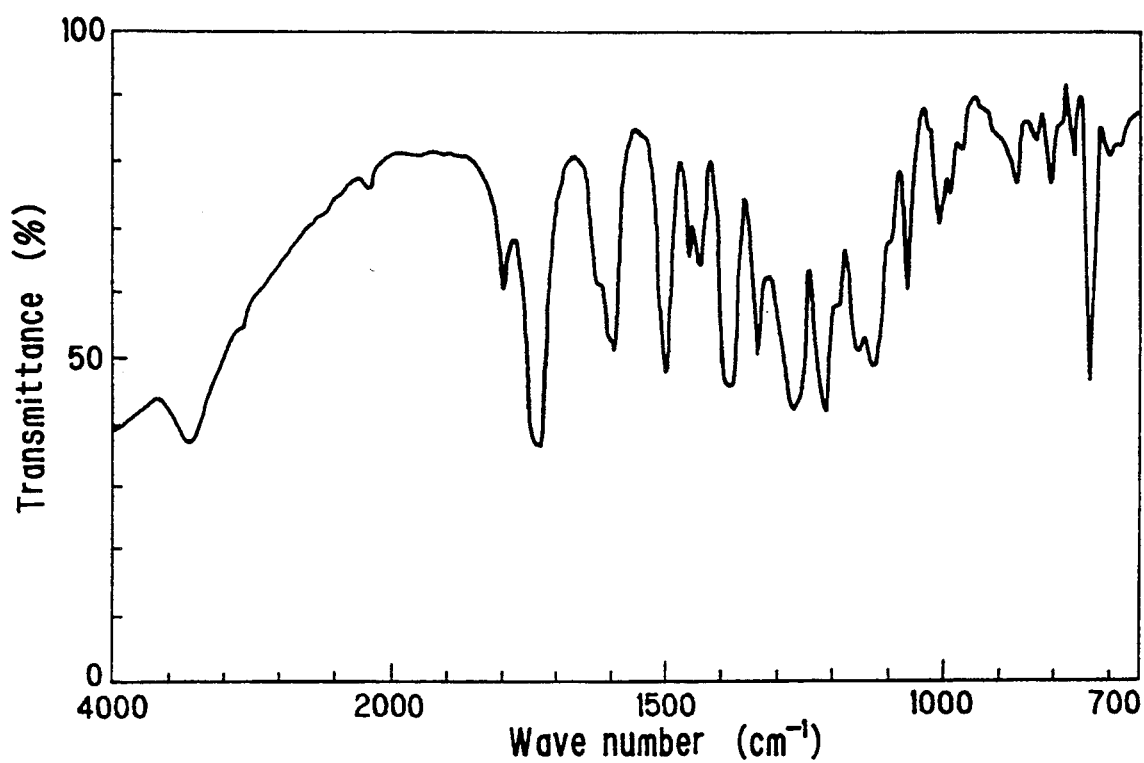
FIG. 5 illustrates an infrared absorption spectrum of the polyimide powder obtained in Example 34.

The infrared absorption spectrum of the polyimide powder is illustrated in FIG. 5. The spectrum atlas remarkably exhibits absorption around 1780 and 1720 $cm^{-1}$ which are characteristic absorption bands of imide.

Following results were obtained on the elemental analysis of the polyimide powder.

TABLE 6

| | Diamine component g (mol) | Acid anhydride component g (mol) | η (dl/g) | Tg (°C.) | Mechanical property | | | Dielectric constant | | | YI | T 500 nm (%) | Moisture absorption (%) |
| | | | | | Ts (Kg/mm²) | El (%) | TM (Kg/mm) | 60 Hz | 3 KHz | 1 MHz | | | |
|---|---|---|---|---|---|---|---|---|---|---|---|---|---|
| Example 28 | m,m-APB-2CF₃ *1 42.84 (0.1) | 6FDA *2 44.43 g (0.1) | 0.72 | 194 | 8.76 | 3.6 | 283 | 2.84 | 2.81 | 2.79 | 7 | 88.8 | 0.36 |
| Example 29 | ↑ | ODPA *3 31.02 g (0.1) | 0.92 | 180 | 11.57 | 4.3 | 322 | 3.01 | 2.99 | 2.96 | 10 | 86.9 | 0.99 |
| Example 30 | ↑ | BPDA *4 29.42 g (0.1) | 0.85 | 200 | 10.11 | 5.0 | 313 | 3.07 | 3.06 | 3.02 | 8 | 87.8 | 0.76 |
| Example 31 | m,p-APB-2CF₃ *5 42.84 (0.1) | 6FDA 44.43 g (0.1) | 0.71 | 217 | 9.87 | 3.4 | 376 | 2.95 | 2.94 | 2.91 | 9 | 85.6 | 0.39 |
| Example 32 | ↑ | ODPA 31.02 g (0.1) | 1.02 | 197 | 11.36 | 5.2 | 264 | 3.13 | 3.11 | 3.07 | 19 | 81.2 | 0.97 |
| Example 33 | ↑ | BPDA 29.42 g (0.1) | 1.13 | 223 | 10.59 | 6.2 | 305 | 3.17 | 3.11 | 3.06 | 15 | 84.3 | 0.84 |
| Comparat. Example 5 | m,m-ABB *6 31.63 (0.1) | 6FDA 44.43 g (0.1) | 1.05 | 235 | 10.53 | 7.0 | 375 | 3.40 | 3.20 | 3.17 | 20 | 75.3 | 1.10 |
| Comparat. Example 6 | Bis-M 34.45 (0.1) | ↑ | 1.11 | 231 | 9.89 | 3.2 | 367 | 3.20 | 3.19 | 3.18 | 13 | 77.1 | 1.06 |
| Comparat. Example 7 | m,p-APB *7 29.24 (0.1) | ↑ | 1.05 | 213 | 10.98 | 6.4 | 352 | 3.20 | 3.17 | 3.15 | 32 | 79.5 | 1.01 |
| Comparat. Example 8 | ↑ | ODPA 31.02 g (0.1) | 1.16 | 201 | 10.21 | 8.3 | 311 | 3.35 | 3.33 | 3.29 | 40 | 78.3 | 1.55 |

Note:
*1 1,3-bis(3-amino-5-trifluoromethylphenoxy)benzene
*2 2,2,-bis(3,4-dicarboxyphenyl)-1,1,1,3,3,3,-hexafluoropropane dianhydride
*3 3,3',4,4'-diphenylethertetracarboxylic dianhydride
*4 3,3',4,4'-biphenyltetracarboxylic dianhydride
*5 1,4-bis(3-amino-5-trifluoromethylphenoxy)benzene
*6 1,3-bis(3-aminophenoxy)benzene
*7 1,4-bis(3-aminophenoxy)benzene
*8 Other abbreviations are the same as in Table 4

| | C | H | N | F |
|---|---|---|---|---|
| Calculated (%) | 59.38 | 2.23 | 3.65 | 22.25 |
| Found (%) | 58.46 | 2.16 | 3.88 | 23.29 |

EXAMPLE 34

To a reaction vessel equipped with a stirrer, reflux condenser and nitrogen inlet tube, 42.84 (0.1 mol) of 1,3-bis(3-amino-5-trifluoromethylphenoxy)benzene obtained in Example 5, 43.09 g (0.097 mol) of 2,2-bis(3,4-dicarboxyphenyl)-1,1,1,3,3,3-hexafluoropropane dianhydride, 0.8887 g (0.006 mol) of phthalic anhydride, 1.40 g of γ-picoline, and 316.5 g of m-cresol were charged. The mixture was heated to 150° C. with stirring in a nitrogen atmosphere and reacted at 150° C. for 4 hours while distilling out about 3.6 ml of water.

Figure 6:
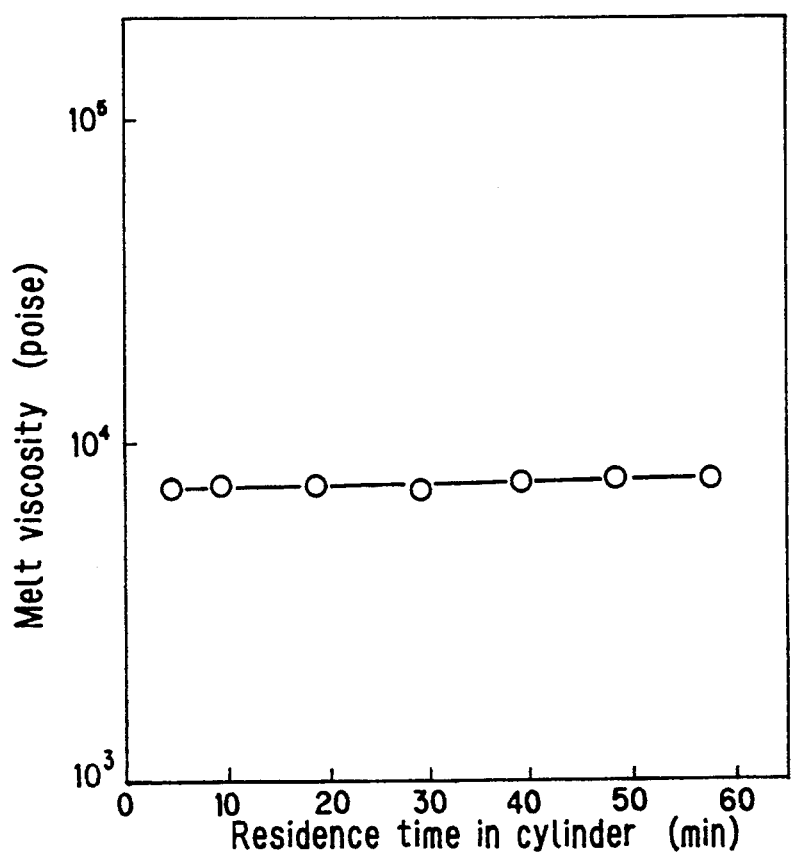
FIG. 6 is a drawing illustrating relationship between the viscosity and the residence time of the polyimide powder obtained in Example 34 in the cylinder of a flow tester.

After finishing the reaction, the reaction mixture was cooled to room temperature and poured into about 2 l of isopropanol. The precipitated polyimide powder was filtered, washed with isopropanol and dried in the air at Flow initiation temperature was measured with a Koka type flow tester. The polyimide powder had flow initiation temperature of 280° C. and melt viscosity of 7240 poise at 350° C. Processing stability of the polyimide was measured by changing the residence time in the cylinder of the flow tester. Results measured at 360° C. under 100 Kg load are illustrated in FIG. 6. Melt viscosity was almost unchanged even though residence time in the cylinder was extended. Thus processing stability was good.

The polyimide powder was dissolved in N,N-dimethylacetamide in a concentration of 20% by weight, cast on a glass plate and removed the solvent at 200° C.

to obtain a film having a thickness of about 50 μm. The polyimide film had dielectric constant of 2.87 at frequency of 60 Hz, 2.84 at 3 KHz and 2.82 at 1 MHz. The film also had YI of 9, light transmittance of 86.5% at 500 nm, and moisture absorption of 0.42%.

EXAMPLES 35~39

The same procedures as described in Example 34 were carried out by using diamine components and tetracarboxylic dianhydride components illustrated in Table 7 to obtain various polyimide powder. Further, polyimide films were prepared by the same procedures as described in Example 34. Table 7 illustrates diamine components, tetracarboxylic dianhydride components, inherent viscosity of the polyimide powder, Tg, melt viscosity at 350° C., dielectric constant, YI, light transmittance at 500 nm, and moisture absorption, together with the results of Example 34.

stirred for 30 hours at the room temperature. The polyamic acid thus obtained had an inherent viscosity of 0.54 dl/g. A portion of the polyamic acid was cast on a glass plate and successively heated at 100° C., 230° C. and 300° C. each for an hour to obtain a film having a thickness of about 50 μm.

The polyimide film thus obtained had a glass transition temperature of 190° C., tensile strength of 8.94 Kg/mm$^2$, elongation of 4.4% and tensile modulus of 288 Kg/mm$^2$. The polyimide film had dielectric constant of 2.83 at frequency of 60 Hz, 2.81 at 3 KHz, and 2.79 at 1 MHz. The film also had yellowness index (YI) of 7, light transmittance (T) of 88.6% at 500 nm, and moisture absorption of 0.26%.

EXAMPLES 41~42

The same procedures as described in Example 40 were carried out by using diamine components and

TABLE 7

| | Diamine component g | Acid anhydride component g (mol) | Yield (%) | η (dl/g) | Tg (°C.) | Td 5% (°C.) | Melt viscosity 350° C. (poise) | Dielectric constant | | | YI | T 500 nm (%) | Moisture absorption (%) |
|---|---|---|---|---|---|---|---|---|---|---|---|---|---|
| | | | | | | | | 60 Hz | 3 KHz | 1 MHz | | | |
| Example 34 | m,m-APB-2CF$_3$ 42.84 (0.1) | 6FDA 43.09 g (0.097) | 96.0 | 0.47 | 191 | 507 | 7240 | 2.84 | 2.81 | 2.79 | 7 | 88.7 | 0.36 |
| Example 35 | ↑ | ODPA 30.09 g (0.097) | 97.2 | 0.45 | 167 | 501 | 6110 | 3.05 | 3.03 | 3.02 | 13 | 82.9 | 0.97 |
| Example 36 | ↑ | BPDA 28.54 g (0.097) | 97.3 | 0.46 | 183 | 510 | 7720 | 3.06 | 3.04 | 3.02 | 11 | 82.5 | 0.85 |
| Example 37 | m,m-APB-2CF$_3$ 42.84 (0.1) | 6FDA 43.09 g (0.097) | 95.9 | 0.48 | 214 | 511 | 8110 | 2.99 | 2.96 | 2.94 | 11 | 81.4 | 0.44 |
| Example 38 | ↑ | ODPA 30.09 g (0.097) | 97.0 | 0.45 | 191 | 498 | 7080 | 3.15 | 3.14 | 3.11 | 22 | 79.8 | 1.01 |
| Example 39 | ↑ | BPDA 28.54 g (0.097) | 95.5 | 0.49 | 218 | 510 | 6990 | 3.20 | 3.16 | 3.13 | 17 | 86.0 | 0.88 |

Note:
Abbreviations are the same as in Table 6

EXAMPLE 40

To a reaction vessel equipped with a stirrer, reflux condenser and nitrogen inlet tube, 49.64 g (0.1 mol) of 1,3-bis(3-amino-5-trifluoromethylphenoxy)-5-trifluoromethylbenzene obtained in Example 7 and 219.5 g of N,N-dimethylacetamide were charged. To the solution obtained, 44.43 g (0.1 mol) of 2,2-bis(3,4-dicarboxyphenyl)-1,1,1,3,3,3-hexafluoropropane dianhydride was added by portions in a nitrogen atmosphere with caution to prevent temperature rise of the solution and tetracarboxylic dianhydride components as illustrated in Table 8 to obtain various films. Table 8 illustrates diamine components, tetracarboxylic dianhydride components, inherent viscosity of polyamic acids, Tg, mechanical properties of films, dielectric constant, yellowness index, light transmittance at 500 nm and moisture absorption, together with results of Example 40.

TABLE 8

| | Diamine component g | Acid anhydride component g (mol) | η (dl/g) | Tg (°C.) | Mechanical property | | | Dielectric constant | | | YI | T 500 nm (%) | Moisture absorption (%) |
|---|---|---|---|---|---|---|---|---|---|---|---|---|---|
| | | | | | Ts (Kg/mm$^2$) | EL (%) | TM (Kg/mm) | 60 Hz | 3 KHz | 1 MHz | | | |
| Example 40 | m,m-APB-3CF$_3$ *1 49.64 (0.1)1) | 6FDA 44.46 (0.1) | 0.54 | 190 | 8.94 | 4.4 | 288 | 2.83 | 2.81 | 2.79 | 7 | 88.6 | 0.26 |
| Example 41 | ↑ | ODPA 31.02 (↑) | 0.63 | 176 | 11.10 | 5.2 | 316 | 3.03 | 3.01 | 2.99 | 11 | 85.9 | 0.54 |
| Example 42 | ↑ | BPDA 29.42 (↑) | 0.63 | 192 | 10.87 | 4.9 | 320 | 3.04 | 3.02 | 2.99 | 11 | 86.0 | 0.51 |

Note:
*1 1,3-Bis(3-amino-5-trifluoromethylphenyl)-5-trifluoromethylbenzene
*2 Abbreviations are the same as in Table 6

EXAMPLE 43

To a reaction vessel equipped with a stirrer, reflux condenser and nitrogen inlet tube, 49.64 g (0.1 mol) of 1,3-bis(3-amino-5-trifluoromethylphenoxy)-5-trifluoromethylbenzene, 43.09 g (0.097 mol) of 2,2-bis(3,4-dicarboxyphenyl)-1,1,1,3,3,3-hexafluoropropane dianhydride, 0.8887 g (0.006 mol) of phthalic anhydride, 1.40 g of γ-picoline, and 316.5 g of m-cresol were charged. The mixture was heated to 150° C. with stirring in a nitrogen atmosphere and reacted at 150° C. for 4 hours while distilling out about 3.6 ml of water.

After finishing the reaction, the reaction mixture was cooled to the room temperature and poured into about 2 l of isopropanol. The precipitated polyimide powder was filtered, washed with isopropanol and dried in the air at 50° C. for 24 hours and successively at 200° C. for 4 hours.

The polyimide powder thus obtained was 86.02 g (95.6% yield) and had an inherent viscosity of 0.43 dl/g, glass transition temperature of 188° C. and 5% weight loss temperature of 505° C.

Figure 7:
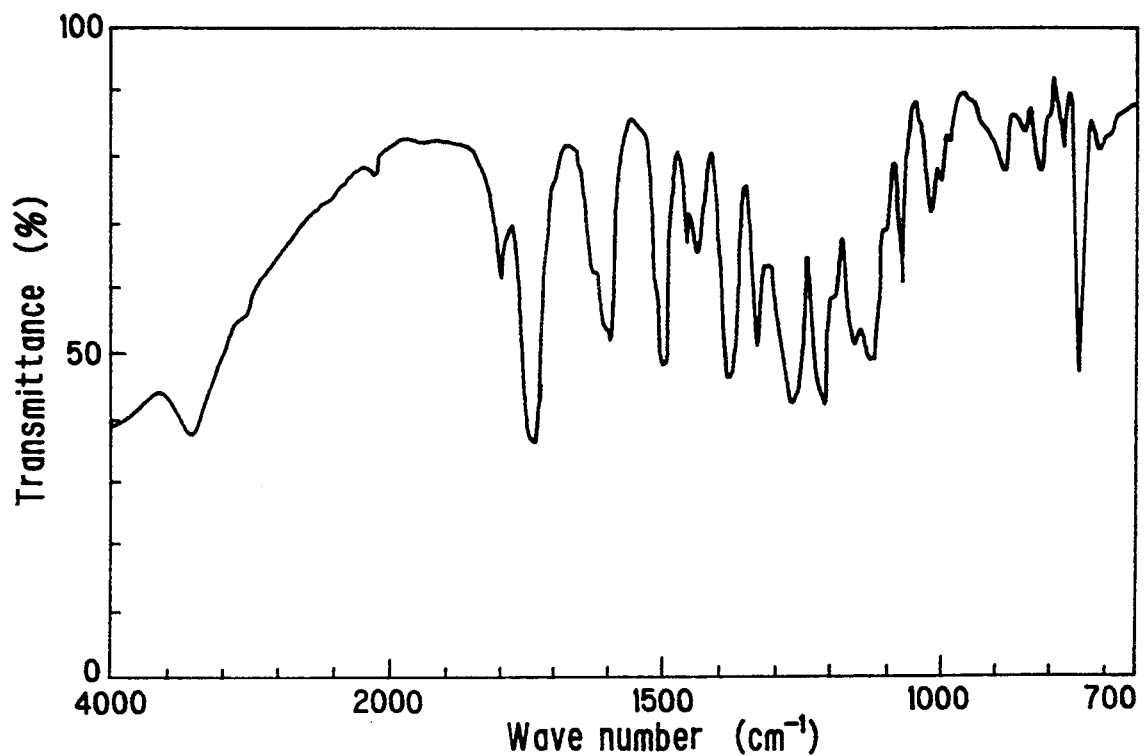
FIG. 7 illustrates an infrared absorption spectrum of the polyimide powder obtained in Example 43.

The infrared absorption spectrum of the polyimide powder is illustrated in FIG. 7. The spectrum atlas remarkably exhibits absorption around 1780 and 1720 cm$^{-1}$ which are characteristic absorption bands of imide.

Following results were obtained on the elemental analysis of the polyimide powder.

|  | C | H | N | F |
|---|---|---|---|---|
| Calculated (%) | 59.38 | 2.23 | 3.65 | 22.25 |
| Found (%) | 58.46 | 2.16 | 3.88 | 23.29 |

Figure 8:
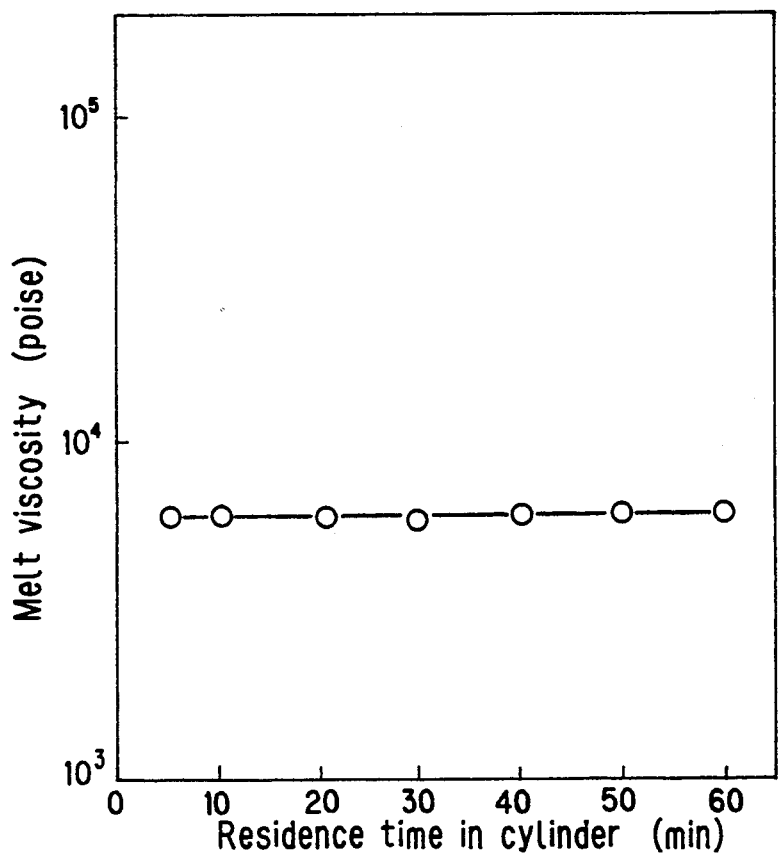
FIG. 8 is a drawing illustrating the relationship between the viscosity and the residence time of the polyimide powder obtained in Example 43 in the cylinder of a flow tester.

Flow initiation temperature was measured with a Koka type flow tester. The polyimide powder had flow initiation temperature of 275° C. and melt viscosity of 6620 poise at 350° C. Processing stability of the polyimide was measured by changing the residence time in the cylinder of the flow tester. Results measured at 360° C. under 100 Kg load are illustrated in FIG. 8. Melt viscosity was almost unchanged even though residence time in the cylinder was extended. Thus processing stability was good.

The polyimide powder was dissolved in N,N-dimethylacetamide in a concentration of 20% by weight, cast on a glass plate and removed the solvent at 200° C. to obtain a film having a thickness of about 50 μm. The polyimide film had dielectric constant of 2.85 at frequency of 60 Hz, 2.82 at 3 KHz and 2.80 at 1 MHz. The film also had YI of 7, light transmittance of 88.1% at 500 nm, and moisture absorption of 0.31%.

EXAMPLES 44~45

The same procedures as described in Example 43 were carried out by using diamine components and tetracarboxylic dianhydride components illustrated in Table 9 to obtain various polyimide powder. Further, polyimide films were prepared by the same procedures as described in Example 43. Table 9 illustrates diamine components, tetracarboxylic dianhydride components, inherent viscosity of the polyimide powder, Tg, melt viscosity at 350° C., dielectric constant, YI, light transmittance at 500 nm, and moisture absorption, together with the results of Example 43.

TABLE 9

| | Diamine component g | Acid anhydride component g (mol) | Yield (%) | η (dl/g) | Tg (°C.) | Td 5% (°C.) | Melt viscosity 350° C. (poise) | Dielectric constant | | | YI | T 500 nm (%) | Moisture absorption (%) |
|---|---|---|---|---|---|---|---|---|---|---|---|---|---|
| | | | | | | | | 60 Hz | 3 KHz | 1 MHz | | | |
| Example 43 | m,m-APB-3CF$_3$ 49.64 (0.1) | 6FDA 43.09 (0.097) | 95.6 | 0.43 | 188 | 505 | 6620 | 2.85 | 2.82 | 2.80 | 7 | 88.1 | 0.31 |
| Example 44 | ↑ | ODPA 30.09 (↑) | 96.3 | 0.42 | 173 | 496 | 5230 | 3.03 | 3.01 | 2.99 | 12 | 84.9 | 0.60 |
| Example 45 | ↑ | BPDA 28.54 (↑) | 95.9 | 0.47 | 191 | 508 | 7120 | 3.05 | 3.03 | 3.00 | 10 | 85.4 | 0.57 |

Note:
Abbreviations are the same as in Table 8

EXAMPLES 46~60

The same procedures as described in Example 16 were carried out by using diamine components and tetracarboxylic dianhydride components illustrated in Table 10 to obtain various polyimide powders. Further, polyimide films were prepared by the same procedures as described in Example 16.

Table 10 illustrates diamine components, tetracarboxylic dianhydride components, inherent viscosity of the polyimide powder, Tg, melt viscosity at 350° C., dielectric constant, YI, light transmittance at 500 nm, and moisture absorption.

In table 10, diamine components are as follows.

A: 1,3-bis(4-amino-5-trifluoromethyl-α,α-dimethylbenzyl)benzene
B: 1,3-bis(4-amino-4-trifluoromethylbenzoyl)benzene
C: 1,3-bis(3-amino-4-trifluoromethylbenzoyl)-5-trifluoromethylbenzene
D: 1,3-bis(3-amino-5-trifluoromethylphenyl)benzene
E: 1,3-bis(3-amino-4-pentafluoromethylbenzoyl)benzene
F: 4,4'-bis(3-amino-5-trifluoromethylphenoxy)benzophenone
G: 2,2-bis[4-(3-amino-5-trifluoromethylphenoxy)phenyl]propane
H: 4,4'-bis(3-amino-5-trifluoromethylbenzoyl)diphenylether
I: 4,4'-bis(3-amino-5-trifluoromethylbenzoyl)biphenyl
J: 4,4'-bis(3-amino-5-trifluoromethylphenyl)diphenylether
K: 2,2-bis[4-(3-amino-5-pentafluoromethylphenoxy)phenyl]propane

TABLE 10

| | Diamine component g (mol) | Acid anhydride component g (mol) | η (dl/g) | Tg (°C.) | Mechanical property Ts (Kg/mm$^2$) | EL (%) | TM (Kg/mm) | Dielectric constant 60 Hz | 3 KHz | 1 MHz | YI | T 500 nm (%) | Moisture absorption (%) |
|---|---|---|---|---|---|---|---|---|---|---|---|---|---|
| Example 46 | A 49.05 (0.1) | 6FDA 44.43 (0.1) | 0.80 | 225 | 12.26 | 4.5 | 320 | 2.95 | 2.95 | 2.92 | 10 | 84.3 | 0.54 |
| Example 47 | B 45.23 (↑) | ↑ | 0.78 | 246 | 13.06 | 3.8 | 336 | 3.09 | 3.07 | 3.05 | 23 | 80.5 | 0.84 |
| Example 48 | C 52.03 (↑) | ↑ | 0.85 | 244 | 12.59 | 3.9 | 328 | 3.06 | 3.00 | 2.98 | 19 | 81.5 | 0.63 |
| Example 49 | D 39.63 (↑) | ↑ | 0.90 | 251 | 13.52 | 3.5 | 345 | 2.94 | 2.98 | 2.91 | 9 | 86.0 | 0.42 |
| Example 50 | E 55.24 (↑) | ↑ | 1.08 | 239 | 12.26 | 4.3 | 315 | 3.06 | 3.05 | 3.03 | 17 | 82.2 | 0.71 |
| Example 51 | B 45.23 (↑) | ODPA 31.02 (↑) | 1.14 | 215 | 10.56 | 6.3 | 303 | 3.29 | 3.27 | 3.25 | 31 | 74.3 | 0.98 |
| Example 52 | C 52.03 (↑) | ↑ | 0.80 | 211 | 11.04 | 7.1 | 298 | 3.24 | 3.23 | 3.21 | 28 | 75.3 | 0.90 |
| Example 53 | F 53.24 (0.1) | 6FDA 44.43 (0.1) | 1.21 | 198 | 10.51 | 6.3 | 298 | 3.24 | 3.22 | 3.19 | 18 | 84.2 | 0.66 |
| Example 54 | G 54.65 | ↑ | 0.99 | 210 | 10.23 | 7.1 | 311 | 2.93 | 2.91 | 2.89 | 11 | 86.6 | 0.42 |
| Example 55 | H 54.45 | ↑ | 0.93 | 233 | 11.02 | 8.5 | 273 | 3.06 | 3.05 | 3.03 | 15 | 83.4 | 0.59 |
| Example 56 | I 52.85 (0.1) | ↑ | 1.03 | 238 | 10.58 | 7.0 | 263 | 3.12 | 3.11 | 3.00 | 18 | 83.9 | 0.61 |
| Example 57 | J 48.84 | ↑ | 0.88 | 236 | 9.38 | 6.2 | 280 | 3.04 | 3.01 | 2.99 | 14 | 83.0 | 0.73 |
| Example 58 | K 64.65 | ↑ | 1.11 | 206 | 10.06 | 6.2 | 291 | 2.90 | 2.88 | 2.86 | 9 | 86.9 | 0.67 |
| Example 59 | H 54.45 (0.1) | ODPA 31.02 (↑) | 1.00 | 212 | 9.44 | 8.4 | 262 | 3.33 | 3.31 | 3.28 | 28 | 78.6 | 0.88 |
| Example 60 | I 52.85 (0.1) | ↑ | 0.86 | 208 | 9.21 | 8.6 | 243 | 3.28 | 3.27 | 3.23 | 24 | 79.6 | 0.84 |

Note:
Abbreviatons are the same as in Table 6~8

EXAMPLES 60~69

The same procedures as described in Example 16 were carried out by using diamine components and tetracarboxylic dianhydride components illustrated in Table 11 to obtain various polyimide copolymer powders. Further, polyimide copolymer films were prepared by the same procedures as described in Example 16.

TABLE 11

| | Diamine component g (mol) | Acid anhydride component g (mol) | η (dl/g) | Tg (°C.) | Mechanical property Ts (Kg/mm$^2$) | EL (%) | TM (Kg/mm) | Dielectric constant 60 Hz | 3 KHz | 1 MHz | YI | T 500 nm (%) | Moisture absorption (%) |
|---|---|---|---|---|---|---|---|---|---|---|---|---|---|
| Example 61 | mm-APB-CF$_3$-I 18.02 (0.05) mm-APB-CF$_3$-II 18.02 (0.05) | 6FDA 44.43 (0.1) | 0.86 | 204 | 9.33 | 3.6 | 342 | 2.92 | 2.90 | 2.88 | 9 | 86.2 | 0.48 |
| Example 62 | mm-APB-CF$_3$-II 18.02 (0.05) m-BP-6F 25.22 (0.05) | ↑ | 0.93 | 216 | 11.63 | 7.3 | 303 | 2.87 | 2.85 | 2.83 | 10 | 84.5 | 0.61 |
| Example 63 | m-BP-6F *1 25.22 (0.05) mm-APB-2CF$_3$ 21.42 (0.05) | ↑ | 1.04 | 213 | 10.84 | 7.8 | 294 | 2.85 | 2.83 | 2.80 | 8 | 86.5 | 0.45 |
| Example 64 | mm-APB-2CF$_3$ 21.42 (0.05) mm-APB-3CF$_3$ 24.82 (0.05) | ↑ | 0.96 | 194 | 9.14 | 5.6 | 314 | 2.85 | 2.82 | 2.79 | 7 | 87.1 | 0.34 |

Note:
*1) 4,4'-bis(3-amino-5-trifluoromethylphenoxy)biphenyl

| | Diamine component g (mol) | Acid anhydride component g (mol) | η (dl/g) | Tg (°C.) | Ts (Kg/mm$^2$) | EL (%) | TM (Kg/mm) | 60 Hz | 3 KHz | 1 MHz | YI | T 500 nm (%) | Moisture absorption (%) |
|---|---|---|---|---|---|---|---|---|---|---|---|---|---|
| Example 65 | mm-APB-CF$_3$ I 36.04 (0.1) | 6FDA 22.22 (0.05) ODPA 15.51 (0.05) | 0.69 | 193 | 10.22 | 5.0 | 330 | 3.06 | 3.05 | 3.02 | 10 | 86.4 | 0.74 |
| Example 66 | mm-APB-2CF$_3$ 42.84 (0.1) | 6FDA 22.22 (0.05) BPDA 14.71 (0.05) | 1.13 | 202 | 9.95 | 4.4 | 291 | 2.98 | 2.97 | 2.94 | 11 | 85.7 | 0.83 |
| Example 67 | mm-APB-CF$_3$-I | 6FDA 44.43 (0.1) | 0.77 | 216 | 9.04 | 4.9 | 336 | 2.96 | 2.94 | 2.91 | 9 | 86.0 | 0.59 |

TABLE 11-continued

| | Diamine component g (mol) | Acid anhydride component g (mol) | η (dl/g) | Tg (°C.) | Mechanical property | | | Dielectric constant | | | YI | T 500 nm (%) | Moisture absorption (%) |
|---|---|---|---|---|---|---|---|---|---|---|---|---|---|
| | | | | | Ts (Kg/mm²) | EL (%) | TM (Kg/mm) | 60 Hz | 3 KHz | 1 MHz | | | |
| Example 68 | 32.43 (0.09) m-BP *1 3.68 (0.01) mm-APB-2CF₃ 38.55 (0.09) mm-APB 2.92 (0.01) | 6FDA 44.43 (0.1) | 0.84 | 190 | 8.57 | 4.9 | 317 | 2.92 | 2.91 | 2.89 | 8 | 87.3 | 0.39 |
| Example 69 | mm-APB-3CF₃ 49.64 (0.1) | 6FDA 22.22 (0.09) ODPA 3.10 (0.01) | 0.93 | 179 | 9.18 | 4.6 | 301 | 2.88 | 2.86 | 2.84 | 8 | 87.0 | 0.32 |

Note:
*1 4,4'-bis(3-aminophenoxy)biphenyl
*2 Abbreviations are the same as in Table 4~8

What is claimed is:

1. A polyimide comprising a requisite structural unit having one or more recurring structural units of the formula (1):

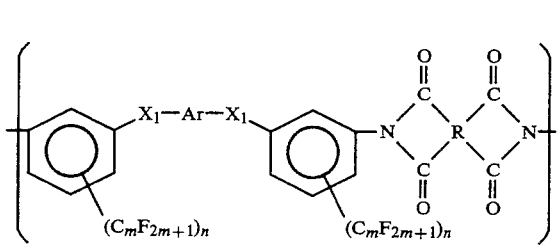

(1)

wherein $X_1$ is a direct bond or a divalent radical selected from the group consisting of —O—, —CO— and —C(CH₃)— and two $X_1$ are the same or different from each other, m is an integer of 1~6, n is individually 0 or an integer of 1~4, R is a tetravalent radical having 2~27 carbon atoms and being selected from the group consisting of aliphatic radical, alicyclic radical, monoaromatic radical, condensed polyaromatic radical and noncondensed aromatic radical connected to each other with a direct bond or a bridge member, and Ar is a divalent radical selected from the group consisting of

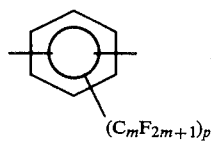

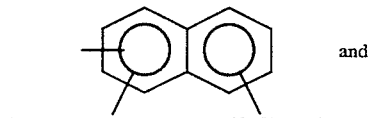

and

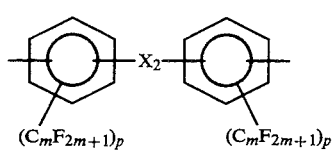

wherein $X_2$ is a direct bond or a divalent radical selected from the group consisting of —O—, —S—, —CO— and —C(CH₃)₂—, m is an integer of 1~6, and p is individually 0 or an integer of 1~4, or an integer of 1~4 when n is 0 in the formula (1).

2. A capped polyimide comprising a requisite structural unit having one or more recurring structural units of the formula (1):

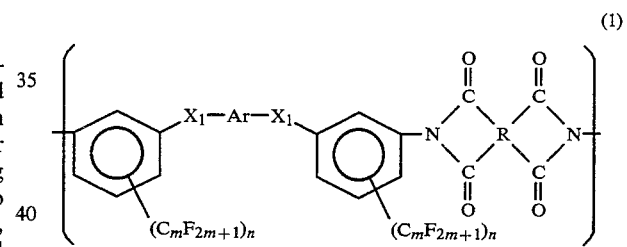

(1)

wherein $X_1$ is a direct bond or a divalent radical selected from the group consisting of —O—, —CO— and —C(CH₃)— and two $X_1$ are the same or different from each other, m is an integer of 1~6, n is individually 0 or an integer of 1~4, R is a tetravalent radical having 2~27 carbon atoms and being selected from the group consisting of an aliphatic radical, alicyclic radical, monoaromatic radical, condensed polyaromatic radical and noncondensed aromatic radical connected to each other with a direct bond or a bridge member, and Ar is a divalent radical selected from the group consisting of

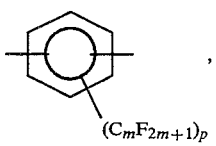

and

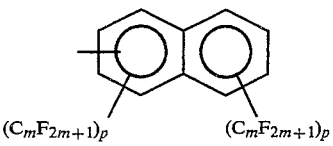

-continued

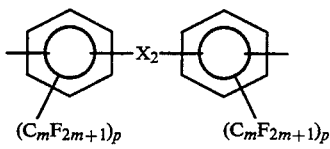

wherein $X_2$ is a direct bond or a divalent radical selected from the group consisting of —O—, —S—, —CO— and —C(CH$_3$)$_2$—, m is an integer of 1~6, and p is individually 0 or an integer of 1~4, or an integer of 1~4 when n is 0 in the formula (1), and having at the polymer chain end thereof an aromatic ring which is essentially unsubstituted or substituted with a radical having no reactivity for amine and dicarboxylic anhydride.

3. An aromatic polyimide or a capped aromatic polyimide having at the polymer chain end thereof an aromatic ring which is essentially unsubstituted or substituted with a radical having no reactivity for dicarboxylic anhydride, comprising a requisite structural unit having one or more recurring structural units of the formula (11):

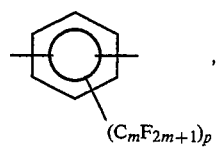

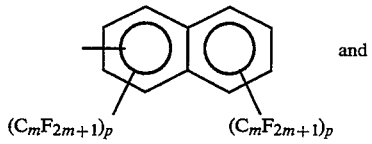

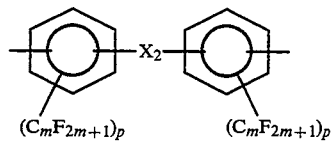

wherein $X_2$ is a direct bond or a divalent radical selected from the group consisting of —O—, —S—, —CO— and ——C(CH$_3$)$_2$, m is an integer of 1~6, and

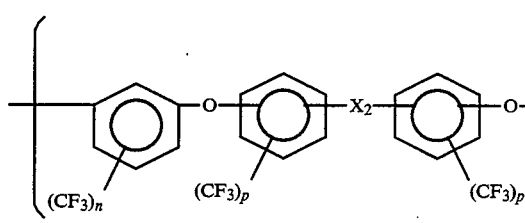

wherein $X_1$ is a direct bond or a divalent radical selected from the group consisting o —O—, —S—, —CO— and —C(CH$_3$)$_2$—, and n and p or 0 or an integer of 1~4 and are not simultaneously 0, and R is a tetravalent radical having 2-27 carbon atoms and being selected from the group consisting of an aliphatic radical, alicyclic radical, monoaromatic radical, condensed polyaromatic radical and noncondensed aromatic radical connected to each other with a direct bond or a bridge member.

4. A preparation process of polyimide comprising a requisite structural unit having one or more recurring structural units of the formula (1):

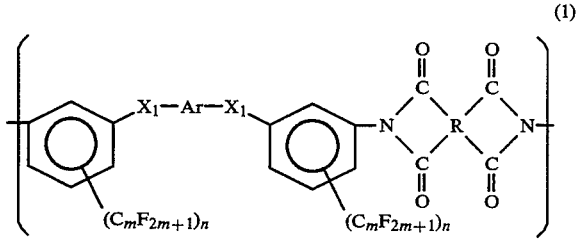

wherein $X_1$ is a direct bond or a divalent radical selected from the group consisting of —O—, —CO— and —C(H$_3$)$_2$—, two $X_1$ may be same or different, m is an integer of 1~6, n is 0 or an integer of 1~4, and Ar is a divalent radical selected from the group consisting of p individually 0 or an integer of 1~4, and an integer of 1~4 when n=0 in the formula (1), R is tetravalent radical having 2~27 carbon atoms and being selected from the group consisting of an aliphatic radical, alicyclic radical, monoaromatic radical, condensed polyaromatic radical and noncondensed aromatic radical connected to each other with a direct bond or a bridge member, which comprises reacting an aromatic diamine having one or more principal ingredients of the formula (13):

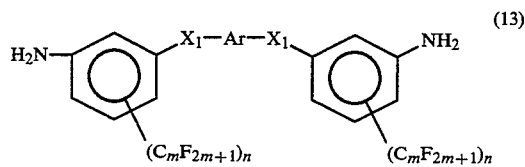

wherein $X_1$, Ar, m and n are the same as above, with one or more tetracarboxylic dianhydride principally represented by the formula (14):

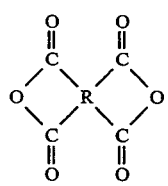

wherein R are the same as above, and thermally or chemically imidizing the resulting polyamic acid.

5. A preparation process of capped aromatic polyimide comprising a requisite structural unit having one or more recurring structural units of the formula (1):

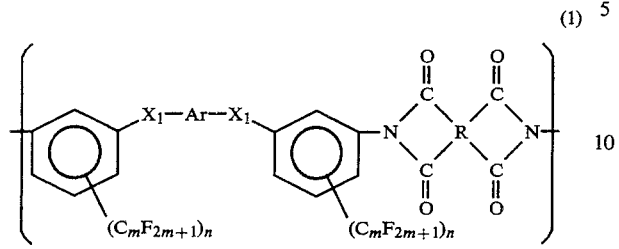
(1)

wherein X is a direct bond or a divalent radical selected from the group consisting of —O—, —CO— and —C(CH$_3$)$_2$—, two X$_1$ are the same or different, m is an integer of 1~6, n is ) or an integer of 1~4, and Ar is a divalent radical selected from the group consisting of

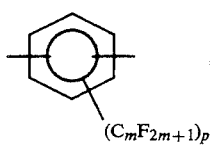,

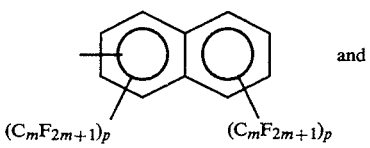 and

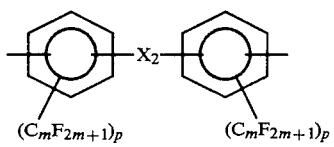

wherein X$_2$ is a direct bond or a divalent radical selected from the group consisting of —O—, —S—, —CO— and —C(CH$_3$)$_2$—, m is an integer of 1~6, and p individually 0 or an integer of 1~4, and an integer of 1~4 when n=0 in the formula (1), R is tetravalent radical having 2~27 carbon atoms and being selected from the group consisting of an aliphatic radical, alicyclic radical, monoaromatic radical, condensed polyaromatic radical and noncondensed aromatic radical connected to each other with a direct bond or a bridge member, and having at the polymer chain end thereof an aromatic ring which is essentially unsubstituted or substituted with a radical having no reactivity for amine and dicarboxylic anhydride, comprising reacting aromatic diamine having one or more principal ingredients of the formula (13):

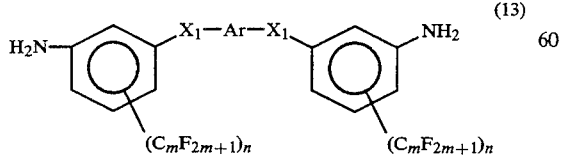
(13)

wherein X$_1$, Ar, m, and n are the same as above, with one or more tetracarboxylic dianhydride principally represented by the formula (14)

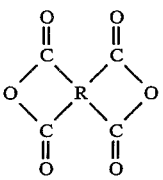
(14)

wherein R is the same as above, in the presence of aromatic dicarboxylic anhydride of the formula (15):

(15)

wherein Z is a divalent radical having 6~15 carbon atoms and being selected from the group consisting of a monoaromatic radical, condensed polyaromatic radical and noncondensed aromatic radical connected to each other with a direct bond or a bridge member, and/or aromatic monoamine of the formula (16)

Z$_1$—NH$_2$ (16)

wherein Z$_1$ is a monovalent radical having 6~15 carbon atoms and being selected from the group consisting of a monoaromatic radical, condensed polyaromatic radical and noncondensed aromatic radical connected to each other with a direct bond or a bridge member, and thermally or chemically imidizing the resulting polyamic acid.

6. The preparation process of claim 4 or claim 5 wherein the aromatic diamine has the formula (17):

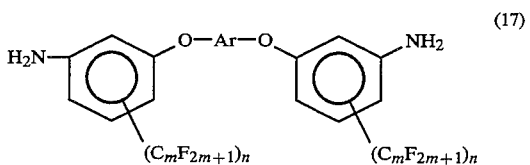
(17)

wherein m is an integer of 1~6, n is 0 or an integer of 1~4, and Ar is a divalent radical selected from the group consisting of

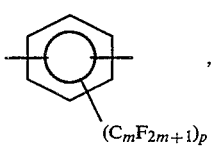,

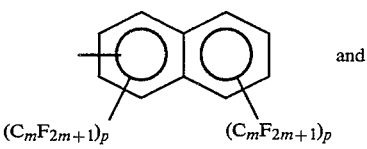 and

-continued

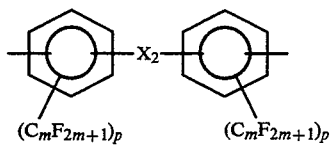

wherein X₂ is a direct bond or a divalent radical selected from the group consisting of —O—, —S—, —CO— and —C(CH₃)₂—, m is an integer of 1~6, and p is 0 or an integer of 1~4, and is an integer of 1~4 when n is 0 in the formula (17).

7. The preparation process of claim 4 or claim 5 wherein the aromatic diamine has the formula (21):

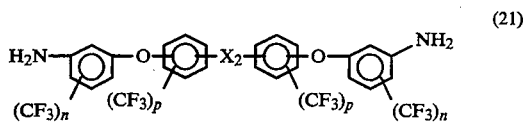

wherein X₂ is a direct bond or a divalent radical selected from the group consisting of —O—, —S—, —CO— and —C(CH₃)₂—, and n and p are individually 0 or an integer of 1~4 and are not simultaneously 0.

8. The polyimide of claim 1 or claim 2 wherein the polyimide having the recurring structural units of the formula (1) is derived from the polyamic acid precursor having an inherent viscosity of 0.01~3.0 dl/g at a concentration of 0.5 g/dl in a dimethylacetamide solution at 35° C.

9. A polyimide of claim 1 or claim 2 wherein the polyimide having reccuring structural units of the formula (1) has an inherent viscosity of 0.01~3.0 dl/g at 35° C. at a concentration of 0.5 g/dl in a solvent mixture composed of 9 parts by weight p-chlorophenol and 1 part by weight of phenol.

10. An aromatic polyimide or a capped aromatic polyimide having at the polymer chain end thereof an aromatic ring which is essentially unsubstituted or substituted with a radical having no reactivity for dicarboxylic anhydride, comprising a requisite structural unit having one or more recurring structural units of the formula (2):

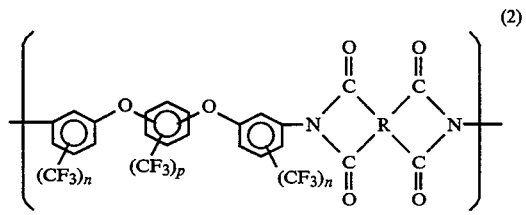

wherein n and p are 0 or an integer of 1~4, and are not simultaneously 0, and R is a tetravalent radical having 2~27 carbon atoms and being selected from the group consisting of an aliphatic radical, alicyclic radical, monoaromatic radical, condensed polyaromatic radical and noncondensed aromatic radical connected to each other with a direct bond or a bridge member.

11. An aromatic polyimide or a capped aromatic polyimide having at the polymer chain end thereof an aromatic ring which is essentially unsubstituted or substituted with a radical having no reactivity for dicarboxylic anhydride, comprising a requisite structural unit having one or more recurring structural units of the formula (3):

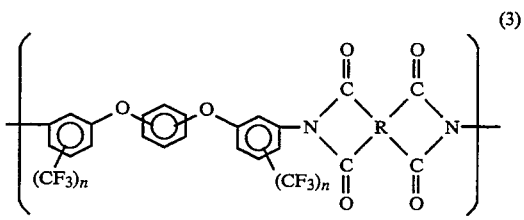

wherein n is an integer of 1~4 and R is a tetravalent radical having 2~27 carbon atoms and being selected from the group consisting of an aliphatic radical, alicyclic radical, mono aromatic radical, condensed polyaromatic radical and noncondensed aromatic radical connected to each other with a direct bond or a bridge member.

12. An aromatic polyimide or a capped aromatic polyimide having at the polymer chain end thereof an aromatic ring which is essentially unsubstituted or substituted with a radical having no reactivity for dicarboxylic anhydride, comprising a requisite structural unit having one or more recurring structural units of the formula (4):

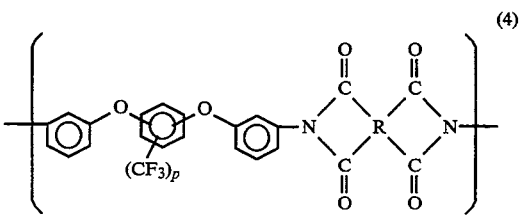

wherein n is an integer of 1~4 and R is a tetravalent radical having 2~27 carbon atoms and being selected from the group consisting of an aliphatic radical, alicyclic radical, monoaromatic radical, condensed polyaromatic radical and noncondensed aromatic radical connected to each other with a direct bond or a bridge member.

13. An aromatic polyimide or a capped aromatic polyimide having at the polymer chain end thereof an aromatic ring which is essentially unsubstituted or substituted with a radical having no reactivity for dicarboxylic anhydride, comprising a requisite structural unit having one or more recurring structural units selected from the group consisting of the formulas (5), (6), (7), (8), (9) and (10):

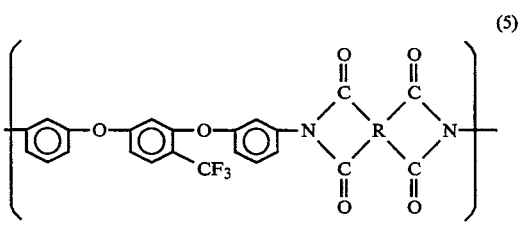

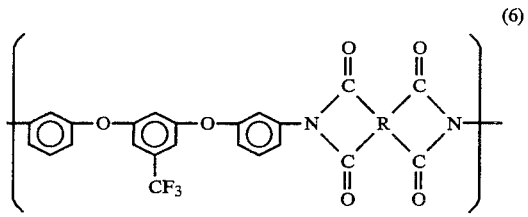
(6)

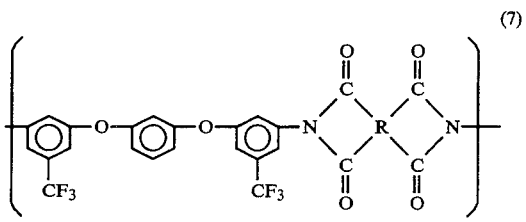
(7)

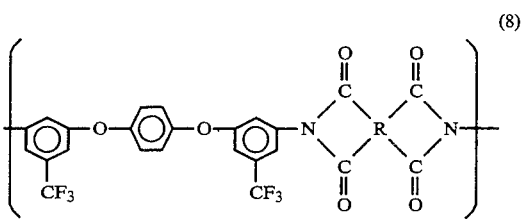
(8)

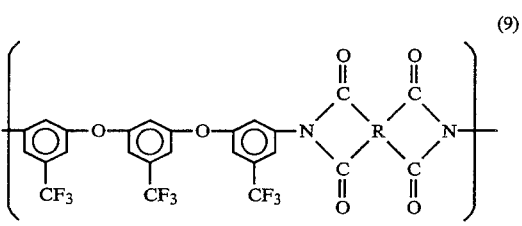
(9)

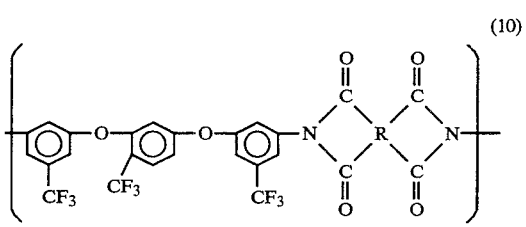
(10)

wherein R is a tetravalent radical having 2-27 carbon atoms and being selected from the group consisting of an aliphatic radical, alicyclic radical, monoaromatic radical, condensed polyaromatic radical and noncondensed aromatic radical connected to each other with a direct bond or a bridge member.

14. An aromatic polyimide or a capped aromatic polyimide having at the polymer chain end thereof an aromatic ring which is essentially unsubstituted or substituted with a radical having no reactivity for dicarboxylic anhydride, comprising a requisite structural unit having one or more recurring structural units of the formula (12):

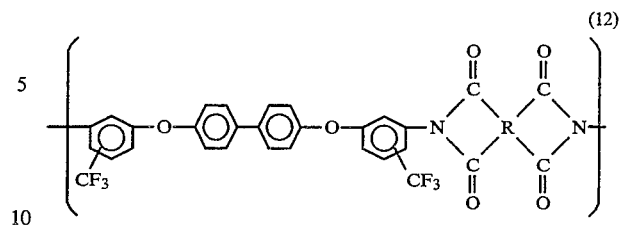
(12)

wherein R is a tetravalent radical having 2~27 carbon atoms and being selected form the group consisting of an aliphatic radical, alicyclic radical, monoaromatic radical, condensed polyaromatic radical and noncondensed aromatic radical connected to each other with a direct bond or a bridge member.

15. The preparation process of claim 4 or claim 5 wherein the aromatic diamine has the formula (18):

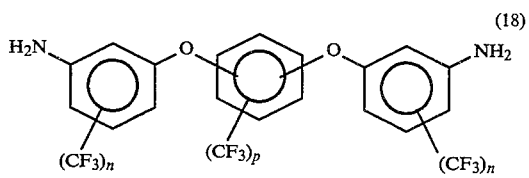
(18)

wherein n and p are 0 or an integer of 1, and are not simultaneously 0.

16. The preparation process of claim 4 or claim 5 wherein the aromatic diamine has the formula (19):

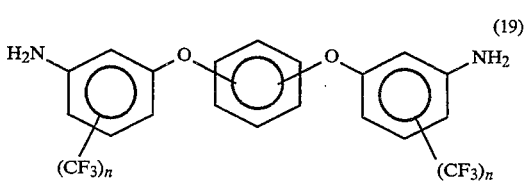
(19)

wherein n is an integer of 1~4.

17. The preparation process of claim 4 or claim 5 wherein the aromatic diamine has the formula (20):

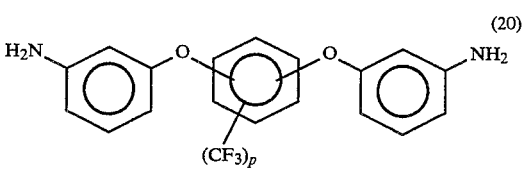
(20)

wherein p is an integer of 1~4.

18. The preparation process of claim 4 or claim 5 wherein the aromatic diamine is one or more compounds selected from the group consisting of 1,3-bis(3-aminophenoxy)-4-trifluoromethylbenzene, 1,3-bis(3-aminophenoxy)-5-trifluoromethylbenzene, 1,3-bis(3-amino-5-trifluoromethylphenoxy)benzene, 1,4-bis(3-amino-5-trifluoromethylphenoxy)benzene and 1,3-bis(3-amino-5-trifluoromethylphenoxy)-4-trifluoromethylbenzene.

19. The preparation process of claim 4 or claim 5 wherein the aromatic diamine has the formula (22):

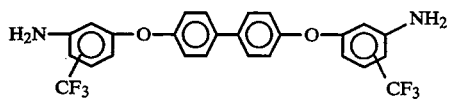 (22)

20. The preparation process of claim 4 or claim 5 wherein the aromatic diamine is 4,4-bis(3-amino-5-fluoromethylphenoxy)biphenyl.

21. The preparation process of claim 5 wherein the aromatic dicarboxylic anhydride is phthalic anhydride.

22. The preparation process of claim 5 wherein the aromatic monoamine is aniline.

23. The preparation process of claim 5 wherein the amount of the aromatic dicarboxylic anhydride is 0.001~1.0 mol per mol of the aromatic diamine.

24. The preparation process of claim 23 wherein the amount of phthalic anhydride is 0.001~1.0 mol per mol of the aromatic diamine.

25. The preparation process of claim 5 wherein the amount of the aromatic monoamine is 0.001~1.0 mol per mol of the tetracarboxylic dianhydride.

26. The preparation process of claim 25 wherein the amount of aniline is 0.001~1.0 mol per mol of the tetracarboxylic dianhydride.

27. A composition comprising polyimide in one of claims 1, 2, 3, 10, 11, 12, 13, and 14.

28. A polyimide film comprising polyimide in one of claims 1, 2, 3, 10, 11, 12, 13, and 14.

* * * * *

UNITED STATES PATENT AND TRADEMARK OFFICE
CERTIFICATE OF CORRECTION

PATENT NO. : 5,354,839

DATED : October 11, 1994

INVENTOR(S) : Yamashita et al.

It is certified that error appears in the above-indentified patent and that said Letters Patent is hereby corrected as shown below:

On the title page, item [75] delete inventors names "Mitsunori Matsuo; Tsutomu Ishida, and Keizaburo Yamaguchi".

In the Abstract, line 3 of the last paragraph thereof, delete ", and also provides an aromatic diamine which is useful as a raw material monomer of the polyimide or a raw material of other various engineering plastics".

Claim 1, column 59, line 55 and

Claim 2, column 60, line 65, and

Claim 4, column 62, line 10, and

Claim 5, column 63, line 30, and

UNITED STATES PATENT AND TRADEMARK OFFICE
CERTIFICATE OF CORRECTION

PATENT NO. : 5,354,839
DATED : October 11, 1994
INVENTOR(S) : Yamashita et al.

It is certified that error appears in the above-indentified patent and that said Letters Patent is hereby corrected as shown below:

Claim 6, column 64, line 65, correct the formula as shown below:

from: 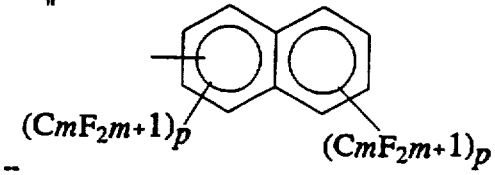

to: 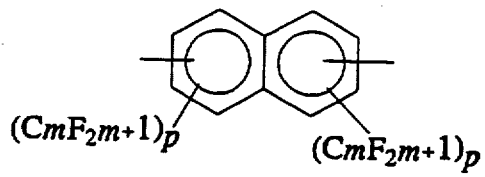

Signed and Sealed this

Second Day of May, 1995

Attest:

BRUCE LEHMAN

Attesting Officer   Commissioner of Patents and Trademarks